(12) United States Patent
Baker, Jr. et al.

(10) Patent No.: US 10,138,279 B2
(45) Date of Patent: Nov. 27, 2018

(54) **COMPOSITIONS AND METHODS FOR *BACILLUS ANTHRACIS* VACCINATION**

(75) Inventors: James R. Baker, Jr., Ann Arbor, MI (US); Anna Bielinska, Ypsilanti, MI (US); Andrzej Myc, Ann Arbor, MI (US)

(73) Assignee: Regents of the University of Michigan, Ann Arbor, MI (US)

( * ) Notice: Subject to any disclaimer, the term of this patent is extended or adjusted under 35 U.S.C. 154(b) by 1396 days.

(21) Appl. No.: 11/786,861

(22) Filed: Apr. 13, 2007

(65) Prior Publication Data

US 2015/0266933 A1    Sep. 24, 2015

Related U.S. Application Data

(60) Provisional application No. 60/791,759, filed on Apr. 13, 2006.

(51) Int. Cl.
*A61K 51/10* (2006.01)
*C07K 14/32* (2006.01)
*A61K 39/07* (2006.01)
*A61K 39/00* (2006.01)

(52) U.S. Cl.
CPC ............. *C07K 14/32* (2013.01); *A61K 39/07* (2013.01); *A61K 2039/543* (2013.01); *A61K 2039/55561* (2013.01); *A61K 2039/55566* (2013.01); *A61K 2039/55572* (2013.01); *A61K 2039/57* (2013.01); *A61K 2039/575* (2013.01)

(58) Field of Classification Search
None
See application file for complete search history.

(56) References Cited

U.S. PATENT DOCUMENTS

| | | | |
|---|---|---|---|
| 4,481,188 A | 11/1984 | Apontoweil et al. | |
| 4,895,452 A | 1/1990 | Yiournas | |
| 4,895,454 A | 1/1990 | Kammleiter et al. | |
| 5,103,497 A | 4/1992 | Hicks | |
| 5,510,104 A | 4/1996 | Allen | |
| 5,547,677 A | 8/1996 | Wright | |
| 5,549,901 A | 8/1996 | Wright | |
| 5,571,531 A | 11/1996 | McDermott et al. | |
| 5,618,840 A | 4/1997 | Wright | |
| 5,662,957 A | 9/1997 | Wright | |
| 5,700,679 A | 12/1997 | Wright | |
| 5,716,637 A | 2/1998 | Anselem et al. | |
| 5,942,237 A | 8/1999 | Gizurarson et al. | |
| 5,951,988 A | 9/1999 | Littel-Van Den Hurk et al. | |
| 5,961,970 A | 10/1999 | Lowell et al. | |
| 6,015,832 A | 1/2000 | Baker et al. | |
| 6,350,784 B1 | 2/2002 | Squires | |
| 6,506,803 B1 | 1/2003 | Baker et al. | |
| 6,558,695 B2 | 5/2003 | Luo et al. | |
| 6,559,189 B2 | 5/2003 | Baker, Jr. et al. | |
| 6,565,873 B1 | 5/2003 | Shefer et al. | |
| 6,627,198 B2 | 9/2003 | Reed et al. | |
| 6,635,676 B2 | 10/2003 | Baker, Jr. et al. | |
| 7,314,624 B2 * | 1/2008 | Baker et al. ............... | 424/192.1 |
| 7,371,395 B2 | 5/2008 | Parisot et al. | |
| 2001/0037100 A1 | 11/2001 | Shanklin | |
| 2002/0119207 A1 | 8/2002 | Baker, Jr. et al. | |
| 2002/0155084 A1 | 10/2002 | Roessler et al. | |
| 2003/0194412 A1 | 10/2003 | Baker et al. | |
| 2003/0202982 A1 | 10/2003 | Birkett | |
| 2003/0224403 A1 * | 12/2003 | Popov ................ | C07K 16/2875 435/6.15 |
| 2004/0043041 A1 | 3/2004 | Baker, Jr. et al. | |
| 2005/0079185 A1 | 4/2005 | Parisot et al. | |
| 2005/0208083 A1 | 9/2005 | Annis | |
| 2005/0238660 A1 | 10/2005 | Babiuk | |
| 2005/0281843 A1 | 12/2005 | Singh | |
| 2006/0257426 A1 * | 11/2006 | Baker et al. ............... | 424/204.1 |
| 2008/0181949 A1 * | 7/2008 | Baker et al. ................. | 424/484 |

FOREIGN PATENT DOCUMENTS

| | | |
|---|---|---|
| JP | H05-294845 | 11/1993 |
| JP | H10-500686 | 1/1998 |
| WO | 94/00153 | 1/1994 |
| WO | 94/21292 | 9/1994 |
| WO | 1995-011700 | 5/1995 |
| WO | 95/17210 | 6/1995 |
| WO | 96/33739 | 10/1996 |
| WO | 1997-029773 | 8/1997 |

(Continued)

OTHER PUBLICATIONS

Baker et al. ( Journal of Allergy and Clinical Immunology, vol. 113, No. 2, S292 , Feb. 2004). Abstract only.*
Baker et al. Journal of Allergy and Clinical Immunology vol. 113, No. 2 S292, 2004.*
Clin Vaccine Immunol. Feb. 2006; 13(2): 208-213. Neutralizing Antibodies and Persistence of Immunity following Anthrax Vaccination Hanson et al.*
Portocala et al., Immunoelectrophoretic characterization of Sendai virus antigens, Virologie 27:261 (1976).
Richter and Kipp, Transgenic Plants as Edible Vaccines, Curr Top Microbiol Immunol 240:159-76 (1999).
Roberts, Resistance of Vaccinia Virus to Inactivation by Solvent/ Detergent Treatment of Blood Products, Biologicals (2000) 28, 29-32.

(Continued)

*Primary Examiner* — Jana A Hines
*Assistant Examiner* — Khatol S Shahnan Shah
(74) *Attorney, Agent, or Firm* — Casimir Jones S.C.; Tyler J. Sisk

(57) ABSTRACT

The present invention relates to methods and compositions for stimulating an immune response. Specifically, the present invention provides methods of inducing an immune response to bacteria of the genus *Bacillus* (e.g., *Bacillus anthracis*) in a subject (e.g., a human subject) and compositions useful in such methods (e.g., a nanoemulsion comprising *Bacillus anthracis* or an immunogenic portion thereof). Compositions and methods of the present invention find use in, among other things, clinical (e.g. therapeutic and preventative medicine (e.g., vaccination) and research applications.

14 Claims, 12 Drawing Sheets

Specification includes a Sequence Listing.

(56) References Cited

FOREIGN PATENT DOCUMENTS

| WO | 98/56414 | 12/1998 |
|----|----------|---------|
| WO | 99/11241 | 3/1999 |
| WO | 99/12565 | 3/1999 |
| WO | 1999-033459 | 7/1999 |
| WO | 2000-050006 | 8/2000 |
| WO | 2004-030608 | 4/2004 |
| WO | 2005-027872 | 3/2005 |

OTHER PUBLICATIONS

Ruedl and Wolf, Features of Oral Immunization, Int. Arch. Immunol., 108:334 (1995).
Russell, Bacterial Spores and Chemical Sporicidal Agents, Clin. Micro. 3:99 (1990).
Sandusky et al., An Evaluation of Aureomycin and Chloromycetin in Experimental Clostridium Welchii Infection, Surgery, 28:632 (1950).
Sercarz et al., Dominance and Crypticity of T Cell Antigenic Determinants, Anu Rev Immunol 11:729 (1993).
Silins et al., Development of Epstein-Barr Virus-specific Memory T Cell Receptor Clonotypes in Acute Infectious Mononucleosis, J Exp Med 184:1815 (1996).
Steven et al., Epitope Focusing in the Primary Cytotoxic T Cell Response to Epstein-Barr Virus and Its Relationship to T Cell memory, J Exp Med 184:1801 (1996).
Stevens et al., Comparison of Clindamycin, Rifampin, Tetracycline, metronidazole, and penicillin for Effiacy in Prevention of Experimental Gas Gangrene Due to clostridium perfringens, J. Infect. Dis., 155:220 (1987).
Stevens et al., Comparison of Single and Combination Antimicrobial Agents for Prevention of Experimental Gas Gangrene Caused by Clostridium perfringens, Antimicrob. Agents Chemother., 31:312 (1987).
Takeuchi et al., Experimental Bacillary Dysentery: An Electron Microscopic Study of the Response of the intestinal Mucosa to Bacterial Invasion, Am. J. Pathol., 47:1011 (1965).
Tremblay et al., T Lymphocyte Responses to Multiple Minor Histocompatibility Antigens Generate Both Self-Major Histocompatibility Complex-Restricted and Cross-Reactive Cytotoxic T Lymphocytes, Transplantation 58:59-67 (1994).
Tumpey et al., Mucosal delivery of inactivated influenza vaccine induces B-cell-dependent heterosubtypic cross-protection against lethal influenza A H5N1 virus infection. Journal of virology, Jun. 2001, vol. 75, No. 11, pp. 5141-5150.

Welkos and Friedlander, comparative safety and efficacy against Bacillus anthracis of protective antigen and live vaccines in mice, Microb Pathog 5:127 (1988).

Welkos et al., Differences in Susceptibility of Inbred Mice to Bacillus anthracis, Infect Immun. 51:795 (1986).

Yanagita, Biochemical Aspects on the Germination of Conidiospores of Aspergillus niger, Arch Mikrobiol 26:329 (1957).

Hamouda T et al: "A Novel Surfactant Nanoemulsion with a unique non-irritant topical antimicrobial activity against bacteria, enveloped viruses and fungi" Microbiological Research vol. 156, No. 1, Jan. 1, 2001, pp. 1-07.

Myc et al., Development of immune response that protects mice from viral pneumonitis after a single intranasal immunization with influenza A virus and nanoemulsion, Vaccine, Sep. 2003, vol. 21 (25-26), pp. 3801-3814.

Turner et al., Inactivated smallpox vaccine. A comparison of inactivation methods; J. Hyg., Camb., 1970, 68, p. 197.

Altemeier et al., Chloromycetin and Aureomycin in Experimental Gas Gangrene, Surgery, 28:621 (1950).

Baker Jr., et al., Enhanced systemic and mucosal immune responses in mice immunized with recombinant Bacillus anthracis protective antigen (rPA) using a novel nanoemulsion adjuvant, Journal of Allergy and Clinical Immunology, vol. 113, No. 2 Supplement, Feb. 2004, p S292 XP 002560178 & 60th Annual Meeting of the American Academy of Allergy, Asthma and Immunology (AAAAI); San Francisco, CA, USA; Mar. 19-23, 2004.

Mims and Murphy, Parainfluenza Virus Sendai Infection in Macrophages, Ependyma, Choroid Plexus, Vascular Endothelium and Respiratory Tract of Mice, Am. J. Path., 70:315 (1973).

Mor et al., Perspective: edible vaccines—a concept coming of age, Trends Micrbiol 6:449-53 (1998).

Brown et al., Differential Diagnosis of Bacillus Cereus, Bacillus Anthracis, and Bacillus Cereus Var. Mycoides, J. Bact., 75:499 (1958).

Burdon and Wende, On the Differentiation of Anthrax Bacilli from Bacillus Cereus, J Infect. Diseas. 170(2):224-34 (1960).

Burdon et al., Experimental Infection of Mice with Bacillus Cereus: Studies of Pathogenesis and Pathologic Changes, J Infect. Diseas. 117:307 (1967).

Butterton et al., Development of a Germfree Mouse Model of Vibrio cholerae Infection, Infect. Immun., 64:4373 (1996).

Carter and Collins, The Route of Enteric Infection in Normal Mice, J. Exp. Med., 139:1189 (1974).

Castleman et al., Pathogenesis of Bronchiolitis and Pneumonia Induced in neonatal and Weanling Rats by Parainfluenza (Sendai) Virus, Am. J. Path., 129:277 (1987).

Castleman, Respiratory tract lesions in weanling outbred rats infected with Sendai virus, Am. J. Vet. Res., 44:1024 (1983).

Collins and Carter, Comparative Immunogenicity of Heat-Killed and Living Oral Salmonella Vaccines, Infect. Immun., 6:451 (1972).

Collins, Salmonellosis in Orally Infected Specific Pathogen-Free C557B1 Mice, Infect. Immun., 5:191 (1972).

Cox et al., Influenza virus: immunity and vaccination strategies, comparison of the immune response to inactivated and live, attenuated influenza vaccines. Scandinavian Journal of Immunology, vol. 59, p. 1-15, 2004.

Perreault et al. Immunodominant minor histocompatibility antigens: the major ones, Immunol Today 19:69 (1998).

Donovan et al., Prevention of murine influenza A virus pneumonitis by surfactant nano-emulsions. Antiviral Chemistry and Chemotherapy, 2000, vol. 11, pp. 41-49.

Drobniewski, Bacillus cereus and Related Species, Clin. Microbio. Rev. 6:324 (1993).

Eriksson et al., Virus validation of plasma-derived products produced by Pharmacia, with particular reference to immunoglobulins, Blood Coagulation and Fibtinolysis 5 (Suppl. 3):S37-S44 (1994).

Naughton et al., A rat model of infection by *Salmonella typhimurium* or *Salm. enteritidis*, J. Appl. Bact., 81:651 (1996).

Fields, Fields Virology, (Knipe, Howley (editors)), Lippincott Williams & Wilkins Publishers; Aug. 2001, p. 1555.

Finkelstein et al., Pathogenesis of Experimental Cholera in Infant Rabbits, J. Infect. Dis., 114:203 (1964).

Formal et al. Role of the Small intestine in an Experimental infection in Guinea Pigs, J. Bact. 85:119 (1963).

Freter, Experimental Enteric Shigella and Vibrio Infections in Mice and Guinea Pigs, J. Exp. Med., 104:411 (1956).

Freter, The Fatal Enteric Cholera Infection in the Guinea Pig, Achieved by Inhibition of Normal Enteric Flora, J. Infect. Dis., 97:57 (1955).

Fritz et al., Pathology of Experimental Inhalation Anthrax in the Rhesus Monkey, Lab. Invest. 73:691 (1995).

Halvorson and Church, Biochemistry of Spores of Aerobic Bacilli with Special Reference to Germination, Bacteriol Rev. 21:112 (1957).

Hamouda and Baker, Antimicrobial mechanism of action of surfactant lipid preparations in enteric Gram-negative bacilli, J. Appl. Microbiol., 89:397 (2000).

Hamouda et al., A Novel Surfactant nanoemulsion with Broad-Spectrum Sporicidal Activity against Bacillus Species, J. Infect Dis., 180:1939-1949 (1999).

Hills, Chemical Factors in the Germination of Spore-bearing Aerobes: observations on the Influence of Species, Strain and Conditions of Growth, J. Gen. Micro. 4:38 (1950).

Horowitz et al., Solvent/Detergent-Treated Plasma: A Virus-Inactivated Substitute for Fresh Frozen Plasma, Blood 79:826 (1992).

(56) References Cited

OTHER PUBLICATIONS

Jacoby et al., Sendai Viral Pneumonia in Aged BALB/c Mice, Exp. Gerontol., 29:89 (1994).
Johnson et al., Age-dependent Resistance to Viral Encephalitis: Studies of Infections Due to Sindbis Virus in Mice, J. Infect. Dis., 125:257 (1972).
Johnson et al., Virus Invasion of the Central Nervous System, Am. J. Path., 46:929 (1965).
Karaivanova and Spiro, Sulphation of N-linked oligosaccharides of vesicular stomatitis and influenza virus envelope blycoproteins: host cell specifity, subcellular localization and identification of substituted saccharides, Biochem J. 329(Pt 3):511 (1998).
O'Hagan, D. Recent advances in Vaccine adjuvants for systemic and mucosal administration. J. Pharm. Pharmacol., 1997, vol. 1-10.
Labrec et al., Epithelial Cell Penetration as an Essential Step in the Pathogenesis of Bacillary Dysentery, J. Bact. 88:1503 (1964).
Lamanna and Jones, Lethality for Mice of Vegetative and Spore Forms of Bacillus Cereus and Bacillus Cereus-Like Insect Pathogens Injected intraperitoneally and Subcutaneously, J. Bact. 85:532 (1963).
Paul, Fundamental Immunology, Lippincott Williams & Wilkins Publishers; 5th edition Sep. 2003, p. 1353.
Levine et al., New Knowledge on Pathogenesis of Bacterial Enteric Infections as Applied to Vaccine Development, Microbiol. Rev., 47:510 (1983).
Maha and Igarashi, The Effect of Nonionic Detergent on Dengue and Japanese Encephalitis Virus Antigens in Antigen Detection Elisa and IgM-Capture Elisa, Southeast Asian J. Trop. Med. Pub. Health 28:718 (1997).
Mammen et al., Effective Inhibitors of Hemagglutination by Influenza Virus Synthesized from Plymers Having Active Ester Groups. insight into Mechanism of Inhibition, J Med Chem 38:4179 (1995).
Massion et al., Parainfluenza (Sendai) Virus Infects Ciliated Cells and Secretory Cells but Not Basal Cells of Rat Tracheal Epithelium, Am. J. Respir. Cell Mol. Biol. 9:361 (1993).
McMichael, Cytotoxic T Lymphocytes Specific for Influenza Virus, Curr. Top. Microbiol. Immunol. 189:75 (1994).
Brewer, J.M., (How) do aluminium adjuvants work?, Immunol Lett. Jan. 15, 2006;102(1):10-5. Epub Aug. 30, 2005.
Neutra, M.R. and P.A. Kozlowski, Mucosal vaccines: the promise and the challenge, Nat Rev Immunol. Feb. 2000;6 (2):148-58.
Vaccine Design—the Subunit and Adjuvant Approach, edited by Powell and Newman, Plenum Press, New York, 1995.
Chen, H., Recent advances in mucosal vaccine development, J Control Release. Jul. 3, 2000;67(2-3):117-28.
Costigan, The Toxicology of Nanoparticles Used in Healthcare Products, Reprot for the Committee on Human medicine, Sep. 2006, Retrieved from the internet.
Debin, A., et al., Intranasal immunization with recombinant antigens associated with new cationic particles induces strong mucosal as well as systemic antibody and CTL responses, Vaccine. Jun. 21, 2002:20(21-22):2752-63.
Easterday et al., Use of single nucleotide polymorphisms in the plcR gene for specific identification of Bacillus anthracis, J Clin Microbiol. Apr. 2005;43(4):1995-7.
Farchaus, J., et al., Fermentation, purification, and characterization of protective antigen from a recombinant, avirulent strain of Bacillus anthracis, Appl Environ Microbiol. Mar. 1998;64(3):982-91.
Hilgers et al., Synergistic effects of synthetic adjuvants on the humoral immune response, Int Arch Allergy Appl Immunol. 1986;79(4):392-6.
Lambert, P.-H. et al., Can successful vaccines teach us how to induce efficient protective immune responses?, Nat Med. Apr. 2005;11(4 Suppl):S54-62.
Mosmann and Coffman, TH1 and TH2 cells: different patterns of lymphokine secretion lead to different functional properties, Annu Rev Immunol. 1989;7:145-73.
Neutra, M.R. and P.A. Kozlowski, Mucosal vaccines: the promise and the challenge, Nat Rev Immunol. Feb. 2006;6(2):148-58.
Van Ginkel et al., Enterotoxin-based mucosal adjuvants alter antigen trafficking and induce inflammatory responses in the nasal tract, Infect Immun. Oct. 2005;73(10):6892-902.
Boyaka et al., Effective mucosal immunity to anthrax: neutralizing antibodies and Th cell responses following nasal immunization with protective antigen, J Immunol. Jun. 1, 2003;170(11):5636-43.
Flick-Smith et al., Mucosal or parenteral administration of microsphere-associated Bacillus anthracis protective antigen protects against anthrax infection in mice, Infect Immun. Apr. 2002;70(4):2022-8.
Jendrek et al., Evaluation of the compatibility of a second generation recombinant anthrax vaccine with aluminum-containing adjuvants, Vaccine. Jun. 20, 2003;21(21-22):3011-8.
Berthold et al., Immunogenicity in mice of anthrax recombinant protective antigen in the presence of aluminum adjuvants, Vaccine. Mar. 14, 2005;23(16):1993-9.
Friedlander et al., Anthrax vaccine: evidence for safety and efficacy against inhalational anthrax, JAMA, 282(22):2104-2106 (1999).

* cited by examiner

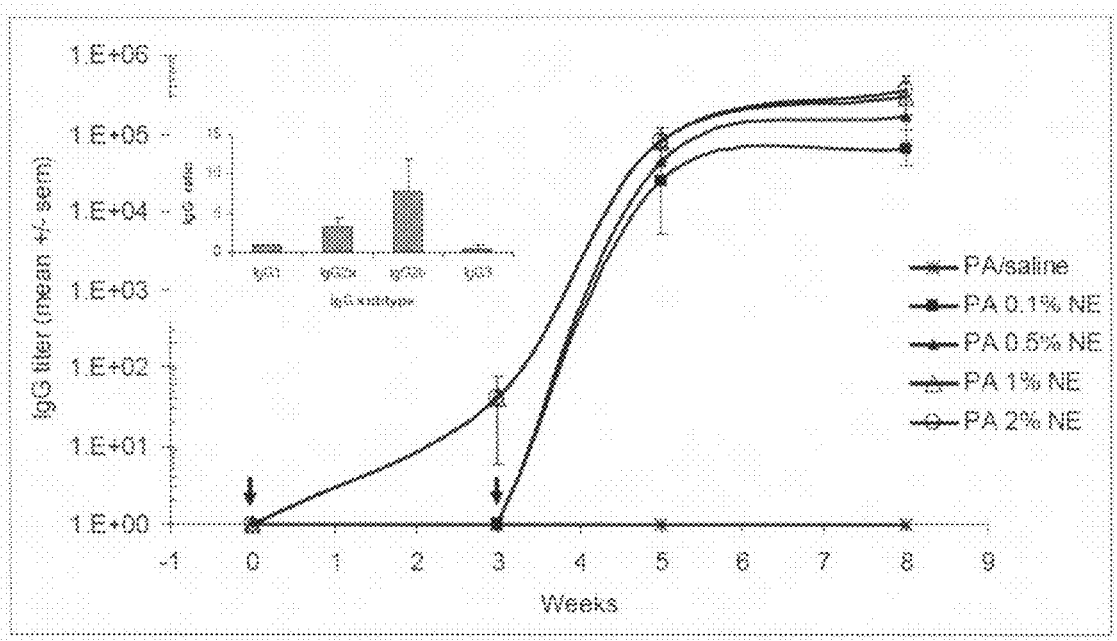

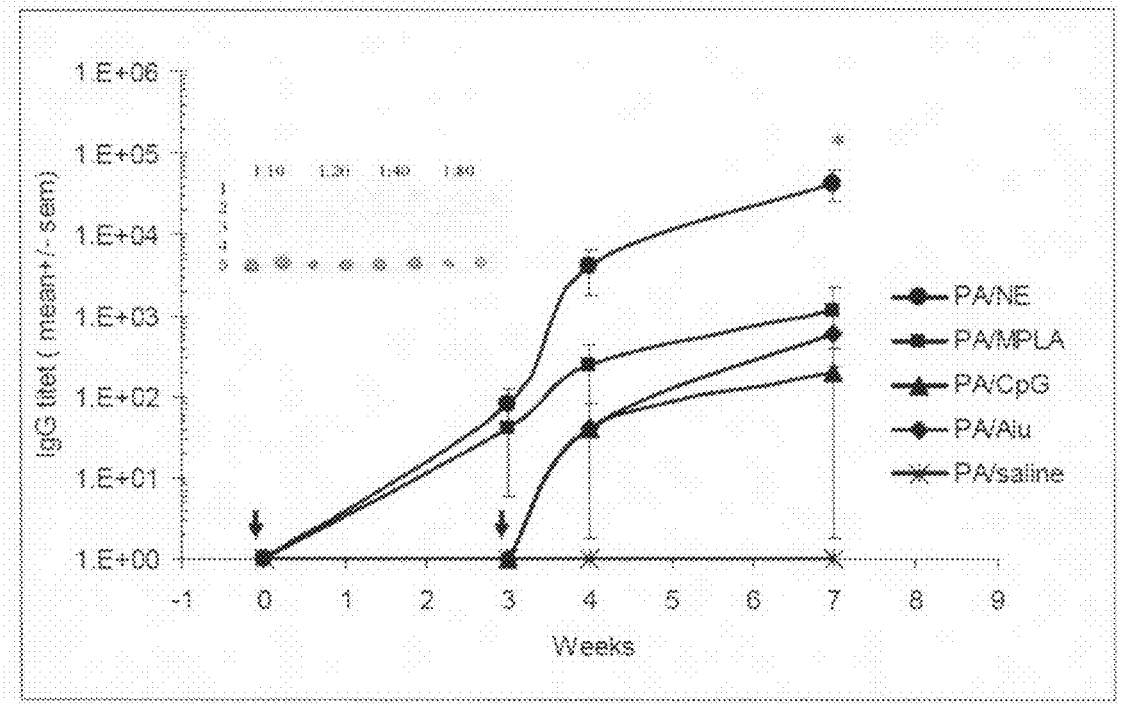

COMPOSITIONS AND METHODS FOR *BACILLUS ANTHRACIS* VACCINATION

The present invention claims priority to U.S. Provisional Patent Application Ser. No. 60/791,759 filed Apr. 13, 2006, hereby incorporated by reference in its entirety.

This invention was made with government support under contract U54 AI57153-02 awarded by the National Institutes of Health and contract MDA972-97-1-0007 awarded by the Department of Defense-Defense Advanced Research Projects Agency. The government has certain rights in the invention.

FIELD OF THE INVENTION

The present invention relates to methods and compositions for stimulating an immune response. Specifically, the present invention provides methods of inducing an immune response to bacteria of the genus *Bacillus* (e.g., *Bacillus anthracis*) in a subject (e.g., a human subject) and compositions useful in such methods (e.g., a nanoemulsion comprising *Bacillus anthracis* or an immunogenic portion thereof). Compositions and methods of the present invention find use in, among other things, clinical (e.g. therapeutic and preventative medicine (e.g., vaccination)) and research applications.

BACKGROUND OF THE INVENTION

Often, the first step in microbial (e.g., bacterial and bacterial spore, fungal and viral) infection (e.g., of animals) is attachment or colonization of skin or mucus membranes, followed by subsequent invasion and dissemination of the infectious microbe.

*B. anthracis*, a gram-positive, non-motile, spore-forming bacterium, is the etiological agent of anthrax. Spores from *B. anthracis* are extremely resistant to a wide range of adverse environmental conditions, such as heat, ultraviolet and ionizing radiation, and chemical agents (See, e.g., Mock and Fouet. Annu. Rev. Microbiol 2001; 55:647-671). *B. anthracis* Ames strain is very lethal, 100 spores is equal to one $LD_{50}$ (50% lethal dose). With the emergence of *B. anthracis* spores as a weapon of terror (See, e.g., Jernigan et al. Emer. Inf. Dis. 2001; 7:933-933), it is important to develop new vaccines to prevent and new therapies to control *B. anthracis* infections. The anthrax vaccine currently licensed for human use in the United States is composed of a sterile culture supernatant of an attenuated pXO1+, pXO2 *B. anthracis* strain. This undefined nature of the components and the requirement for six immunizations over 18 months followed by annual boosters also suggests a need for improved, alternative vaccines or treatments.

While an anthrax vaccine is available (See e.g., Ivins et al., Vaccine 13:1779 (1995)) and can be used for the prevention of classic anthrax, genetic mixing of different strains of the organism can render the vaccine ineffective (See e.g., Mobley, Military Med. 160:547 (1995)). The potential consequences of the use of Anthrax spores as a biological weapon was demonstrated by the accidental release of *B. anthracis* from a military microbiology laboratory in the former Soviet Union. Seventy-seven cases of human anthrax, including 66 deaths, were attributed to the accident. Some anthrax infections occurred as far as 4 kilometers from the laboratory (See e.g., Meselson et al., Science 266:1202 (1994)). Genetic analysis of infected victims revealed the presence of either multiple strains or a genetically altered *B. anthracis* (See e.g., Jackson et al., Proc. Nat. Acad. of Sci. U.S.A. 95:1224 (1998)).

Additionally, other members of the genus *Bacillus* are also reported to be etiological agents for many human diseases. *Bacillus cereus* is a common pathogen. It is involved in food borne diseases due to the ability of the spores to survive cooking procedures. It is also associated with local sepsis and wound and systemic infection (See e.g., Drobniewski, Clin. Micro. Rev. 6:324 (1993)). Many bacteria readily develop resistance to antibiotics. An subject infected with an antibiotic-resistant strain of bacteria faces serious and potentially life-threatening consequences.

SUMMARY OF THE INVENTION

The present invention relates to methods and compositions for stimulating an immune response. Specifically, the present invention provides methods of inducing an immune response to bacteria of the genus *Bacillus* (e.g., *Bacillus anthracis*) in a subject (e.g., a human subject) and compositions useful in such methods (e.g., a nanoemulsion comprising *Bacillus anthracis* or an immunogenic portion thereof). Compositions and methods of the present invention find use in, among other things, clinical (e.g. therapeutic and preventative medicine (e.g., vaccination)) and research applications.

Accordingly, in some embodiments, the present invention provides a method of inducing an immune response to *B. anthracis* in a subject comprising providing a composition comprising a nanoemulsion and an immunogen, wherein the immunogen comprises a *B. anthracis* immunogen (e.g., recombinant protective antigen (rPA) of *B. anthracis*); and administering the composition to the subject under conditions such that the subject generates an immune response to *B. anthracis*. The present invention is not limited by the *B. anthracis* immunogen utilized. For example, in some embodiments, the immunogen is an isolated, purified or recombinant protein or peptide antigen, or derivative or variant thereof, selected from the group comprising, but not limited to, protective antigen (PA), lethal factor (LF), edema factor (EF), and PA degradation products. In some embodiments, the immunogen comprises *B. anthracis* inactivated by the nanoemulsion. The present invention is not limited by the nature of the immune response generated. Indeed, a variety of immune responses may be generated and measured in a subject administered a composition comprising a nanoemulsion and an immunogen of the present invention including, but not limited to, activation, proliferation or differentiation of cells of the immune system (e.g., B cells, T cells, dendritic cells, antigen presenting cells (APCs), macrophages, natural killer (NK) cells, etc.); up-regulated or down-regulated expression of markers and cytokines; stimulation of IgA, IgM, or IgG titer; splenomegaly (e.g., increased spleen cellularity); hyperplasia, mixed cellular infiltrates in various organs, and other responses (e.g., of cells) of the immune system that can be assessed with respect to immune stimulation known in the art. In some embodiments, administering comprises contacting a mucosal surface of the subject with the composition. The present invention is not limited by the mucosal surface contacted. In some preferred embodiments, the mucosal surface comprises nasal mucosa. In some embodiments, administrating comprises parenteral administration. The present invention is not limited by the route chosen for administration of a composition of the present invention. In some embodiments, inducing an immune response induces immunity to *B. anthracis* in the subject. In some embodiments, the immunity comprises systemic immunity. In some embodiments, the immunity comprises mucosal immunity.

In some embodiments, the immune response comprises increased expression of IFN-γ in the subject. In some embodiments, the immune response comprises a systemic IgG response. In some embodiments, the immune response comprises a mucosal IgA response. In some embodiments, the composition comprises between 1 and 300 μg of rPA. However, the present invention is not limited to this amount of recombinant protective antigen administered. For example, in some embodiments, more than 300 μg of rPA is present in a dose administered to the subject. In some embodiments, less than 1 μg of rPA is present in a dose administered to a subject. In some embodiments, the composition comprises a 10% nanoemulsion solution. However, the present invention is not limited to this amount (e.g., percentage) of nanoemulsion. For example, in some embodiments, a composition comprises less than 10% nanoemulsion. In some embodiments, a composition comprises more than 10% nanoemulsion. In some embodiments, a composition of the present invention comprises any of the nanoemulsions described herein. In some embodiments, the nanoemulsion comprises $W_{20}5EC$. The present invention is not limited by the type of nanoemulsion utilized. Indeed, a variety of nanoemulsions are contemplated to be useful in the present invention. For example, in some preferred embodiments, the nanoemulsion (e.g., for generating an immune response (e.g., for use as a vaccine)) comprises an oil-in-water emulsion, the oil-in-water emulsion comprising a discontinuous oil phase distributed in an aqueous phase, a first component comprising a solvent (e.g., an alcohol or glycerol), and a second component comprising a surfactant or a halogen-containing compound. The aqueous phase can comprise any type of aqueous phase including, but not limited to, water (e.g., $diH_2O$, distilled water, tap water) and solutions (e.g., phosphate buffered saline solution). The oil phase can comprise any type of oil including, but not limited to, plant oils (e.g., soybean oil, avocado oil, flaxseed oil, coconut oil, cottonseed oil, squalene oil, olive oil, canola oil, corn oil, rapeseed oil, safflower oil, and sunflower oil), animal oils (e.g., fish oil), flavor oil, water insoluble vitamins, mineral oil, and motor oil. In some preferred embodiments, the oil phase comprises 30-90 vol % of the oil-in-water emulsion (i.e., constitutes 30-90% of the total volume of the final emulsion), more preferably 50-80%. While the present invention in not limited by the nature of the alcohol component, in some preferred embodiments, the alcohol is ethanol or methanol. Furthermore, while the present invention is not limited by the nature of the surfactant, in some preferred embodiments, the surfactant is a polysorbate surfactant (e.g., TWEEN 20, TWEEN 40, TWEEN 60, and TWEEN 80), a pheoxypolyethoxyethanol (e.g., TRITON X-100, X-301, X-165, X-102, and X-200, and TYLOXAPOL) or sodium dodecyl sulfate. Likewise, while the present invention is not limited by the nature of the halogen-containing compound, in some preferred embodiments, the halogen-containing compound comprises a cetylpyridinium halides, cetyltrimethylammonium halides, cetyldimethylethylammonium halides, cetyldimethylbenzylammonium halides, cetyltributylphosphonium halides, dodecyltrimethylammonium halides, tetradecyltrimethylammonium halides, cetylpyridinium chloride, cetyltrimethylammonium chloride, cetylbenzyldimethylammonium chloride, cetylpyridinium bromide, cetyltrimethylammonium bromide, cetyidimethylethylammonium bromide, cetyltributylphosphonium bromide, dodecyltrimethylammonium bromide, or tetrad ecyltrimethylammonium bromide. Nanoemulsions of the present invention may further comprise third, fourth, fifth, etc. components. In some preferred embodiments, an additional component is a surfactant (e.g., a second surfactant), a germination enhancer, a phosphate based solvent (e.g., tributyl phosphate), a neutramingen, L-alanine, ammonium chloride, trypticase soy broth, yeast extract, L-ascorbic acid, lecithin, p-hyroxybenzoic acid methyl ester, sodium thiosulate, sodium citrate, inosine, sodium hydroxide, dextrose, and polyethylene glycol (e.g., PEG 200, PEG 2000, etc.). In some embodiments, the oil-in-water emulsion comprises a quaternary ammonium compound. In some preferred embodiments, the oil-in-water emulsion has no detectable toxicity to plants or animals (e.g., to humans). In other preferred embodiments, the oil-in-water emulsion causes no detectable irritation to plants or animals (e.g., to humans). In some embodiments, the oil-in-water emulsion further comprises any of the components described above. Quaternary ammonium compounds include, but are not limited to, N-alkyldimethyl benzyl ammonium saccharinate, 1,3,5-Triazine-1,3,5(2H, 4H,6H)-triethanol; 1-Decanaminium, N-decyl-N, N-dimethyl-, chloride (or) Didecyl dimethyl ammonium chloride; 2-(2-(p-(Diisobuyl)cresosxy)ethoxy)ethyl dimethyl benzyl ammonium chloride; 2-(2-(p-(Diisobutyl)phenoxy)ethoxy) ethyl dimethyl benzyl ammonium chloride; alkyl 1 or 3 benzyl-1-(2-hydroxyethyl)-2-imidazolinium chloride; alkyl bis(2-hydroxyethyl)benzyl ammonium chloride; alkyl demethyl benzyl ammonium chloride; alkyl dimethyl 3,4-dichlorobenzyl ammonium chloride (100% C12); alkyl dimethyl 3,4-dichlorobenzyl ammonium chloride (50% C14, 40% C12, 10% C16); alkyl dimethyl 3,4-dichlorobenzyl ammonium chloride (55% C14, 23% C12, 20% C16); alkyl dimethyl benzyl ammonium chloride; alkyl dimethyl benzyl ammonium chloride (100% C14); alkyl dimethyl benzyl ammonium chloride (100% C16); alkyl dimethyl benzyl ammonium chloride (41% C14, 28% C12); alkyl dimethyl benzyl ammonium chloride (47% C12, 18% C14); alkyl dimethyl benzyl ammonium chloride (55% C16, 20% C14); alkyl dimethyl benzyl ammonium chloride (58% C14, 28% C16); alkyl dimethyl benzyl ammonium chloride (60% C14, 25% C12); alkyl dimethyl benzyl ammonium chloride (61% C11, 23% C14); alkyl dimethyl benzyl ammonium chloride (61% C12, 23% C14); alkyl dimethyl benzyl ammonium chloride (65% C12, 25% C14); alkyl dimethyl benzyl ammonium chloride (67% C12, 24% C14); alkyl dimethyl benzyl ammonium chloride (67% C12, 25% C14); alkyl dimethyl benzyl ammonium chloride (90% C14, 5% C12); alkyl dimethyl benzyl ammonium chloride (93% C14, 4% C12); alkyl dimethyl benzyl ammonium chloride (95% C16, 5% C18); alkyl dimethyl benzyl ammonium chloride (and) didecyl dimethyl ammonium chloride; alkyl dimethyl benzyl ammonium chloride (as in fatty acids); alkyl dimethyl benzyl ammonium chloride (C12-C16); alkyl dimethyl benzyl ammonium chloride (C12-C18); alkyl dimethyl benzyl and dialkyl dimethyl ammonium chloride; alkyl dimethyl dimethylbenzyl ammonium chloride; alkyl dimethyl ethyl ammonium bromide (90% C14, 5% C16, 5% C12); alkyl dimethyl ethyl ammonium bromide (mixed alkyl and alkenyl groups as in the fatty acids of soybean oil); alkyl dimethyl ethylbenzyl ammonium chloride; alkyl dimethyl ethylbenzyl ammonium chloride (60% C14); alkyl dimethyl isoproylbenzyl ammonium chloride (50% C12, 30% C14, 17% C16, 3% C18); alkyl trimethyl ammonium chloride (58% C18, 40% C16, 1% C14, 1% C12); alkyl trimethyl ammonium chloride (90% C18, 10% C16); alkyldimethyl (ethylbenzyl) ammonium chloride (C12-18); Di-(C8-10)-alkyl dimethyl ammonium chlorides; dialkyl dimethyl ammonium chloride; dialkyl dimethyl ammonium chloride; dialkyl dimethyl ammonium chloride; dialkyl methyl benzyl ammonium chloride; didecyl dimethyl ammonium chloride; diisodecyl dimethyl ammonium chloride; dioctyl dimethyl ammonium chloride; dodecyl bis(2-hydroxyethyl)octyl hydrogen ammonium chloride; dodecyl dimethyl benzyl ammonium chloride; dodecylcarbamoyl methyl dimethyl benzyl ammonium chloride; heptadecyl hydroxyethylimidazolinium chloride; hexahydro-1,3,5-thris(2-hydroxyethyl)-s-triazine; myristalkonium chloride (and) Quat RNIUM 14; N,N-Dimethyl-2-hydroxypropylammonium chloride polymer; n-alkyl dimethyl benzyl ammonium chloride; n-alkyl dimethyl ethylbenzyl ammonium chloride; n-tetradecyl dimethyl benzyl ammonium chloride monohydrate; octyl decyl dimethyl ammonium chloride; octyl dodecyl dimethyl ammonium chloride; octyphenoxyethoxyethyl dimethyl benzyl ammonium chloride; oxydiethylenebis(alkyl dimethyl ammonium chloride); quaternary ammonium compounds, dicoco alkyldimethyl, chloride; trimethoxysily propyl dimethyl octadecyl ammonium chloride; trimethoxysilyl quats, trimethyl dodecylbenzyl ammonium chloride; n-dodecyl dimethyl ethylbenzyl ammonium chloride; n-hexadecyl dimethyl benzyl ammonium chloride; n-tetradecyl dimethyl benzyl ammonium chloride; n-tetradecyl dimethyl ethyylbenzyl ammonium chloride; and n-octadecyl dimethyl benzyl ammonium chloride. In some embodiments, the emulsion lacks any antimicrobial substances (i.e., the only antimicrobial composition is the emulsion itself). In some embodiments, the nanoemulsion is X8P. In some embodiments, the immunity protects the subject from displaying signs or symptoms of disease caused by B. anthracis. In some embodiments, the immunity protects the subject from challenge with a subsequent exposure to live B. anthracis. In some embodiments, induction of an immune response protects a subject from morbidity and/or mortality associated with B. anthracis infection. In some embodiments, the composition further comprises an adjuvant. The present invention is not limited by the type of adjuvant utilized. In some embodiments, the adjuvant is a CpG oligonucleotide. A number of other adjuvants that find use in the present invention are described herein. In some embodiments, the subject is a human. In some preferred embodiments, immunity protects said subject from displaying signs or symptoms of anthrax.

The present invention also provides a composition for stimulating an immune response comprising a nanoemulsion and recombinant protective antigen of B. anthracis, wherein the composition is configured to induce immunity to B. anthracis in a subject. In some embodiments, the nanoemulsion comprises $W_{20}5EC$. In some embodiments, the composition provides the subject between 25 and 75 µg of the recombinant protective antigen when administered to the subject. In some embodiments, a dose of the composition administered to the subject comprises a 1% nanoemulsion solution. In some embodiments, the recombinant protective antigen is heat stable in the nanoemulsion. In some embodiments, the recombinant protective antigen is stable for greater than four weeks in the nanoemulsion. In some embodiments, the composition is diluted prior to administration to a subject. In some embodiments, the subject is a human. In some embodiments, the immunity is systemic immunity. In some embodiments, the immunity is mucosal immunity. In some embodiments, the composition further comprises an adjuvant. In some embodiments, the adjuvant comprises a CpG oligonucleotide.

The present invention also provides a kit comprising a composition for stimulating an immune response comprising a nanoemulsion and recombinant protective antigen of B. anthracis, wherein the composition is configured to induce immunity to B. anthracis in a subject, and instructions for administering the composition. In some embodiments, the kit further comprises a device for administering the composition. The present invention is not limited by the type of device utilized for administering the composition. Indeed, a variety of devices are contemplated to be useful in a kit including, but not limited to, a nasal applicator, a syringe, a nasal inhaler and a nasal mister. In some embodiments, the kit comprises a composition comprising a nanoemulsion and a B. anthracis immunogen in contact with a device (e.g., a applicator). In some embodiments, the present invention provides systems and methods for large scale administration (e.g., to a population of a town, village, city, state or country) of a composition of the present invention (e.g., in response to an attack using a Bacillus pathogen).

DESCRIPTION OF THE DRAWINGS

FIG. 3 shows time course of the serum anti-PA IgG in mice. Mice were intranasally immunized with two doses of vaccine (arrows). (A) Induction of the anti-PA IgG in CBA/J mice vaccinated with 20 µg rPA and increasing concentration of NE. (A, insert). The anti-PA IgG subtypes in CBA/J mice immunized with rPA/NE. Data are presented as ratios of individual IgG2a, IgG2b and IgG3 titers versus IgG1 titer. (B) Anti-PA IgG in Balb/c mice vaccinated with various formulations of rPA vaccine. The results are presented as the mean+/−sem of individual serum anti-PA IgG endpoint titers. (*) Indicates statistical difference between the titer achieved with rPA/NE vaccination and the antibody titers in the other groups (p<0.05). (B, insert) Documentation of anti-PA IgE in mice immunized with rPA/Alu. Immuno-dot-blot of 1:10 to 1:80 dilutions of pooled sera from mice immunized with rPA/NE (1), rPA/MPL A (2), rPA/CpG (3), control (4) and rPA/Alu (5).

DEFINITIONS

Figure 1:
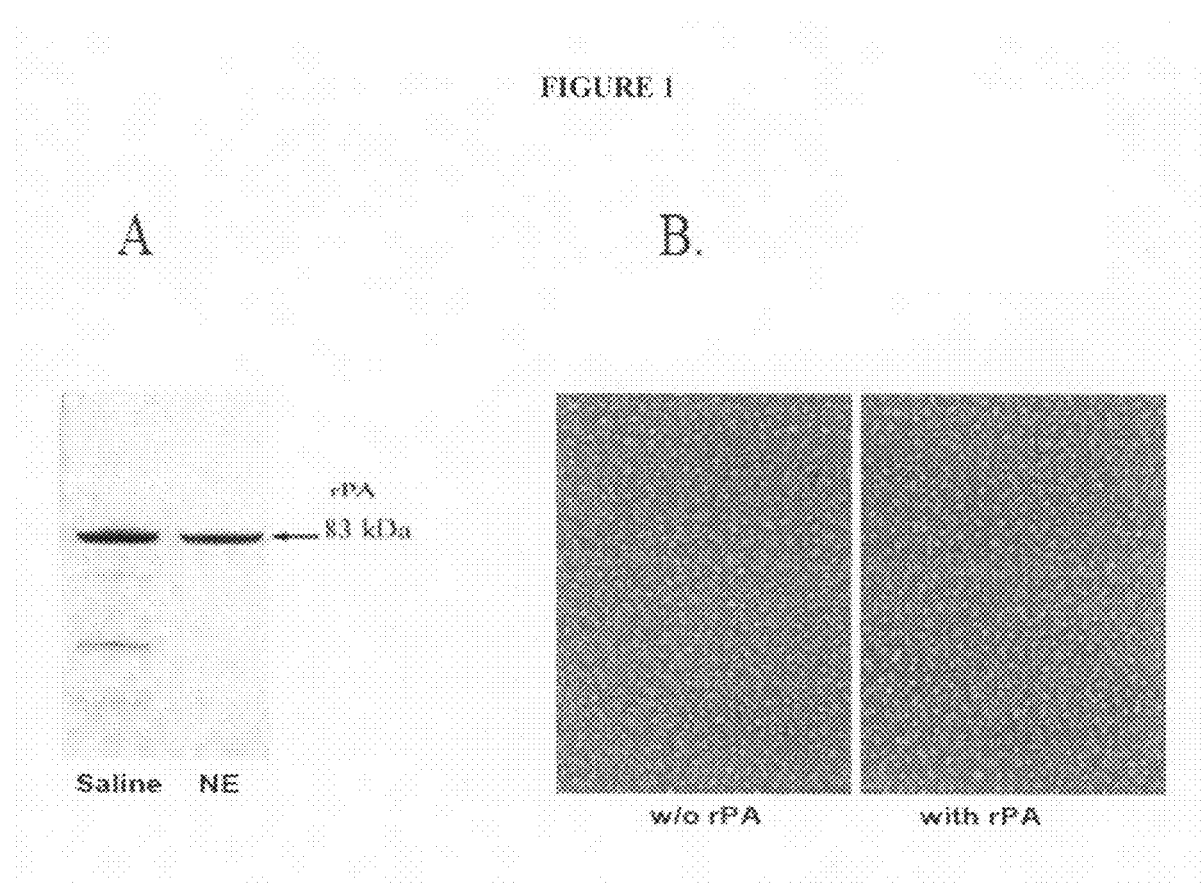
FIG. 1 shows the stability of vaccine preparation. (A) 0.5 µg of rPA protein was incubated 24 hours in saline and 1% NE at room temperature and analyzed using non-reducing 10% PAGE. Silver staining demonstrated low molecular weight fragments after incubation of the antigen without nanoemulsion (saline). (B) Micrographs of the NE and rPA/NE mix show no alteration in the emulsion after mixing with antigen (400× magnification).

To facilitate an understanding of the present invention, a number of terms and phrases are defined below:

As used herein, the term "microorganism" refers to any species or type of microorganism, including but not limited to, bacteria, viruses, archaea, fungi, protozoans, mycoplasma, prions, and parasitic organisms. The term microorganism encompasses both those organisms that are in and of themselves pathogenic to another organism (e.g., animals, including humans, and plants) and those organisms that produce agents that are pathogenic to another organism, while the organism itself is not directly pathogenic or infective to the other organism.

As used herein the term "pathogen," and grammatical equivalents, refers to an organism (e.g., biological agent), including microorganisms, that causes a disease state (e.g., infection, pathologic condition, disease, etc.) in another organism (e.g., animals and plants) by directly infecting the other organism, or by producing agents that causes disease in another organism (e.g., bacteria that produce pathogenic toxins and the like). "Pathogens" include, but are not limited to, viruses, bacteria, archaea, fungi, protozoans, mycoplasma, prions, and parasitic organisms.

The terms "bacteria" and "bacterium" refer to all prokaryotic organisms, including those within all of the phyla in the Kingdom Procaryotae. It is intended that the term encompass all microorganisms considered to be bacteria including *Mycoplasma, Chlamydia, Actinomyces, Streptomyces,* and *Rickettsia*. All forms of bacteria are included within this definition including cocci, bacilli, spirochetes, spheroplasts, protoplasts, etc.

As used herein, the term "fungi" is used in reference to eukaryotic organisms such as molds and yeasts, including dimorphic fungi.

As used herein the terms "disease" and "pathologic condition" are used interchangeably, unless indicated otherwise herein, to describe a deviation from the condition regarded as normal or average for members of a species or group (e.g., humans), and which is detrimental to an affected individual under conditions that are not inimical to the majority of individuals of that species or group. Such a deviation can manifest as a state, signs, and/or symptoms (e.g., diarrhea, nausea, fever, pain, blisters, boils, rash, immune suppression, inflammation, etc.) that are associated with any impairment of the normal state of a subject or of any of its organs or tissues that interrupts or modifies the performance of normal functions. A disease or pathological condition may be caused by or result from contact with a microorganism (e.g., a pathogen or other infective agent (e.g., a virus or bacteria)), may be responsive to environmental factors (e.g., malnutrition, industrial hazards, and/or climate), may be responsive to an inherent defect of the organism (e.g., genetic anomalies) or to combinations of these and other factors.

The terms "host" or "subject," as used herein, refer to an individual to be treated by (e.g., administered) the compositions and methods of the present invention. Subjects include, but are not limited to, mammals (e.g., murines, simians, equines, bovines, porcines, canines, felines, and the like), and most preferably includes humans. In the context of the invention, the term "subject" generally refers to an individual who will be administered or who has been administered one or more compositions of the present invention (e.g., a composition for inducing an immune response).

As used herein, the terms "inactivating," "inactivation" and grammatical equivalents, when used in reference to a microorganism (e.g., a pathogen (e.g., bacteria of the genus *Bacillus* (e.g., *B. anthracis*))), refer to the killing, elimination, neutralization and/or reducing of the capacity of the microorganism to infect and/or cause a pathological response and/or disease in a host. In some preferred embodiments, the present invention provides a composition comprising nanoemulsion (NE)-inactivated bacteria of the genus *Bacillus* (e.g., *B. anthracis*). Accordingly, as referred to herein, compositions comprising "NE-inactivated *Bacillus*," "NE-killed *Bacillus*," NE-neutralized *Bacillus*" or grammatical equivalents refer to compositions that, when administered to a subject, are characterized by the absence of, or significantly reduced presence of, *Bacillus* growth, replication and/or sporulation (e.g., over a period of time (e.g., over a period of days, weeks, months, or longer)) within the host.

As used herein, the term "fusigenic" is intended to refer to an emulsion that is capable of fusing with the membrane of a microbial agent (e.g., a bacterium or bacterial spore). Specific examples of fusigenic emulsions are described herein.

As used herein, the term "lysogenic" refers to an emulsion (e.g., a nanoemulsion) that is capable of disrupting the membrane of a microbial agent (e.g., a virus (e.g., viral envelope) or a bacterium or bacterial spore). In preferred embodiments of the present invention, the presence of a lysogenic and a fusigenic agent in the same composition produces an enhanced inactivating effect compared to either agent alone. Methods and compositions (e.g., for inducing an immune response (e.g., used as a vaccine) using this improved antimicrobial composition are described in detail herein.

The term "emulsion," as used herein, includes classic oil-in-water or water in oil dispersions or droplets, as well as other lipid structures that can form as a result of hydrophobic forces that drive apolar residues (e.g., long hydrocarbon chains) away from water and drive polar head groups toward water, when a water immiscible oily phase is mixed with an aqueous phase. These other lipid structures include, but are not limited to, unilamellar, paucilamellar, and multilamellar lipid vesicles, micelles, and lamellar phases. Similarly, the term "nanoemulsion," as used herein, refers to oil-in-water dispersions comprising small lipid structures. For example, in preferred embodiments, the nanoemulsions comprise an oil phase having droplets with a mean particle size of approximately 0.1 to 5 microns (e.g., 150+/−25 nm in diameter), although smaller and larger particle sizes are contemplated. The terms "emulsion" and "nanoemulsion" are often used herein, interchangeably, to refer to the nanoemulsions of the present invention.

As used herein, the terms "contact," "contacted," "expose," and "exposed," when used in reference to a nanoemulsion and a live microorganism, refer to bringing one or more nanoemulsions into contact with a microorganism (e.g., a pathogen) such that the nanoemulsion inactivates the microorganism or pathogenic agent, if present. The present invention is not limited by the amount or type of nanoemulsion used for microorganism inactivation. A variety of nanoemulsion that find use in the present invention are described herein and elsewhere (e.g., nanoemulsions described in U.S. Pat. Apps. 20020045667 and 20040043041, and U.S. Pat. Nos. 6,015,832, 6,506,803, 6,635,676, and 6,559,189, each of which is incorporated herein by reference in its entirety for all purposes). Ratios and amounts of nanoemulsion (e.g., sufficient for inactivating the microorganism (e.g., virus inactivation)) and microorganisms (e.g., sufficient to provide an antigenic composition (e.g., a composition capable of inducing an immune response)) are contemplated in the present invention including, but not limited to, those described herein (e.g., in Example 1).

The term "surfactant" refers to any molecule having both a polar head group, which energetically prefers solvation by water, and a hydrophobic tail that is not well solvated by water. The term "cationic surfactant" refers to a surfactant with a cationic head group. The term "anionic surfactant" refers to a surfactant with an anionic head group.

The terms "Hydrophile-Lipophile Balance Index Number" and "HLB Index Number" refer to an index for correlating the chemical structure of surfactant molecules with their surface activity. The HLB Index Number may be calculated by a variety of empirical formulas as described, for example, by Meyers, (See, e.g., Meyers, *Surfactant Science and Technology*, VCH Publishers Inc., New York, pp. 231-245 (1992)), incorporated herein by reference. As used herein where appropriate, the HLB Index Number of a surfactant is the HLB Index Number assigned to that surfactant in McCutcheon's Volume 1: Emulsifiers and Detergents North American Edition, 1996 (incorporated herein by reference). The HLB Index Number ranges from 0 to about 70 or more for commercial surfactants. Hydrophilic surfactants with high solubility in water and solubilizing properties are at the high end of the scale, while surfactants with low solubility in water that are good solubilizers of water in oils are at the low end of the scale.

As used herein the term "interaction enhancers" refers to compounds that act to enhance the interaction of an emulsion with a microorganism (e.g., with a cell wall of a bacteria (e.g., a Gram negative bacteria) or with a viral envelope (e.g., Vaccinia virus envelope)). Contemplated interaction enhancers include, but are not limited to, chelating agents (e.g., ethylenediaminetetraacetic acid (EDTA), ethylenebis(oxyethylenenitrilo)tetraacetic acid (EGTA), and the like) and certain biological agents (e.g., bovine serum abulmin (BSA) and the like).

The terms "buffer" or "buffering agents" refer to materials, that when added to a solution, cause the solution to resist changes in pH.

The terms "reducing agent" and "electron donor" refer to a material that donates electrons to a second material to reduce the oxidation state of one or more of the second material's atoms.

The term "monovalent salt" refers to any salt in which the metal (e.g., Na, K, or Li) has a net 1+ charge in solution (i.e., one more proton than electron).

The term "divalent salt" refers to any salt in which a metal (e.g., Mg, Ca, or Sr) has a net 2+ charge in solution.

The terms "chelator" or "chelating agent" refer to any materials having more than one atom with a lone pair of electrons that are available to bond to a metal ion.

The term "solution" refers to an aqueous or non-aqueous mixture.

As used herein, the term "a composition for inducing an immune response" refers to a composition that, once administered to a subject (e.g., once, twice, three times or more (e.g., separated by weeks, months or years)), stimulates, generates and/or elicits an immune response in the subject (e.g., resulting in total or partial immunity to a microorganism (e.g., pathogen) capable of causing disease). In preferred embodiments of the invention, the composition comprises a nanoemulsion and an immunogen (e.g., wherein the immunogen comprises bacterial of the genus *Bacillus* (e.g., *B. anthracis*) inactivated by the nanoemulsion, or, one or more *Bacillus* antigens (e.g., purified (e.g., synthetic, recombinant (e.g., recombinant protective antigen (rPA), or otherwise isolated) proteins or derivatives or analogues thereof). In further preferred embodiments, the composition comprising a nanoemulsion and an immunogen comprises one or more other compounds or agents including, but not limited to, therapeutic agents, physiologically tolerable liquids, gels, carriers, diluents, adjuvants, excipients, salicylates, steroids, immunosuppressants, immunostimulants, antibodies, cytokines, antibiotics, binders, fillers, preservatives, stabilizing agents, emulsifiers, and/or buffers. An immune response may be an innate (e.g., a non-specific) immune response or a learned (e.g., acquired) immune response (e.g. that decreases the infectivity, morbidity, or onset of mortality in a subject (e.g., caused by exposure to a pathogenic microorganism) or that prevents infectivity, pathology, morbidity, or onset of mortality in a subject (e.g., caused by exposure to a pathogenic microorganism)). Thus, in some preferred embodiments, a composition comprising a nanoemulsion and an immunogen (e.g., rPA) is administered to a subject as a vaccine (e.g., to prevent or attenuate a disease (e.g., by providing to the subject total or partial immunity against the disease or the total or partial attenuation (e.g., suppression) of a sign, symptom or condition of the disease)).

As used herein, the term "adjuvant" refers to any substance that can stimulate an immune response. Some adjuvants can cause activation of a cell of the immune system (e.g., an adjuvant can cause an immune cell to produce and secrete a cytokine).

As used herein, the terms "an amount effective to induce an immune response" and "effective amount" (e.g., of a composition for inducing an immune response), refers to the dosage level required (e.g., when administered to a subject) to stimulate, generate and/or elicit an immune response in the subject. An effective amount can be administered in one or more administrations (e.g., via the same or different route), applications or dosages and is not intended to be limited to a particular formulation or administration route.

As used herein, the term "under conditions such that said subject generates an immune response" refers to any condition that leads to a qualitative or quantitative induction, generation, and/or stimulation of an immune response (e.g., innate or acquired).

A used herein, the term "immune response" refers to any detectable response by the immune system of a subject. For example, immune responses include, but are not limited to, an alteration (e.g., increase) in Toll receptor activation, lymphokine (e.g., cytokine (e.g., Th1 or Th2 type cytokines) or chemokine) expression and/or secretion, macrophage activation, dendritic cell activation, T cell (e.g., CD4+ or CD8+ T cell) activation, NK cell activation, and/or B cell activation (e.g., antibody generation and/or secretion). Additional examples of immune responses include binding of an immunogen (e.g., antigen (e.g., immunogenic polypeptide)) to an MHC molecule and induction of a cytotoxic T lymphocyte ("CTL") response, induction of a B cell response (e.g., antibody production), and/or T-helper lymphocyte response, and/or a delayed type hypersensitivity (DTH) response (e.g., against the antigen from which an immunogenic polypeptide is derived), expansion (e.g., growth of a population of cells) of cells of the immune system (e.g., T cells, B cells (e.g., of any stage of development (e.g., plasma cells), and increased processing and presentation of antigen by antigen presenting cells. An immune response may be to immunogens that the subject's immune system recognizes as foreign (e.g., non-self antigens from microorganisms (e.g., pathogens), or self-antigens recognized as foreign). Thus, it is to be understood that, as used herein, "immune response" refers to any type of immune response, including, but not limited to, innate immune responses (e.g., activation of Toll receptor signaling cascade) cell-mediated immune responses (e.g., responses mediated by T cells (e.g., antigen-specific T cells) and non-specific cells of the immune system) and humoral immune responses (e.g., responses mediated by B cells (e.g., via generation and secretion of antibodies into the plasma, lymph, and/or tissue fluids). The term "immune response" is meant to encompass all aspects of the capability of a subject's immune system to respond to an antigen and/or immunogen (e.g., both the initial response to an immunogen (e.g., a pathogen) as well as acquired (e.g., memory) responses that are a result of an adaptive immune response).

As used herein, the term "immunity" refers to protection from disease (e.g., preventing or attenuating (e.g., suppression of) a sign, symptom or condition of the disease) upon exposure to a microorganism (e.g., pathogen) capable of causing the disease. Immunity can be innate (e.g., non-adaptive (e.g., non-acquired) immune responses that exist in the absence of a previous exposure to an antigen) and/or acquired (e.g., immune responses that are mediated by B and T cells following a previous exposure to antigen (e.g., that exhibit increased specificity and reactivity to the antigen)).

As used herein, the term "immunogen" refers to an agent (e.g., a microorganism (e.g., bacterium, virus or fungus) or portion thereof (e.g., an antigen (e.g., gp120 or rPA))) that is capable of eliciting an immune response in a subject. In preferred embodiments, immunogens elicit immunity against the immunogen (e.g., microorganism (e.g., pathogen) or portion thereof (e.g., an antigen (e.g., gp120 or rPA))) when administered in combination with a nanoemulsion of the present invention.

As used herein, the term "pathogen product" refers to any component or product derived from a pathogen including, but not limited to, polypeptides, peptides, proteins, nucleic acids, membrane fractions, and polysaccharides.

As used herein, the term "enhanced immunity" refers to an increase in the level of adaptive and/or acquired immunity in a subject to a given immunogen (e.g., microorganism (e.g., pathogen)) following administration of a composition (e.g., composition for inducing an immune response of the present invention) relative to the level of adaptive and/or acquired immunity in a subject that has not been administered the composition (e.g., composition for inducing an immune response of the present invention).

As used herein, the terms "purified" or "to purify" refer to the removal of contaminants or undesired compounds from a sample or composition. As used herein, the term "substantially purified" refers to the removal of from about 70 to 90%, up to 100%, of the contaminants or undesired compounds from a sample or composition.

As used herein, the terms "administration" and "administering" refer to the act of giving a composition of the present invention (e.g., a composition for inducing an immune response (e.g., a composition comprising a nanoemulsion and an immunogen)) to a subject.

As used herein, the terms "co-administration" and "co-administering" refer to the administration of at least two agent(s) (e.g., a composition comprising a nanoemulsion and an immunogen and one or more other agents—e.g., an adjuvant) or therapies to a subject. In some embodiments, the co-administration of two or more agents or therapies is concurrent. In other embodiments, a first agent/therapy is administered prior to a second agent/therapy. In some embodiments, co-administration can be via the same or different route of administration. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent (s), and/or when co-administration of two or more agents results in sensitization of a subject to beneficial effects of one of the agents via co-administration of the other agent. In other embodiments, co-administration is preferable to elicit an immune response in a subject to two or more different immunogens (e.g., microorganisms (e.g., pathogens)) at or near the same time (e.g., when a subject is unlikely to be available for subsequent administration).

As used herein, the term "topically" refers to application of a compositions of the present invention (e.g., a composition comprising a nanoemulsion and an immunogen) to the surface of the skin and/or mucosal cells and tissues (e.g., alveolar, buccal, lingual, masticatory, vaginal or nasal mucosa, and other tissues and cells which line hollow organs or body cavities).

In some embodiments, the compositions of the present invention are administered in the form of topical emulsions, injectable compositions, ingestible solutions, and the like. When the route is topical, the form may be, for example, a spray (e.g., a nasal spray), a cream, or other viscous solution (e.g., a composition comprising a nanoemulsion and an immunogen in polyethylene glycol).

The terms "pharmaceutically acceptable" or "pharmacologically acceptable," as used herein, refer to compositions that do not substantially produce adverse reactions (e.g., toxic, allergic or pathological reactions) when administered to a subject.

As used herein, the term "pharmaceutically acceptable carrier" refers to any of the standard pharmaceutical carriers including, but not limited to, phosphate buffered saline solution, water, and various types of wetting agents (e.g., sodium lauryl sulfate), any and all solvents, dispersion media, coatings, sodium lauryl sulfate, isotonic and absorption delaying agents, disintigrants (e.g., potato starch or sodium starch glycolate), polyethylethe glycol, and the like. The compositions also can include stabilizers and preservatives. Examples of carriers, stabilizers and adjuvants have been described and are known in the art (See e.g., Martin, Remington's Pharmaceutical Sciences, 15th Ed., Mack Publ. Co., Easton, Pa. (1975), incorporated herein by reference).

As used herein, the term "pharmaceutically acceptable salt" refers to any salt (e.g., obtained by reaction with an acid or a base) of a composition of the present invention that is physiologically tolerated in the target subject. "Salts" of the compositions of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compositions of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

For therapeutic use, salts of the compositions of the present invention are contemplated as being pharmaceutically acceptable. However, salts of acids and bases that are non-pharmaceutically acceptable may also find use, for example, in the preparation or purification of a pharmaceutically acceptable composition.

As used herein, the term "at risk for disease" refers to a subject that is predisposed to experiencing a particular disease. This predisposition may be genetic (e.g., a particular genetic tendency to experience the disease, such as heritable disorders), or due to other factors (e.g., environmental conditions, exposures to detrimental compounds present in the environment, etc.). Thus, it is not intended that the present invention be limited to any particular risk (e.g., a subject may be "at risk for disease" simply by being exposed to and interacting with other people that carry a risk of transmitting a pathogen), nor is it intended that the present invention be limited to any particular disease.

"Nasal application", as used herein, means applied through the nose into the nasal or sinus passages or both. The application may, for example, be done by drops, sprays, mists, coatings or mixtures thereof applied to the nasal and sinus passages.

As used herein, the term "kit" refers to any delivery system for delivering materials. In the context of immunogenic agents (e.g., compositions comprising a nanoemulsion and an immunogen), such delivery systems include systems that allow for the storage, transport, or delivery of immunogenic agents and/or supporting materials (e.g., written instructions for using the materials, etc.) from one location to another. For example, kits include one or more enclosures (e.g., boxes) containing the relevant immunogenic agents (e.g., nanoemulsions) and/or supporting materials. As used herein, the term "fragmented kit" refers to delivery systems comprising two or more separate containers that each contain a subportion of the total kit components. The containers may be delivered to the intended recipient together or separately. For example, a first container may contain a composition comprising a nanoemulsion and an immunogen for a particular use, while a second container contains a second agent (e.g., an antibiotic or spray applicator). Indeed, any delivery system comprising two or more separate containers that each contains a subportion of the total kit components are included in the term "fragmented kit." In contrast, a "combined kit" refers to a delivery system containing all of the components of an immunogenic agent needed for a particular use in a single container (e.g., in a single box housing each of the desired components). The term "kit" includes both fragmented and combined kits.

As used herein, the term "B. anthracis immunogen" refers to a protein or peptide antigen derived from B. anthracis that is capable of generating an immune response in a subject. Examples of B. anthracis immunogens include, but are not limited to, protective antigen (PA), lethal factor (LF), edema factor (EF), and PA degradation products, and antigenic portions thereof. An immunogen may be an isolated wild type or mutant protein, or a recombinant or synthesized protein or peptide antigen or a derivative or variant thereof.

DETAILED DESCRIPTION OF THE INVENTION

The present invention relates to methods and compositions for stimulating an immune response. Specifically, the present invention provides methods of inducing an immune response to bacteria of the genus Bacillus (e.g., Bacillus anthracis) in a subject (e.g., a human subject) and compositions useful in such methods (e.g., a nanoemulsion comprising Bacillus anthracis or an immunogenic portion thereof). Compositions and methods of the present invention find use in, among other things, clinical (e.g. therapeutic and preventative medicine (e.g., vaccination)) and research applications.

Several pathogenic microorganisms initiate infection by attaching to mucosal epithelial cells lining the gastro-intestinal, oropharyngeal, respiratory or genito-urinacy tracts. Some pathogens, such as influenza virus, Bordetella pertussis, or Vibrio cholerae, remain at or within the mucosal tissue, while others, such as Salmonella typhi or hepatitis A virus, possess mechanisms permitting penetration into deeper tissues and spread systemically. Specific and non-specific defense mechanisms of the mucous membranes provide first line protection against both types of pathogen. Non-specific effectors include resident macrophages, antimicrobial peptides, lactoferrin and lysozyme, extremes of pH, bile acids, digestive enzymes, mucus, shedding of epithelial cells, flushing mechanisms (peristalsis, ciliary beating, micturation, etc) and competition from local flora. However, successful pathogens have generally evolved means to survive the non-specific defenses present at the site they infect and it is the secretory immune system which plays a major role in protecting against diseases caused by a number of bacterial and viral pathogens, and is probably a major effector against pathogens that are restricted to mucosal surfaces. For organisms that spread systemically, both local and systemic immune responses are desirable for optimum immunity.

Anthrax is an infectious bacterial disease caused by *Bacillus anthracis*. It occurs most commonly in wild and domestic herbivores (sheep, goats, camels, antelope, cattle, etc.) but may also occur in humans. Infection can occur by cutaneous exposure, by ingestion (gastrointestinal anthrax), or by inhalation (pulmonary anthrax). 95% of anthrax infections in humans occur by cutaneous infection, either from contact with unvaccinated, infected animals in an agricultural setting, or by handling contaminated animal products (meat, leather, hides, hair, wool, etc.) in an industrial setting.

Cutaneous anthrax is fatal in about 20% of cases if untreated, but it can usually be overcome with appropriate antimicrobial therapy. Inhalation or gastrointestinal anthrax infection is much more serious and much more difficult to treat. Inhalation anthrax results in respiratory shock and is fatal in 90%-100% of cases; gastrointestinal anthrax results in severe fever, nausea and vomiting, resulting in death in 25%-75% of cases.

An effective vaccine against anthrax was developed in the United States in the 1950s and 1960s, and a vaccine was approved by the FDA in 1970.

The threat of airborn transmission of anthrax remains at historical highs as *B. anthracis* has been identified as a possible agent for biological warfare. Whereas historically only individuals at high risk, such as veterinarians, livestock handlers, wool shearers, abbatoire workers, etc., needed to consider being vaccinated, the threat to military personnel of the possibility of biological weapons deployment caused the United States military to adopt a sweeping anthrax vaccination program in 1997, under which it was intended to administer the anthrax vaccine to 2.4 million military personnel in all branches of service. (See, e.g., Secretary of Defense, Memorandum for Secretaries of the Military Departments et al., May 18, 1998, Implementation of the Anthrax Vaccination Program for the Total Force).

The only mass produced anthrax vaccine, Anthrax Vaccine Adsorbed (or AVA, commercial name BIOTHRAX), is a noninfectious sterile filtrate of an attenuated strain of *B. anthracis*, adsorbed to aluminum hydroxide (alum) adjuvant, with ≤0.02% formaldehyde and 0.0025% benzethonium chloride added. (See, e.g., Friedlander et al., JAMA, 282(22):2104-2106 (1999)). The course of vaccination consists of six subcutaneous injections of 0.5 mL doses of vaccine over eighteen months, with annual boosters to maintain immunity. This vaccination is believed to provide immunity that is 90%-100% effective against aerosol anthrax challenge, based on animal studies and incidental human data. (See, e.g., Friedlander et al, supra).

While the AVA is moderately effective, the vaccine strain employed, a non-proteolytic, non-capsulated mutant strain of *B. anthracis*, V770-NP1-R, has several disadvantageous characteristics: Despite its mutations, the strain retains a sporogenic and fully toxogenic phenotype, and use of the whole strain in vaccine production results in lot-to-lot variability in levels of protective antigen (PA), as well as inclusion of PA degradation products and other bacterial products (See, e.g., Farchaus, J., et al., Applied & Environmental Microbiol., 64(3):982-991 (1998)). In addition, side effects reported from administration range from the common injection site swelling and tenderness, to systemic reactions (malaise, lassitude, fever, chills) as well as hair loss, muscle aches, chronic fatigue, aching teeth and gums, thick saliva, burn-like skin reactions, rapid weight loss, blackouts, and at least one death. (See, e.g., Chicago Tribune, Mysterious illnesses strike some gulf vets, Mar. 26, 1992, p.2; The Washington Post, The Nation in Brief, Sep. 29, 2000, Section A, p. 34). There exist some who claim the anthrax vaccine is contaminated with squalene (See, e.g., Garret, L., Big Battle Over Vaccine: Detractors Say Immunization for Antrhax Hazardous; Pentagon Says No, The Beacon Journal (Akron), Sunday Jul. 4, 1999, Section B, p. 1), and has resulted in hundreds of military personnel refusing to be vaccinated (See, e.g., Graham, B., Some in Military Fear Anthrax Inoculation Side Effects, The Plain Dealer (Cleveland), Nov. 26, 1998, Section: National, p. 6E; Air Force Reserve Pilots Quitting Due to Vaccine, The Plain Dealer (Cleveland), Feb. 27, 1999, Section: National, p. 6A). Military personnel ranked as high as major have accepted court-martial and dismissal from military service rather than accept the anthrax vaccine. (See, e.g., Eskenazi, M., How Anthrax Causes Early Retirement, TIME.com, Mar. 31, 2000.)

Thus, a great need exists for an improved composition for immunization against anthrax, and other diseases caused by bacteria of the genus *Bacillus*, that is effective to raise an immune response against *B. anthracis*. Such a composition would ideally be formulated without contaminants (e.g., capable of generating unwanted side effects) and would be effective without a need for a long course of vaccination.

Accordingly, the present invention provides methods of inducing an immune response to bacteria of the genus *Bacillus* (e.g., *B. anthracis*) in a subject (e.g., a human subject) and compositions useful in such methods (e.g., a nanoemulsion comprising bacteria or bacterial components (e.g., isolated or recombinant proteins) of the genus *Bacillus* (e.g., *B. anthracis*)). In preferred embodiments, methods of inducing an immune response provided by the present invention are used for vaccination. Due to the rate of adverse events with existing *Bacillus* (e.g., *B. anthracis*) vaccines, the present invention provides a significant improvement in *Bacillus* (e.g., *B. anthracis*) vaccination safety without compromising vaccine efficacy.

For example, the present invention describes the development of immunity (e.g., *B. anthracis* immunity) in a subject after mucosal administration (e.g., mucosal vaccination) with a composition comprising a nanoemulsion and an immunogenic protein from *B. anthracis* (e.g., rPA) generated and characterized during development of the present invention (See Examples 1-9). Nanoemulsion (NE), a surface-active antimicrobial material, was mixed with recombinant protective antigen (rPA), resulting in an immunogenic composition comprising NE and rPA that is stable at room temperature (e.g., in some embodiments, for more than 2 weeks, more preferably more than 3 weeks, even more preferably more than 4 weeks, and most preferably for more than 5 weeks) and that can be used to induce an immune response against *B. anthracis* in a subject (e.g., that can be used either alone or as an adjuvant for inducing an anti-*B. anthracis* immune response).

Mucosal administration of a composition comprising NE and rPA to a subject resulted in high-titer mucosal and systemic antibody responses and specific Th1 cellular immunity (See, e.g., Examples 4-5, 7-9). Further, serum from mice immunized intranasally with a composition comprising NE and rPA was capable of neutralizing binding of PA to its receptor (ATR receptor) (See Example 6). Mice administered two doses and guinea pigs administered just a single dose of a composition comprising NE and rPA developed significant serum concentrations of anti-rPA IgG after administration (See, e.g., Example 4). Moreover, mice administered this composition generated mucosal immune responses (e.g., IgA antibodies toward rPA) (See Example 5).

Thus, in some embodiments, the present invention provides that administration (e.g., mucosal administration) of a composition comprising NE and a *B. anthracis* immunogen (e.g., rPA) is sufficient to induce a protective immune response against *B. anthracis* in a subject (e.g., protective immunity (e.g., mucosal and systemic immunity)). In some embodiments, a subsequent administration (e.g., one or more boost administrations subsequent to a primary administration) to a subject provides the induction of an enhanced immune response to *B. anthracis* in the subject. Thus, the present invention demonstrates that administration of a composition comprising NE and a *B. anthracis* immunogen (e.g., rPA) to a subject provides protective immunity against anthrax (e.g., via a durable anti-PA IgG response).

In contrast, intranasal instillations of NE alone or NE with CpG adjuvant was not able to induce an immune response against *B. anthracis* (See Examples 4-6). Furthermore, administration of rPA alone (e.g., in saline) did not induce significant IgG or IgA antibody production in mice. Although an understanding of the mechanism is not necessary to practice the present invention and the present invention is not limited to any particular mechanism of action, in some embodiments, combining a NE and an immunogenic protein, rPA, from *B. anthracis* stabilizes the rPA (See Example 2) and provides the proper environment for generation of an immune response. In other embodiments, because NE formulations can penetrate the mucosa through pores, they may carry immunogenic proteins to the submucosal location of dendritic cells (e.g., thereby initiating and/or stimulating an immune response). In some embodiments, when a NE is used to inactivate bacteria of the genus *Bacillus* (e.g., *B. anthracis*) combining the bacteria and the NE preserves important immunogenic epitopes (e.g., recognizable by a subject's immune system), stabilizing their hydrophobic and hydrophilic components in the oil and water interface of the emulsion (e.g., thereby providing one or more immunogens (e.g., stabilized antigens) against which a subject can mount an immune response).

Dendritic cells avidly phagocytose NE oil droplets and this could provide a means to internalize immunogenic proteins for antigen presentation. While other vaccines rely on inflammatory toxins or other immune stimuli for adjuvant activity (See, e.g., Holmgren and Czerkinsky, Nature Med. 2005, 11; 45-53), NEs have not been shown to be inflammatory when placed on the skin or mucous membranes in studies on animals and in humans. Thus, although an understanding of the mechanism is not necessary to practice the present invention and the present invention is not limited to any particular mechanism of action, in some embodiments, a composition comprising a NE of the present invention (e.g., a composition comprising NE and one or more *Bacillus* proteins (e.g., rPA) may act as a "physical" adjuvant (e.g., that transports and/or presents *Bacillus* proteins to the immune system (e.g., See Example 3)). In some preferred embodiments, mucosal administration of a composition of the present invention generates mucosal as well as systemic immunity (e.g., signs of mucosal immunity (e.g., generation of IgA antibody titers).

Both cellular and humoral immunity play a role in protection against *Bacillus* (e.g., *B. anthracis*), and both were induced with the NE formulations (See, e.g., Examples 4-9). Thus, in some embodiments, administration (e.g., mucosal administration) of a composition of the present invention to a subject results in the induction of both humoral (e.g., development of specific antibodies) and cellular (e.g., cytotoxic T lymphocyte) immune responses (e.g., against *Bacillus* proteins). In some preferred embodiments, a composition of the present invention (e.g., a composition comprising a NE and *Bacillus* proteins (e.g., rPA)) is used as an anthrax vaccine.

Furthermore, in preferred embodiments, a composition of the present invention induces (e.g., when administered to a subject) both systemic and mucosal immunity. Thus, in some preferred embodiments, administration of a composition of the present invention to a subject results in protection against an exposure (e.g., a lethal mucosal exposure) to *B. anthracis* (See Examples 8 and 9). Although an understanding of the mechanism is not necessary to practice the present invention and the present invention is not limited to any particular mechanism of action, mucosal administration (e.g., vaccination) provides protection against *Bacillus* infection (e.g., that initiates at a mucosal surface). Although it has heretofore proven difficult to stimulate secretory IgA responses and protection against pathogens that invade at mucosal surfaces (See, e.g., Mestecky et al, Mucosal Immunology. 3rd Edn. (Academic Press, San Diego, 2005)), the present invention provides compositions and methods for stimulating mucosal immunity (e.g., a protective IgA response) from a pathogen in a subject.

In some embodiments, the present invention provides a composition (e.g., a composition comprising a NE and a *B. anthracis* immunogen (e.g., rPA)) to serve as a mucosal vaccine. This material can easily be produced (e.g., with NE and recombinant protein (See, e.g., Example 1)), and induces both mucosal and systemic immunity (See, e.g., Examples 4-9). The ability to produce this formulation rapidly and administer it via nasal instillation provides a vaccine that can be used in large-scale outbreaks or emergent situations.

In some preferred embodiments, the present invention provides a composition for generating an immune response comprising a NE and an immunogen (e.g., a purified, isolated or synthetic *Bacillus* protein or derivative or analogue thereof; or, bacteria of the genus *Bacillus* inactivated by the nanoemulsion). When administered to a subject, a composition of the present invention stimulates an immune response against the immunogen within the subject. Although an understanding of the mechanism is not necessary to practice the present invention and the present invention is not limited to any particular mechanism of action, in some embodiments, generation of an immune response (e.g., resulting from administration of a composition comprising a nanoemulsion and a recombinant *Bacillus* protein) provides total or partial immunity to the subject (e.g., from signs, symptoms or conditions of a disease (e.g., anthrax)). Without being bound to any specific theory, protection and/or immunity from disease (e.g., the ability of a subject's immune system to prevent or attenuate (e.g., suppress) a sign, symptom or condition of disease) upon exposure to an immunogenic composition of the present invention is due to adaptive (e.g., acquired) immune responses (e.g., immune responses mediated by B and T cells following exposure to a NE comprising a recombinant *Bacillus* protein of the present invention (e.g., immune responses that exhibit increased specificity and reactivity to *Bacillus*).

In some embodiments, a NE comprising an immunogen (e.g., a recombinant *Bacillus* protein) is administered alone. In some embodiments, a composition comprising a NE and an immunogen (e.g., a recombinant *Bacillus* protein) comprises one or more other agents (e.g., a pharmaceutically acceptable carrier, adjuvant, excipient, and the like). In some embodiments, a composition for stimulating an immune response of the present invention is administered in a manner to induce a humoral immune response. In some embodiments, a composition for stimulating an immune response of the present invention is administered in a manner to induce a cellular (e.g., cytotoxic T lymphocyte) immune response, rather than a humoral response. In some embodiments, a composition comprising a NE and an immunogen of the present invention induces both a cellular and humoral immune response.

The present invention is not limited by the type of NE utilized (e.g., in an immunogenic composition comprising an immunogen). Indeed, a variety of NE compositions are contemplated to be useful in the present invention.

For example, in some embodiments, a nanoemulsion comprises (i) an aqueous phase; (ii) an oil phase; and at least one additional compound. In some embodiments of the present invention, these additional compounds are admixed into either the aqueous or oil phases of the composition. In other embodiments, these additional compounds are admixed into a composition of previously emulsified oil and aqueous phases. In certain of these embodiments, one or more additional compounds are admixed into an existing emulsion composition immediately prior to its use. In other embodiments, one or more additional compounds are admixed into an existing emulsion composition prior to the compositions immediate use.

Additional compounds suitable for use in a nanoemulsion of the present invention include, but are not limited to, one or more organic, and more particularly, organic phosphate based solvents, surfactants and detergents, cationic halogen containing compounds, germination enhancers, interaction enhancers, food additives (e.g., flavorings, sweetners, bulking agents, and the like) and pharmaceutically acceptable compounds. Certain exemplary embodiments of the various compounds contemplated for use in the compositions of the present invention are presented below.

A. Aqueous Phase

In certain preferred embodiments, a nanoemulsion comprises about 5 to 60, preferably 10 to 40, more preferably 15 to 30, vol. % aqueous phase, based on the total volume of the emulsion, although higher and lower amounts are contemplated. In preferred embodiments, the aqueous phase comprises water at a pH of about 4 to 10, preferably about 6 to 8. When the emulsions of the present invention contain a germination enhancer, the pH is preferably 6 to 8. The water is preferably deionized (hereinafter "Di$H_2$O") or distilled. In some embodiments the aqueous phase comprises phosphate buffered saline (PBS). In those embodiments of the present invention intended for administration to, or contact with, a subject (e.g., a subject vaccinated with a composition of the present invention), the aqueous phase, and any additional compounds provided in the aqueous phase, may further be sterile and pyrogen free.

B. Oil Phase and Solvents

In certain preferred embodiments, the oil phase (e.g., carrier oil) of a nanoemulsion comprises 30-90, preferably 60-80, and more preferably 60-70, vol. % of oil, based on the total volume of the emulsion, although higher and lower amounts are contemplated. Suitable oils include, but are not limited to, soybean oil, avocado oil, flaxseed oil, coconut oil, cottonseed oil, squalene oil, olive oil, canola oil, corn oil, rapeseed oil, safflower oil, sunflower oil, pine oil (e.g., 15%), Olestra oil, fish oils, flavor oils, water insoluble vitamins and mixtures thereof. In particularly preferred embodiments, soybean oil is used. Additional contemplated oils include motor oils, mineral oils, and butter. In preferred embodiments of the present invention, the oil phase is preferably distributed throughout the aqueous phase as droplets having a mean particle size in the range from about 1-2 microns, more preferably from 0.2 to 0.8, and most preferably about 0.8 microns. In other embodiments, the aqueous phase can be distributed in the oil phase. In some preferred embodiments, very small droplet sizes are utilized (e.g., less than 0.5 microns) to produce stable nanoemulsion compositions. It is contemplated that small droplet compositions also provide clear solutions, which may find desired use in certain product types.

In some embodiments, the oil phase comprises 3-15, preferably 5-10 vol. % of an organic solvent, based on the total volume of the emulsion, although higher and lower amounts are contemplated. Although an understanding of the mechanism is not necessary to practice the present invention and the present invention is not limited to any particular mechanism of action, it is contemplated that the organic phosphate-based solvents employed in an emulsion serves to disrupt and inactivate the pathogen (e.g., disrupt lipids in membranes or viral envelopes). Thus, any solvent that can remove sterols or phospholipids finds use in the emulsions of the present invention. Suitable organic solvents include, but are not limited to, organic phosphate based solvents or alcohols. In preferred embodiments, the organic phosphate based solvents include, but are not limited to, dialkyl- and trialkyl phosphates (e.g., tri-n-butyl phosphate (TBP)) in any combination. A particularly preferred trialkyl phosphate in certain embodiments comprises tri-n-butyl phosphate, which is a plasticizer. Moreover, in a preferred embodiment, each alkyl group of the di- or trialkyl phosphate has from one to ten or more carbon atoms, more preferably two to eight carbon atoms. The present invention also contemplates that each alkyl group of the di- or trialkyl phosphate may or may not be identical to one another. In certain embodiments, mixtures of different dialkyl and trialkyl phosphates can be employed. In those embodiments comprising one or more alcohols as solvents, such solvents include, but are not limited to, methanol, ethanol, propanol and octanol. In a particularly preferred embodiment, the alcohol is ethanol. In those embodiments of the present invention intended for consumption by, or contact to, a host, the oil phase, and any additional compounds provided in the oil phase, may further be sterile and pyrogen free.

C. Surfactants and Detergents

In some embodiments, a nanoemulsion further comprises one or more surfactants or detergents (e.g., from about 3 to 15%, and preferably about 10%, although higher and lower amounts are contemplated). While the present invention is not limited to any particular mechanism, and an understanding of the mechanism is not required to practice the present invention, it is contemplated that surfactants help to stabilize the compositions (e.g., used to generate an immune response in a subject (e.g., used as a vaccine). Both non-ionic (nonanionic) and ionic surfactants are contemplated. Additionally, surfactants from the BRIJ family of surfactants find use in the compositions of the present invention. The surfactant can be provided in either the aqueous or the oil phase. Surfactants suitable for use with the emulsions include a variety of anionic and nonionic surfactants, as well as other emulsifying compounds that are capable of promoting the formation of oil-in-water emulsions. In general, emulsifying compounds are relatively hydrophilic, and blends of emulsifying compounds can be used to achieve the necessary qualities. In some formulations, nonionic surfactants have advantages over ionic emulsifiers in that they are substantially more compatible with a broad pH range and often form more stable emulsions than do ionic (e.g., soap-type) emulsifiers. Thus, in certain preferred embodiments, a nanoemulsion comprises one or more non-ionic surfactants such as a polysorbate surfactants (e.g., polyoxyethylene ethers), polysorbate detergents, pheoxypolyethoxyethanols, and the like. Examples of polysorbate detergents useful in the present invention include, but are not limited to, TWEEN 20, TWEEN 40, TWEEN 60, TWEEN 80, etc.

TWEEN 60 (polyoxyethylenesorbitan monostearate), together with TWEEN 20, TWEEN 40 and TWEEN 80, comprise polysorbates that are used as emulsifiers in a number of pharmaceutical compositions. In some embodiments of the present invention, these compounds are also used as co-components with adjuvants. TWEEN surfactants also appear to have virucidal effects on lipid-enveloped viruses (See e.g., Eriksson et al., Blood Coagulation and Fibtinolysis 5 (Suppl. 3):S37-S44 (1994)).

Examples of pheoxypolyethoxyethanols, and polymers thereof, useful in the present invention include, but are not limited to, TRITON (e.g., X-100, X-301, X-165, X-102, X-200), and TYLOXAPOL. TRITON X-100 is a strong non-ionic detergent and dispersing agent widely used to extract lipids and proteins from biological structures. It also has virucidal effect against broad spectrum of enveloped viruses (See e.g., Maha and Igarashi, Southeast Asian J. Trop. Med. Pub. Health 28:718 (1997); and Portocala et al., Virologie 27:261 (1976)). Due to this anti-viral activity, it is employed to inactivate viral pathogens in fresh frozen human plasma (See e.g., Horowitz et al., Blood 79:826 (1992)).

In particularly preferred embodiments, the surfactants TRITON X-100 (t-octylphenoxypolyethoxyethanol), and/or TYLOXAPOL are employed. Some other embodiments, employ spermicides (e.g., Nonoxynol-9). Additional surfactants and detergents useful in the compositions of the present invention may be ascertained from reference works (See e.g., McCutheon's Volume 1: Emulsions and Detergents— North American Edition, 2000).

D. Cationic Halogen Containing Compounds

In some embodiments, nanoemulsions (e.g., used in an immunogenic composition of the present invention) further comprise a cationic halogen containing compound (e.g., from about 0.5 to 1.0 wt. % or more, based on the total weight of the emulsion, although higher and lower amounts are contemplated). In preferred embodiments, the cationic halogen-containing compound is preferably premixed with the oil phase; however, it should be understood that the cationic halogen-containing compound may be provided in combination with the emulsion composition in a distinct formulation. Suitable halogen containing compounds may be selected, for example, from compounds comprising chloride, fluoride, bromide and iodide ions. In preferred embodiments, suitable cationic halogen containing compounds include, but are not limited to, cetylpyridinium halides, cetyltrimethylammonium halides, cetyldimethylethylammonium halides, cetyldimethylbenzylammonium halides, cetyltributylphosphonium halides, dodecyltrimethylammonium halides, or tetradecyltrimethylammonium halides. In some particular embodiments, suitable cationic halogen containing compounds comprise, but are not limited to, cetylpyridinium chloride (CPC), cetyltrimethylammonium chloride, cetylbenzyldimethylammonium chloride, cetylpyridinium bromide (CPB), cetyltrimethylammonium bromide (CTAB), cetyidimethylethylammonium bromide, cetyltributylphosphonium bromide, dodecyltrimethylammonium bromide, and tetrad ecyltrimethylammonium bromide. In particularly preferred embodiments, the cationic halogen containing compound is CPC, although the compositions of the present invention are not limited to formulation with an particular cationic containing compound.

E. Germination Enhancers

In other embodiments of the present invention, nanoemulsion compositions further comprise one or more germination enhancing compounds (e.g., from about 1 mM to 15 mM, and more preferably from about 5 mM to 10 mM, although higher and lower amounts are contemplated). In preferred embodiments, the germination enhancing compound is provided in the aqueous phase prior to formation of the emulsion. The present invention contemplates that when germination enhancers are added to the disclosed compositions the sporicidal properties of the compositions are enhanced. The present invention further contemplates that such germination enhancers initiate sporicidal activity near neutral pH (between pH 6-8, and preferably 7). Such neutral pH emulsions can be obtained, for example, by diluting with phosphate buffer saline (PBS) or by preparations of neutral emulsions. The sporicidal activity of the compositions preferentially occurs when the spores initiate germination.

In certain embodiments, suitable germination enhancing agents of the invention include, but are not limited to, α-amino acids comprising glycine and the L-enantiomers of alanine, valine, leucine, isoleucine, serine, threonine, lysine, phenylalanine, tyrosine, and the alkyl esters thereof. Additional information on the effects of amino acids on germination may be found in U.S. Pat. No. 5,510,104, herein incorporated by reference in its entirety. In some embodiments, a mixture of glucose, fructose, asparagine, sodium chloride (NaCl), ammonium chloride ($NH_4Cl$), calcium chloride ($CaCl_2$) and potassium chloride (KCl) also may be used. In particularly preferred embodiments of the present invention, the formulation comprises the germination enhancers L-alanine, $CaCl_2$, Inosine and $NH_4Cl$. In some embodiments, the compositions further comprise one or more common forms of growth media (e.g., trypticase soy broth, and the like) that additionally may or may not itself comprise germination enhancers and buffers.

The above compounds are merely exemplary germination enhancers and it is understood that other known germination enhancers will find use in the compositions of the present invention. A candidate germination enhancer should meet two criteria for inclusion in the compositions of the present invention: it should be capable of being associated with a nanoemulsion and it should increase the rate of germination of a target spore when incorporated in the emulsions of the present invention.

F. Interaction Enhancers

In still other embodiments, a nanoemulsion may comprise one or more compounds capable of increasing the interaction of the nanoemulsion (i.e., "interaction enhancer") with a target pathogen (e.g., with a bacterial membrane or viral envelope). In some embodiments, the interaction enhancer is premixed with the oil phase; however, in other embodiments the interaction enhancer is provided in combination with the compositions after emulsification. In certain preferred embodiments, the interaction enhancer is a chelating agent (e.g., ethylenediaminetetraacetic acid (EDTA) or ethylenebis(oxyethylenenitrilo)tetraacetic acid (EGTA) in a buffer (e.g., tris buffer)). It is understood that chelating agents are merely exemplary interaction enhancing compounds. Indeed, other agents that increase the interaction of a nanoemulsion with a pathogen are contemplated. In particularly preferred embodiments, the interaction enhancer is at a concentration of about 50 to about 250 µM, although higher and lower amounts are contemplated. One skilled in the art will be able to determine whether a particular agent has the desired function of acting as an interaction enhancer by applying such an agent in combination with a nanoemulsion composition of the present invention to a target pathogen and comparing the inactivation of the target when contacted by the admixture with inactivation of like targets by the composition of the present invention without the agent. For example, an agent that increases the interaction and thereby neutralizes (e.g., decreases or inhibits the growth of the pathogen) in comparison to that parameter in its absence is considered an interaction enhancer.

G. Other Components

In some embodiments, a nanoemulsion comprises one or more additional components that provide a desired property or functionality to the nanoemulsions. These components may be incorporated into the aqueous phase or the oil phase of the nanoemulsions and/or may be added prior to or following emulsification. For example, in some embodiments, the nanoemulsions further comprise phenols (e.g., triclosan, phenyl phenol), acidifying agents (e.g., citric acid (e.g., 1.5-6%), acetic acid, lemon juice), alkylating agents (e.g., sodium hydroxide (e.g., 0.3%)), buffers (e.g., citrate buffer, acetate buffer, and other buffers useful to maintain a specific pH), and halogens (e.g., polyvinylpyrrolidone, sodium hypochlorite, hydrogen peroxide).

Exemplary techniques for making a nanoemulsion are described below. Additionally, a number of specific, although exemplary, formulation recipes are also set forth below.

Formulation Techniques

Nanoemulsions of the present invention can be formed using classic emulsion forming techniques. In brief, the oil phase is mixed with the aqueous phase under relatively high shear forces (e.g., using high hydraulic and mechanical forces) to obtain an oil-in-water nanoemulsion. The emulsion is formed by blending the oil phase with an aqueous phase on a volume-to-volume basis ranging from about 1:9 to 5:1, preferably about 5:1 to 3:1, most preferably 4:1, oil phase to aqueous phase. The oil and aqueous phases can be blended using any apparatus capable of producing shear forces sufficient to form an emulsion such as French Presses or high shear mixers (e.g., FDA approved high shear mixers are available, for example, from Admix, Inc., Manchester, N.H.). Methods of producing such emulsions are described in U.S. Pat. Nos. 5,103,497 and 4,895,452, herein incorporated by reference in their entireties.

In preferred embodiments, compositions used in the methods of the present invention comprise droplets of an oily discontinuous phase dispersed in an aqueous continuous phase, such as water. In preferred embodiments, nanoemulsions of the present invention are stable, and do not decompose even after long storage periods (e.g., greater than one or more years). Furthermore, in some embodiments, nanoemulsions are stable (e.g., in some embodiments for greater than 3 months, in some embodiments for greater than 6 months, in some embodiments for greater than 12 months, in some embodiments for greater than 18 months) after combination with an immunogen. In preferred embodiments, nanoemulsions of the present invention are non-toxic and safe when administered (e.g., via spraying or contacting mucosal surfaces, swallowed, inhaled, etc.) to a subject.

In some embodiments, a portion of the emulsion may be in the form of lipid structures including, but not limited to, unilamellar, multilamellar, and paucliamellar lipid vesicles, micelles, and lamellar phases.

Some embodiments of the present invention employ an oil phase containing ethanol. For example, in some embodiments, the emulsions of the present invention contain (i) an aqueous phase and (ii) an oil phase containing ethanol as the organic solvent and optionally a germination enhancer, and (iii) TYLOXAPOL as the surfactant (preferably 2-5%, more preferably 3%). This formulation is highly efficacious for inactivation of pathogens and is also non-irritating and non-toxic to mammalian subjects (e.g., and thus can be used for administration to a mucosal surface).

In some other embodiments, the emulsions of the present invention comprise a first emulsion emulsified within a second emulsion, wherein (a) the first emulsion comprises (i) an aqueous phase; and (ii) an oil phase comprising an oil and an organic solvent; and (iii) a surfactant; and (b) the second emulsion comprises (i) an aqueous phase; and (ii) an oil phase comprising an oil and a cationic containing compound; and (iii) a surfactant.

Exemplary Formulations

The following description provides a number of exemplary emulsions including formulations for compositions BCTP and $X_8W_{60}PC$. BCTP comprises a water-in oil nanoemulsion, in which the oil phase was made from soybean oil, tri-n-butyl phosphate, and TRITON X-100 in 80% water. $X_8W_{60}PC$ comprises a mixture of equal volumes of BCTP with $W_{80}8P$. $W_{80}8P$ is a liposome-like compound made of glycerol monostearate, refined oya sterols (e.g., GENEROL sterols), TWEEN 60, soybean oil, a cationic ion halogen-containing CPC and peppermint oil. The GENEROL family are a group of a polyethoxylated soya sterols (Henkel Corporation, Ambler, Pa.). Exemplary emulsion formulations useful in the present invention are provided in Table 1. These particular formulations may be found in U.S. Pat. No. 5,700,679 (NN); U.S. Pat. Nos. 5,618,840; 5,549,901 ($W_{80}8P$); and 5,547,677, each of which is hereby incorporated by reference in their entireties. Certain other emulsion formulations are presented U.S. patent application Ser. No. 10/669,865, hereby incorporated by reference in its entirety.

The $X_8W_{60}PC$ emulsion is manufactured by first making the $W_{80}8P$ emulsion and BCTP emulsions separately. A mixture of these two emulsions is then re-emulsified to produce a fresh emulsion composition termed $X_8W_{60}PC$. Methods of producing such emulsions are described in U.S. Pat. Nos. 5,103,497 and 4,895,452 (each of which is herein incorporated by reference in their entireties).

TABLE 1

| | Oil Phase Formula | Water to Oil Phase Ratio (Vol/Vol) |
|---|---|---|
| BCTP | 1 vol. Tri(N-butyl)phosphate<br>1 vol. TRITON X-100<br>8 vol. Soybean oil | 4:1 |
| NN | 86.5 g Glycerol monooleate<br>60.1 ml Nonoxynol-9<br>24.2 g GENEROL 122 | 3:1 |

TABLE 1-continued

| Oil Phase Formula | | Water to Oil Phase Ratio (Vol/Vol) |
|---|---|---|
| W$_{80}$8P | 3.27 g Cetylpyridinium chloride<br>554 g Soybean oil<br>86.5 g Glycerol monooleate<br>21.2 g Polysorbate 60<br>24.2 g GENEROL 122<br>3.27 g Cetylpyddinium chloride | 3.2:1 |
| SS | 4 ml Peppermint oil<br>554 g Soybean oil<br>86.5 g Glycerol monooleate<br>21.2 g Polysorbate 60<br>24.2 g GENEROL 122<br>3.27 g Cetylpyridinium chloride<br>554 g Soybean oil | 3.2:1<br>(1% bismuth in water) |

The compositions listed above are only exemplary and those of skill in the art will be able to alter the amounts of the components to arrive at a nanoemulsion composition suitable for the purposes of the present invention. Those skilled in the art will understand that the ratio of oil phase to water as well as the individual oil carrier, surfactant CPC and organic phosphate buffer, components of each composition may vary.

Although certain compositions comprising BCTP have a water to oil ratio of 4:1, it is understood that the BCTP may be formulated to have more or less of a water phase. For example, in some embodiments, there is 3, 4, 5, 6, 7, 8, 9, 10, or more parts of the water phase to each part of the oil phase. The same holds true for the W$_{80}$8P formulation. Similarly, the ratio of Tri(N-butyl)phosphate:TRITON X-100:soybean oil also may be varied.

Although Table 1 lists specific amounts of glycerol monooleate, polysorbate 60, GENEROL 122, cetylpyridinium chloride, and carrier oil for W$_{80}$8P, these are merely exemplary. An emulsion that has the properties of W$_{80}$8P may be formulated that has different concentrations of each of these components or indeed different components that will fulfill the same function. For example, the emulsion may have between about 80 to about 100 g of glycerol monooleate in the initial oil phase. In other embodiments, the emulsion may have between about 15 to about 30 g polysorbate 60 in the initial oil phase. In yet another embodiment the composition may comprise between about 20 to about 30 g of a GENEROL sterol, in the initial oil phase.

Individual components of nanoemulsions (e.g. in an immunogenic composition of the present invention) can function both to inactivate a pathogen as well as to contribute to the non-toxicity of the emulsions. For example, the active component in BCTP, TRITON-X100, shows less ability to inactivate a virus at concentrations equivalent to 11% BCTP. Adding the oil phase to the detergent and solvent markedly reduces the toxicity of these agents in tissue culture at the same concentrations. While not being bound to any theory (an understanding of the mechanism is not necessary to practice the present invention, and the present invention is not limited to any particular mechanism), it is suggested that the nanoemulsion enhances the interaction of its components with the pathogens thereby facilitating the inactivation of the pathogen and reducing the toxicity of the individual components. Furthermore, when all the components of BCTP are combined in one composition but are not in a nanoemulsion structure, the mixture is not as effective at inactivating a pathogen as when the components are in a nanoemulsion structure.

Numerous additional embodiments presented in classes of formulations with like compositions are presented below. The following compositions recite various ratios and mixtures of active components. One skilled in the art will appreciate that the below recited formulation are exemplary and that additional formulations comprising similar percent ranges of the recited components are within the scope of the present invention.

In certain embodiments of the present invention, a nanoemulsion comprises from about 3 to 8 vol. % of TYLOXAPOL, about 8 vol. % of ethanol, about 1 vol. % of cetylpyridinium chloride (CPC), about 60 to 70 vol. % oil (e.g., soybean oil), about 15 to 25 vol. % of aqueous phase (e.g., DiH$_2$O or PBS), and in some formulations less than about 1 vol. % of 1N NaOH. Some of these embodiments comprise PBS. It is contemplated that the addition of 1N NaOH and/or PBS in some of these embodiments, allows the user to advantageously control the pH of the formulations, such that pH ranges from about 7.0 to about 9.0, and more preferably from about 7.1 to 8.5 are achieved. For example, one embodiment of the present invention comprises about 3 vol. % of TYLOXAPOL, about 8 vol. % of ethanol, about 1 vol. % of CPC, about 64 vol. % of soybean oil, and about 24 vol. % of DiH$_2$O (designated herein as Y3EC). Another similar embodiment comprises about 3.5 vol. % of TYLOXAPOL, about 8 vol. % of ethanol, and about 1 vol. % of CPC, about 64 vol. % of soybean oil, and about 23.5 vol. % of DiH$_2$O (designated herein as Y3.5EC). Yet another embodiment comprises about 3 vol. % of TYLOXAPOL, about 8 vol. % of ethanol, about 1 vol. % of CPC, about 0.067 vol. % of 1N NaOH, such that the pH of the formulation is about 7.1, about 64 vol. % of soybean oil, and about 23.93 vol. % of DiH$_2$O (designated herein as Y3EC pH 7.1). Still another embodiment comprises about 3 vol. % of TYLOXAPOL, about 8 vol. % of ethanol, about 1 vol. % of CPC, about 0.67 vol. % of 1N NaOH, such that the pH of the formulation is about 8.5, and about 64 vol. % of soybean oil, and about 23.33 vol. % of DiH$_2$O (designated herein as Y3EC pH 8.5). Another similar embodiment comprises about 4% TYLOXAPOL, about 8 vol. % ethanol, about 1% CPC, and about 64 vol. % of soybean oil, and about 23 vol. % of DiH$_2$O (designated herein as Y4EC). In still another embodiment the formulation comprises about 8% TYLOXAPOL, about 8% ethanol, about 1 vol. % of CPC, and about 64 vol. % of soybean oil, and about 19 vol. % of DiH$_2$O (designated herein as Y8EC). A further embodiment comprises about 8 vol. % of TYLOXAPOL, about 8 vol. % of ethanol, about 1 vol. % of CPC, about 64 vol. % of soybean oil, and about 19 vol. % of 1×PBS (designated herein as Y8EC PBS).

In some embodiments of the present invention, a nanoemulsion comprises about 8 vol. % of ethanol, and about 1 vol. % of CPC, and about 64 vol. % of oil (e.g., soybean oil), and about 27 vol. % of aqueous phase (e.g., DiH$_2$O or PBS) (designated herein as EC).

In some embodiments, a nanoemulsion comprises from about 8 vol. % of sodium dodecyl sulfate (SDS), about 8 vol. % of tributyl phosphate (TBP), and about 64 vol. % of oil (e.g., soybean oil), and about 20 vol. % of aqueous phase (e.g., DiH$_2$O or PBS) (designated herein as S8P).

In some embodiments, a nanoemulsion comprises from about 1 to 2 vol. % of TRITON X-100, from about 1 to 2 vol. % of TYLOXAPOL, from about 7 to 8 vol. % of ethanol, about 1 vol. % of cetylpyridinium chloride (CPC), about 64 to 57.6 vol. % of oil (e.g., soybean oil), and about 23 vol. % of aqueous phase (e.g., DiH$_2$O or PBS). Additionally, some of these formulations further comprise about 5 mM of L-alanine/Inosine, and about 10 mM ammonium chloride. Some of these formulations comprise PBS. It is contemplated that the addition of PBS in some of these embodiments, allows the user to advantageously control the pH of the formulations. For example, one embodiment of the present invention comprises about 2 vol. % of TRITON X-100, about 2 vol. % of TYLOXAPOL, about 8 vol. % of ethanol, about 1 vol. % CPC, about 64 vol. % of soybean oil, and about 23 vol. % of aqueous phase DiH$_2$O. In another embodiment the formulation comprises about 1.8 vol. % of TRITON X-100, about 1.8 vol. % of TYLOXAPOL, about 7.2 vol. % of ethanol, about 0.9 vol. % of CPC, about 5 mM L-alanine/Inosine, and about 10 mM ammonium chloride, about 57.6 vol. % of soybean oil, and the remainder of 1×PBS (designated herein as 90% X2Y2EC/GE).

In alternative embodiments, a nanoemulsion comprises from about 5 vol. % of TWEEN 80, from about 8 vol. % of ethanol, from about 1 vol. % of CPC, about 64 vol. % of oil (e.g., soybean oil), and about 22 vol. % of DiH$_2$O (designated herein as W$_{80}$5EC).

In still other embodiments of the present invention, a nanoemulsion comprises from about 5 vol. % of TWEEN 20, from about 8 vol. % of ethanol, from about 1 vol. % of CPC, about 64 vol. % of oil (e.g., soybean oil), and about 22 vol. % of DiH$_2$O (designated herein as W$_{20}$5EC).

In still other embodiments of the present invention, a nanoemulsion comprises from about 2 to 8 vol. % of TRITON X-100, about 8 vol. % of ethanol, about 1 vol. % of CPC, about 60 to 70 vol. % of oil (e.g., soybean, or olive oil), and about 15 to 25 vol. % of aqueous phase (e.g., DiH$_2$O or PBS). For example, the present invention contemplates formulations comprising about 2 vol. % of TRITON X-100, about 8 vol. % of ethanol, about 64 vol. % of soybean oil, and about 26 vol. % of DiH$_2$O (designated herein as X2E). In other similar embodiments, a nanoemulsion comprises about 3 vol. % of TRITON X-100, about 8 vol. % of ethanol, about 64 vol. % of soybean oil, and about 25 vol. % of DiH$_2$O (designated herein as X3E). In still further embodiments, the formulations comprise about 4 vol. % Triton of X-100, about 8 vol. % of ethanol, about 64 vol. % of soybean oil, and about 24 vol. % of DiH$_2$O (designated herein as X4E). In yet other embodiments, a nanoemulsion comprises about 5 vol. % of TRITON X-100, about 8 vol. % of ethanol, about 64 vol. % of soybean oil, and about 23 vol. % of DiH$_2$O (designated herein as X5E). In some embodiments, a nanoemulsion comprises about 6 vol. % of TRITON X-100, about 8 vol. % of ethanol, about 64 vol. % of soybean oil, and about 22 vol. % of DiH$_2$O (designated herein as X6E). In still further embodiments of the present invention, a nanoemulsion comprises about 8 vol. % of TRITON X-100, about 8 vol. % of ethanol, about 64 vol. % of soybean oil, and about 20 vol. % of DiH$_2$O (designated herein as X8E). In still further embodiments, a nanoemulsion comprises about 8 vol. % of TRITON X-100, about 8 vol. % of ethanol, about 64 vol. % of olive oil, and about 20 vol. % of DiH$_2$O (designated herein as X8E O). In yet another embodiment, a nanoemulsion comprises 8 vol. % of TRITON X-100, about 8 vol. % ethanol, about 1 vol. % CPC, about 64 vol. % of soybean oil, and about 19 vol. % of DiH$_2$O (designated herein as X8EC).

In alternative embodiments of the present invention, a nanoemulsion comprises from about 1 to 2 vol. % of TRITON X-100, from about 1 to 2 vol. % of TYLOXAPOL, from about 6 to 8 vol. % TBP, from about 0.5 to 1.0 vol. % of CPC, from about 60 to 70 vol. % of oil (e.g., soybean), and about 1 to 35 vol. % of aqueous phase (e.g., DiH$_2$O or PBS). Additionally, certain of these nanoemulsions may comprise from about 1 to 5 vol. % of trypticase soy broth, from about 0.5 to 1.5 vol. % of yeast extract, about 5 mM L-alanine/Inosine, about 10 mM ammonium chloride, and from about 20-40 vol. % of liquid baby formula. In some embodiments comprising liquid baby formula, the formula comprises a casein hydrolysate (e.g., Neutramigen, or Progestimil, and the like). In some of these embodiments, a nanoemulsion further comprises from about 0.1 to 1.0 vol. % of sodium thiosulfate, and from about 0.1 to 1.0 vol. % of sodium citrate. Other similar embodiments comprising these basic components employ phosphate buffered saline (PBS) as the aqueous phase. For example, one embodiment comprises about 2 vol. % of TRITON X-100, about 2 vol. % TYLOXAPOL, about 8 vol. % TBP, about 1 vol. % of CPC, about 64 vol. % of soybean oil, and about 23 vol. % of DiH$_2$O (designated herein as X2Y2EC). In still other embodiments, the inventive formulation comprises about 2 vol. % of TRITON X-100, about 2 vol. % TYLOXAPOL, about 8 vol. % TBP, about 1 vol. % of CPC, about 0.9 vol. % of sodium thiosulfate, about 0.1 vol. % of sodium citrate, about 64 vol. % of soybean oil, and about 22 vol. % of DiH$_2$O (designated herein as X2Y2PC STS1). In another similar embodiment, a nanoemulsion comprises about 1.7 vol. % TRITON X-100, about 1.7 vol. % TYLOXAPOL, about 6.8 vol. % TBP, about 0.85% CPC, about 29.2% NEUTRAMIGEN, about 54.4 vol. % of soybean oil, and about 4.9 vol. % of DiH$_2$O (designated herein as 85% X2Y2PC/baby). In yet another embodiment of the present invention, a nanoemulsion comprises about 1.8 vol. % of TRITON X-100, about 1.8 vol. % of TYLOXAPOL, about 7.2 vol. % of TBP, about 0.9 vol. % of CPC, about 5 mM L-alanine/Inosine, about 10 mM ammonium chloride, about 57.6 vol. % of soybean oil, and the remainder vol. % of 0.1×PBS (designated herein as 90% X2Y2 PC/GE). In still another embodiment, a nanoemulsion comprises about 1.8 vol. % of TRITON X-100, about 1.8 vol. % of TYLOXAPOL, about 7.2 vol. % TBP, about 0.9 vol. % of CPC, and about 3 vol. % trypticase soy broth, about 57.6 vol. % of soybean oil, and about 27.7 vol. % of DiH$_2$O (designated herein as 90% X2Y2PC/TSB). In another embodiment of the present invention, a nanoemulsion comprises about 1.8 vol. % TRITON X-100, about 1.8 vol. % TYLOXAPOL, about 7.2 vol. % TBP, about 0.9 vol. % CPC, about 1 vol. % yeast extract, about 57.6 vol. % of soybean oil, and about 29.7 vol. % of DiH$_2$O (designated herein as 90% X2Y2PC/YE).

In some embodiments of the present invention, a nanoemulsion comprises about 3 vol. % of TYLOXAPOL, about 8 vol. % of TBP, and about 1 vol. % of CPC, about 60 to 70 vol. % of oil (e.g., soybean or olive oil), and about 15 to 30 vol. % of aqueous phase (e.g., DiH$_2$O or PBS). In a particular embodiment of the present invention, a nanoemulsion comprises about 3 vol. % of TYLOXAPOL, about 8 vol. % of TBP, and about 1 vol. % of CPC, about 64 vol. % of soybean, and about 24 vol. % of DiH$_2$O (designated herein as Y3PC).

In some embodiments of the present invention, a nanoemulsion comprises from about 4 to 8 vol. % of TRITON X-100, from about 5 to 8 vol. % of TBP, about 30 to 70 vol. % of oil (e.g., soybean or olive oil), and about 0 to 30 vol. % of aqueous phase (e.g., DiH$_2$O or PBS). Additionally, certain of these embodiments further comprise about 1 vol. % of CPC, about 1 vol. % of benzalkonium chloride, about 1 vol. % cetylpyridinium bromide, about 1 vol. % cetyldimethyletylammonium bromide, 500 µM EDTA, about 10 mM ammonium chloride, about 5 mM Inosine, and about 5 mM L-alanine. For example, in a certain preferred embodiment, a nanoemulsion comprises about 8 vol. % of TRITON X-100, about 8 vol. % of TBP, about 64 vol. % of soybean oil, and about 20 vol. % of DiH$_2$O (designated herein as X8P). In another embodiment of the present invention, a nanoemulsion comprises about 8 vol. % of TRITON X-100, about 8 vol. % of TBP, about 1% of CPC, about 64 vol. % of soybean oil, and about 19 vol. % of DiH$_2$O (designated herein as X8PC). In still another embodiment, a nanoemulsion comprises about 8 vol. % TRITON X-100, about 8 vol. % of TBP, about 1 vol. % of CPC, about 50 vol. % of soybean oil, and about 33 vol. % of DiH$_2$O (designated herein as ATB-X1001). In yet another embodiment, the formulations comprise about 8 vol. % of TRITON X-100, about 8 vol. % of TBP, about 2 vol. % of CPC, about 50 vol. % of soybean oil, and about 32 vol. % of DiH$_2$O (designated herein as ATB-X002). In some embodiments, a nanoemulsion comprises about 4 vol. % TRITON X-100, about 4 vol. % of TBP, about 0.5 vol. % of CPC, about 32 vol. % of soybean oil, and about 59.5 vol. % of DiH$_2$O (designated herein as 50% X8PC). In some embodiments, a nanoemulsion comprises about 8 vol. % of TRITON X-100, about 8 vol. % of TBP, about 0.5 vol. % CPC, about 64 vol. % of soybean oil, and about 19.5 vol. % of DiH$_2$O (designated herein as X8PC$_{1/2}$). In some embodiments of the present invention, a nanoemulsion comprises about 8 vol. % of TRITON X-100, about 8 vol. % of TBP, about 2 vol. % of CPC, about 64 vol. % of soybean oil, and about 18 vol. % of DiH$_2$O (designated herein as X8PC2). In other embodiments, a nanoemulsion comprises about 8 vol. % of TRITON X-100, about 8% of TBP, about 1% of benzalkonium chloride, about 50 vol. % of soybean oil, and about 33 vol. % of DiH$_2$O (designated herein as X8P BC). In an alternative embodiment of the present invention, a nanoemulsion comprises about 8 vol. % of TRITON X-100, about 8 vol. % of TBP, about 1 vol. % of cetylpyridinium bromide, about 50 vol. % of soybean oil, and about 33 vol. % of DiH$_2$O (designated herein as X8P CPB). In another exemplary embodiment of the present invention, a nanoemulsion comprises about 8 vol. % of TRITON X-100, about 8 vol. % of TBP, about 1 vol. % of cetyldimethyletylammonium bromide, about 50 vol. % of soybean oil, and about 33 vol. % of DiH$_2$O (designated herein as X8P CTAB). In still further embodiments, a nanoemulsion comprises about 8 vol. % of TRITON X-100, about 8 vol. % of TBP, about 1 vol. % of CPC, about 500 µM EDTA, about 64 vol. % of soybean oil, and about 15.8 vol. % DiH$_2$O (designated herein as X8PC EDTA). In some embodiments, a nanoemulsion comprises 8 vol. % of TRITON X-100, about 8 vol. % of TBP, about 1 vol. % of CPC, about 10 mM ammonium chloride, about 5 mM Inosine, about 5 mM L-alanine, about 64 vol. % of soybean oil, and about 19 vol. % of DiH$_2$O or PBS (designated herein as X8PC GE$_{1x}$). In another embodiment of the present invention, a nanoemulsion comprises about 5 vol. % of TRITON X-100, about 5% of TBP, about 1 vol. % of CPC, about 40 vol. % of soybean oil, and about 49 vol. % of DiH$_2$O (designated herein as X5P$_5$C).

In some embodiments of the present invention, a nanoemulsion comprises about 2 vol. % TRITON X-100, about 6 vol. % TYLOXAPOL, about 8 vol. % ethanol, about 64 vol. % of soybean oil, and about 20 vol. % of DiH$_2$O (designated herein as X2Y6E).

In an additional embodiment of the present invention, a nanoemulsion comprises about 8 vol. % of TRITON X-100, and about 8 vol. % of glycerol, about 60 to 70 vol. % of oil (e.g., soybean or olive oil), and about 15 to 25 vol. % of aqueous phase (e.g., DiH$_2$O or PBS). Certain nanoemulsion compositions (e.g., used to generate an immune response (e.g., for use as a vaccine) comprise about 1 vol. % L-ascorbic acid. For example, one particular embodiment comprises about 8 vol. % of TRITON X-100, about 8 vol. % of glycerol, about 64 vol. % of soybean oil, and about 20 vol. % of DiH$_2$O (designated herein as X8G). In still another embodiment, a nanoemulsion comprises about 8 vol. % of TRITON X-100, about 8 vol. % of glycerol, about 1 vol. % of L-ascorbic acid, about 64 vol. % of soybean oil, and about 19 vol. % of DiH$_2$O (designated herein as X8GV$_c$).

In still further embodiments, a nanoemulsion comprises about 8 vol. % of TRITON X-100, from about 0.5 to 0.8 vol. % of TWEEN 60, from about 0.5 to 2.0 vol. % of CPC, about 8 vol. % of TBP, about 60 to 70 vol. % of oil (e.g., soybean or olive oil), and about 15 to 25 vol. % of aqueous phase (e.g., DiH$_2$O or PBS). For example, in one particular embodiment a nanoemulsion comprises about 8 vol. % of TRITON X-100, about 0.70 vol. % of TWEEN 60, about 1 vol. % of CPC, about 8 vol. % of TBP, about 64 vol. % of soybean oil, and about 18.3 vol. % of DiH$_2$O (designated herein as X8W60PC$_1$). In some embodiments, a nanoemulsion comprises about 8 vol. % of TRITON X-100, about 0.71 vol. % of TWEEN 60, about 1 vol. % of CPC, about 8 vol. % of TBP, about 64 vol. % of soybean oil, and about 18.29 vol. % of DiH$_2$O (designated herein as W60$_{0.7}$X8PC). In yet other embodiments, a nanoemulsion comprises from about 8 vol. % of TRITON X-100, about 0.7 vol. % of TWEEN 60, about 0.5 vol. % of CPC, about 8 vol. % of TBP, about 64 to 70 vol. % of soybean oil, and about 18.8 vol. % of DiH$_2$O (designated herein as X8W60PC$_2$). In still other embodiments, a nanoemulsion comprises about 8 vol. % of TRITON X-100, about 0.71 vol. % of TWEEN 60, about 2 vol. % of CPC, about 8 vol. % of TBP, about 64 vol. % of soybean oil, and about 17.3 vol. % of DiH$_2$O. In another embodiment of the present invention, a nanoemulsion comprises about 0.71 vol. % of TWEEN 60, about 1 vol. % of CPC, about 8 vol. % of TBP, about 64 vol. % of soybean oil, and about 25.29 vol. % of DiH$_2$O (designated herein as W60$_{0.7}$PC).

In another embodiment of the present invention, a nanoemulsion comprises about 2 vol. % of dioctyl sulfosuccinate, either about 8 vol. % of glycerol, or about 8 vol. % TBP, in addition to, about 60 to 70 vol. % of oil (e.g., soybean or olive oil), and about 20 to 30 vol. % of aqueous phase (e.g., DiH$_2$O or PBS). For example, in some embodiments, a nanoemulsion comprises about 2 vol. % of dioctyl sulfosuccinate, about 8 vol. % of glycerol, about 64 vol. % of soybean oil, and about 26 vol. % of DiH$_2$O (designated herein as D2G). In another related embodiment, a nanoemulsion comprises about 2 vol. % of dioctyl sulfosuccinate, and about 8 vol. % of TBP, about 64 vol. % of soybean oil, and about 26 vol. % of DiH$_2$O (designated herein as D2P).

In still other embodiments of the present invention, a nanoemulsion comprises about 8 to 10 vol. % of glycerol, and about 1 to 10 vol. % of CPC, about 50 to 70 vol. % of oil (e.g., soybean or olive oil), and about 15 to 30 vol. % of aqueous phase (e.g., DiH$_2$O or PBS). Additionally, in certain of these embodiments, a nanoemulsion further comprises about 1 vol. % of L-ascorbic acid. For example, in some embodiments, a nanoemulsion comprises about 8 vol. % of glycerol, about 1 vol. % of CPC, about 64 vol. % of soybean oil, and about 27 vol. % of DiH$_2$O (designated herein as GC). In some embodiments, a nanoemulsion comprises about 10 vol. % of glycerol, about 10 vol. % of CPC, about 60 vol. % of soybean oil, and about 20 vol. % of DiH$_2$O (designated herein as GC10). In still another embodiment of the present invention, a nanoemulsion comprises about 10 vol. % of glycerol, about 1 vol. % of CPC, about 1 vol. % of L-ascorbic acid, about 64 vol. % of soybean or oil, and about 24 vol. % of DiH$_2$O (designated herein as GCV$_c$).

In some embodiments of the present invention, a nanoemulsion comprises about 8 to 10 vol. % of glycerol, about 8 to 10 vol. % of SDS, about 50 to 70 vol. % of oil (e.g., soybean or olive oil), and about 15 to 30 vol. % of aqueous phase (e.g., DiH$_2$O or PBS). Additionally, in certain of these embodiments, a nanoemulsion further comprise about 1 vol. % of lecithin, and about 1 vol. % of p-Hydroxybenzoic acid methyl ester. Exemplary embodiments of such formulations comprise about 8 vol. % SDS, 8 vol. % of glycerol, about 64 vol. % of soybean oil, and about 20 vol. % of DiH$_2$O (designated herein as S8G). A related formulation comprises about 8 vol. % of glycerol, about 8 vol. % of SDS, about 1 vol. % of lecithin, about 1 vol. % of p-Hydroxybenzoic acid methyl ester, about 64 vol. % of soybean oil, and about 18 vol. % of DiH$_2$O (designated herein as S8GL1B1).

In yet another embodiment of the present invention, a nanoemulsion comprises about 4 vol. % of TWEEN 80, about 4 vol. % of TYLOXAPOL, about 1 vol. % of CPC, about 8 vol. % of ethanol, about 64 vol. % of soybean oil, and about 19 vol. % of DiH$_2$O (designated herein as W$_{80}$4Y4EC).

In some embodiments of the present invention, a nanoemulsion comprises about 0.01 vol. % of CPC, about 0.08 vol. % of TYLOXAPOL, about 10 vol. % of ethanol, about 70 vol. % of soybean oil, and about 19.91 vol. % of DiH$_2$O (designated herein as Y.08EC.01).

In yet another embodiment of the present invention, a nanoemulsion comprises about 8 vol. % of sodium lauryl sulfate, and about 8 vol. % of glycerol, about 64 vol. % of soybean oil, and about 20 vol. % of DiH$_2$O (designated herein as SLS8G).

The specific formulations described above are simply examples to illustrate the variety of nanoemulsions that find use (e.g., to inactivate and/or neutralize a pathogen, and for generating an immune response in a subject (e.g., for use as a vaccine)) in the present invention. The present invention contemplates that many variations of the above formulations, as well as additional nanoemulsions, find use in the methods of the present invention. Candidate emulsions can be easily tested to determine if they are suitable. First, the desired ingredients are prepared using the methods described herein, to determine if an emulsion can be formed. If an emulsion cannot be formed, the candidate is rejected. For example, a candidate composition made of 4.5% sodium thiosulfate, 0.5% sodium citrate, 10% n-butanol, 64% soybean oil, and 21% DiH$_2$O does not form an emulsion.

Second, the candidate emulsion should form a stable emulsion. An emulsion is stable if it remains in emulsion form for a sufficient period to allow its intended use (e.g., to generate an immune response in a subject). For example, for emulsions that are to be stored, shipped, etc., it may be desired that the composition remain in emulsion form for months to years. Typical emulsions that are relatively unstable, will lose their form within a day. For example, a candidate composition made of 8% 1-butanol, 5% TWEEN 10, 1% CPC, 64% soybean oil, and 22% DiH$_2$O does not form a stable emulsion. Nanoemulsions that have been shown to be stable include, but are not limited to, 8 vol. % of TRITON X-100, about 8 vol. % of TBP, about 64 vol. % of soybean oil, and about 20 vol. % of DiH$_2$O (designated herein as X8P); 5 vol. % of TWEEN 20, from about 8 vol. % of ethanol, from about 1 vol. % of CPC, about 64 vol. % of oil (e.g., soybean oil), and about 22 vol. % of DiH$_2$O (designated herein as W$_{20}$5EC); 0.08% Triton X-100, 0.08% Glycerol, 0.01% Cetylpyridinium Chloride, 99% Butter, and 0.83% diH$_2$O (designated herein as 1% X8GC Butter); 0.8% Triton X-100, 0.8% Glycerol, 0.1% Cetylpyridinium Chloride, 6.4% Soybean Oil, 1.9% diH$_2$O, and 90% Butter (designated herein as 10% X8GC Butter); 2% W$_{20}$5EC, 1% Natrosol 250L NF, and 97% diH$_2$O (designated herein as 2% W$_{20}$5EC L GEL); 1% Cetylpyridinium Chloride, 5% TWEEN 20, 8% Ethanol, 64% 70 Viscosity Mineral Oil, and 22% diH$_2$O (designated herein as W$_{20}$5EC 70 Mineral Oil); 1% Cetylpyridinium Chloride, 5% TWEEN 20, 8% Ethanol, 64% 350 Viscosity Mineral Oil, and 22% diH$_2$O (designated herein as W$_{20}$5EC 350 Mineral Oil). In some embodiments, nanoemulsions of the present invention are stable for over a week, over a month, or over a year.

Third, the candidate emulsion should have efficacy for its intended use. For example, a nanoemulsion should inactivate (e.g., kill or inhibit growth of) a pathogen to a desired level (e.g., 1 log, 2 log, 3 log, 4 log, . . . reduction). Using the methods described herein, one is capable of determining the suitability of a particular candidate emulsion against the desired pathogen. Generally, this involves exposing the pathogen to the emulsion for one or more time periods in a side-by-side experiment with the appropriate control samples (e.g., a negative control such as water) and determining if, and to what degree, the emulsion inactivates (e.g., kills and/or neutralizes) the microorganism. For example, a candidate composition made of 1% ammonium chloride, 5% TWEEN 20, 8% ethanol, 64% soybean oil, and 22% DiH$_2$O was shown not to be an effective emulsion. The following candidate emulsions were shown to be effective using the methods described herein: 5% TWEEN 20, 5% Cetylpyridinium Chloride, 10% Glycerol, 60% Soybean Oil, and 20% diH$_2$O (designated herein as W$_{20}$5 GC5); 1% Cetylpyridinium Chloride, 5% TWEEN 20, 10% Glycerol, 64% Soybean Oil, and 20% diH$_2$O (designated herein as W$_{20}$5 GC); 1% Cetylpyridinium Chloride, 5% TWEEN 20, 8% Ethanol, 64% Olive Oil, and 22% diH$_2$O (designated herein as W$_{20}$5EC Olive Oil); 1% Cetylpyridinium Chloride, 5% TWEEN 20, 8% Ethanol, 64% Flaxseed Oil, and 22% diH$_2$O (designated herein as W$_{20}$5EC Flaxseed Oil); 1% Cetylpyridinium Chloride, 5% TWEEN 20, 8% Ethanol, 64% Corn Oil, and 22% diH$_2$O (designated herein as W$_{20}$5EC Corn Oil); 1% Cetylpyridinium Chloride, 5% TWEEN 20, 8% Ethanol, 64% Coconut Oil, and 22% diH$_2$O (designated herein as W$_{20}$5EC Coconut Oil); 1% Cetylpyridinium Chloride, 5% TWEEN 20, 8% Ethanol, 64% Cottonseed Oil, and 22% diH$_2$O (designated herein as W$_{20}$5EC Cottonseed Oil); 8% Dextrose, 5% TWEEN 10, 1% Cetylpyridinium Chloride, 64% Soybean Oil, and 22% diH$_2$O (designated herein as W$_{20}$5C Dextrose); 8% PEG 200, 5% TWEEN 10, 1% Cetylpyridinium Chloride, 64% Soybean Oil, and 22% diH$_2$O (designated herein as W$_{20}$5C PEG 200); 8% Methanol, 5% TWEEN 10, 1% Cetylpyridinium Chloride, 64% Soybean Oil, and 22% diH$_2$O (designated herein as W$_{20}$5C Methanol); 8% PEG 1000, 5% TWEEN 10, 1% Cetylpyridinium Chloride, 64% Soybean Oil, and 22% diH$_2$O (designated herein as W$_{20}$5C PEG 1000); 2% W$_{20}$5EC, 2% Natrosol 250H NF, and 96% diH$_2$O (designated herein as 2% W$_{20}$5EC Natrosol 2, also called 2% W$_{20}$5EC GEL); 2% W$_{20}$5EC, 1% Natrosol 250H NF, and 97% diH$_2$O (designated herein as 2% W$_{20}$5EC Natrosol 1); 2% W$_{20}$5EC, 3% Natrosol 250H NF, and 95% diH$_2$O (designated herein as 2% W$_{20}$5EC Natrosol 3); 2% W$_{20}$5EC, 0.5% Natrosol 250H NF, and 97.5% diH$_2$O (designated herein as 2% W$_{20}$5EC Natrosol 0.5); 2% W$_{20}$5EC, 2% Methocel A, and 96% diH$_2$O (designated herein as 2% W$_{20}$5EC Methocel A); 2% W$_{20}$5EC, 2% Methocel K, and 96% diH$_2$O (designated herein as 2% W$_{20}$5EC Methocel K);

2% Natrosol, 0.1% X8PC, 0.1×PBS, 5 mM L-alanine, 5 mM Inosine, 10 mM Ammonium Chloride, and diH$_2$O (designated herein as 0.1% X8PC/GE+2% Natrosol); 2% Natrosol, 0.8% Triton X-100, 0.8% Tributyl Phosphate, 6.4% Soybean Oil, 0.1% Cetylpyridinium Chloride, 0.1×PBS, 5 mM L-alanine, 5 mM Inosine, 10 mM Ammonium Chloride, and diH$_2$O (designated herein as 10% X8PC/GE+2% Natrosol); 1% Cetylpyridinium Chloride, 5% TWEEN 20, 8% Ethanol, 64% Lard, and 22% diH$_2$O (designated herein as W$_{20}$5EC Lard); 1% Cetylpyridinium Chloride, 5% TWEEN 20, 8% Ethanol, 64% Mineral Oil, and 22% diH$_2$O (designated herein as W$_{20}$5EC Mineral Oil); 0.1% Cetylpyridinium Chloride, 2% Nerolidol, 5% TWEEN 20, 10% Ethanol, 64% Soybean Oil, and 18.9% diH$_2$O (designated herein as W$_{20}$5EC$_{0.1}$N); 0.1% Cetylpyridinium Chloride, 2% Farnesol, 5% TWEEN 20, 10% Ethanol, 64% Soybean Oil, and 18.9% diH$_2$O (designated herein as W$_{20}$5EC$_{0.1}$F); 0.1% Cetylpyridinium Chloride, 5% TWEEN 20, 10% Ethanol, 64% Soybean Oil, and 20.9% diH$_2$O (designated herein as W$_{20}$5EC$_{0.1}$); 10% Cetylpyridinium Chloride, 8% Tributyl Phosphate, 8% Triton X-100, 54% Soybean Oil, and 20% diH$_2$O (designated herein as X8PC$_{10}$); 5% Cetylpyridinium Chloride, 8% Triton X-100, 8% Tributyl Phosphate, 59% Soybean Oil, and 20% diH$_2$O (designated herein as X8PC$_5$); 0.02% Cetylpyridinium Chloride, 0.1% TWEEN 20, 10% Ethanol, 70% Soybean Oil, and 19.88% diH$_2$O (designated herein as W$_{20}$0.1 EC$_{0.02}$); 1% Cetylpyridinium Chloride, 5% TWEEN 20, 8% Glycerol, 64% Mobil 1, and 22% diH$_2$O (designated herein as W$_{20}$5 GC Mobil 1); 7.2% Triton X-100, 7.2% Tributyl Phosphate, 0.9% Cetylpyridinium Chloride, 57.6% Soybean Oil, 0.1×PBS, 5 mM L-alanine, 5 mM Inosine, 10 mM Ammonium Chloride, and 25.87% diH$_2$O (designated herein as 90% X8PC/GE); 7.2% Triton X-100, 7.2% Tributyl Phosphate, 0.9% Cetylpyridinium Chloride, 57.6% Soybean Oil, 1% EDTA, 5 mM L-alanine, 5 mM Inosine, 10 mM Ammonium Chloride, 0.1×PBS, and diH$_2$O (designated herein as 90% X8PC/GE EDTA); and 7.2% Triton X-100, 7.2% Tributyl Phosphate, 0.9% Cetylpyridinium Chloride, 57.6% Soybean Oil, 1% Sodium Thiosulfate, 5 mM L-alanine, 5 mM Inosine, 10 mM Ammonium Chloride, 0.1×PBS, and diH$_2$O (designated herein as 90% X8PC/GE STS).

In preferred embodiments of the present invention, the nanoemulsions are non-toxic (e.g., to humans, plants, or animals), non-irritant (e.g., to humans, plants, or animals), and non-corrosive (e.g., to humans, plants, or animals or the environment), while possessing potency against a broad range of microorganisms including bacteria, fungi, viruses, and spores. While a number of the above described nanoemulsions meet these qualifications, the following description provides a number of preferred non-toxic, non-irritant, non-corrosive, anti-microbial nanoemulsions of the present invention (hereinafter in this section referred to as "non-toxic nanoemulsions").

In some embodiments the non-toxic nanoemulsions comprise surfactant lipid preparations (SLPs) for use as broad-spectrum antimicrobial agents that are effective against bacteria and their spores, enveloped viruses, and fungi. In preferred embodiments, these SLPs comprises a mixture of oils, detergents, solvents, and cationic halogen-containing compounds in addition to several ions that enhance their biocidal activities. These SLPs are characterized as stable, non-irritant, and non-toxic compounds compared to commercially available bactericidal and sporicidal agents, which are highly irritant and/or toxic.

Ingredients for use in the non-toxic nanoemulsions include, but are not limited to: detergents (e.g., TRITON X-100 (5-15%) or other members of the TRITON family, TWEEN 60 (0.5-2%) or other members of the TWEEN family, or TYLOXAPOL (1-10%)); solvents (e.g., tributyl phosphate (5-15%)); alcohols (e.g., ethanol (5-15%) or glycerol (5-15%)); oils (e.g., soybean oil (40-70%)); cationic halogen-containing compounds (e.g., cetylpyridinium chloride (0.5-2%), cetylpyridinium bromide (0.5-2%)), or cetyldimethylethyl ammonium bromide (0.5-2%)); quaternary ammonium compounds (e.g., benzalkonium chloride (0.5-2%), N-alkyldimethylbenzyl ammonium chloride (0.5-2%)); ions (calcium chloride (1 mM-40 mM), ammonium chloride (1 mM-20 mM), sodium chloride (5 mM-200 mM), sodium phosphate (1 mM-20 mM)); nucleosides (e.g., inosine (50 μM-20 mM)); and amino acids (e.g., L-alanine (50 μM-20 mM)). Emulsions are prepared, for example, by mixing in a high shear mixer for 3-10 minutes. The emulsions may or may not be heated before mixing at 82° C. for 1 hour.

Quaternary ammonium compounds for use in the present include, but are not limited to, N-alkyldimethyl benzyl ammonium saccharinate; 1,3,5-Triazine-1,3,5(2H,4H,6H)-triethanol; 1-Decanaminium, N-decyl-N, N-dimethyl-, chloride (or) Didecyl dimethyl ammonium chloride; 2-(2-(p-(Diisobuyl)cresosxy)ethoxy)ethyl dimethyl benzyl ammonium chloride; 2-(2-(p-(Diisobutyl)phenoxy)ethoxy) ethyl dimethyl benzyl ammonium chloride; alkyl 1 or 3 benzyl-1-(2-hydroxyethyl)-2-imidazolinium chloride; alkyl bis(2-hydroxyethyl)benzyl ammonium chloride; alkyl demethyl benzyl ammonium chloride; alkyl dimethyl 3,4-dichlorobenzyl ammonium chloride (100% C12); alkyl dimethyl 3,4-dichlorobenzyl ammonium chloride (50% C14, 40% C12, 10% C16); alkyl dimethyl 3,4-dichlorobenzyl ammonium chloride (55% C14, 23% C12, 20% C16); alkyl dimethyl benzyl ammonium chloride; alkyl dimethyl benzyl ammonium chloride (100% C14); alkyl dimethyl benzyl ammonium chloride (100% C16); alkyl dimethyl benzyl ammonium chloride (41% C14, 28% C12); alkyl dimethyl benzyl ammonium chloride (47% C12, 18% C14); alkyl dimethyl benzyl ammonium chloride (55% C16, 20% C14); alkyl dimethyl benzyl ammonium chloride (58% C14, 28% C16); alkyl dimethyl benzyl ammonium chloride (60% C14, 25% C12); alkyl dimethyl benzyl ammonium chloride (61% C11, 23% C14); alkyl dimethyl benzyl ammonium chloride (61% C12, 23% C14); alkyl dimethyl benzyl ammonium chloride (65% C12, 25% C14); alkyl dimethyl benzyl ammonium chloride (67% C12, 24% C14); alkyl dimethyl benzyl ammonium chloride (67% C12, 25% C14); alkyl dimethyl benzyl ammonium chloride (90% C14, 5% C12); alkyl dimethyl benzyl ammonium chloride (93% C14, 4% C12); alkyl dimethyl benzyl ammonium chloride (95% C16, 5% C18); alkyl dimethyl benzyl ammonium chloride (and) didecyl dimethyl ammonium chloride; alkyl dimethyl benzyl ammonium chloride (as in fatty acids); alkyl dimethyl benzyl ammonium chloride (C12-C16); alkyl dimethyl benzyl ammonium chloride (C12-C18); alkyl dimethyl benzyl and dialkyl dimethyl ammonium chloride; alkyl dimethyl dimethylbenzyl ammonium chloride; alkyl dimethyl ethyl ammonium bromide (90% C14, 5% C16, 5% C12); alkyl dimethyl ethyl ammonium bromide (mixed alkyl and alkenyl groups as in the fatty acids of soybean oil); alkyl dimethyl ethylbenzyl ammonium chloride; alkyl dimethyl ethylbenzyl ammonium chloride (60% C14); alkyl dimethyl isoproylbenzyl ammonium chloride (50% C12, 30% C14, 17% C16, 3% C18); alkyl trimethyl ammonium chloride (58% C18, 40% C16, 1% C14, 1% C12); alkyl trimethyl ammonium chloride (90% C18, 10% C16); alkyldimethyl (ethylbenzyl) ammonium chloride (C12-18); Di-(C8-10)- alkyl dimethyl ammonium chlorides; dialkyl dimethyl ammonium chloride; dialkyl dimethyl ammonium chloride; dialkyl dimethyl ammonium chloride; dialkyl methyl benzyl ammonium chloride; didecyl dimethyl ammonium chloride; diisodecyl dimethyl ammonium chloride; dioctyl dimethyl ammonium chloride; dodecyl bis(2-hydroxyethyl)octyl hydrogen ammonium chloride; dodecyl dimethyl benzyl ammonium chloride; dodecylcarbamoyl methyl dimethyl benzyl ammonium chloride; heptadecyl hydroxyethylimidazolinium chloride; hexahydro-1,3,5-thris(2-hydroxyethyl)-s-triazine; myristalkonium chloride (and) Quat RNIUM 14; N,N-Dimethyl-2-hydroxypropylammonium chloride polymer; n-alkyl dimethyl benzyl ammonium chloride; n-alkyl dimethyl ethylbenzyl ammonium chloride; n-tetradecyl dimethyl benzyl ammonium chloride monohydrate; octyl decyl dimethyl ammonium chloride; octyl dodecyl dimethyl ammonium chloride; octyphenoxyethoxyethyl dimethyl benzyl ammonium chloride; oxydiethylenebis(alkyl dimethyl ammonium chloride); quaternary ammonium compounds, dicoco alkyldimethyl, chloride; trimethoxysily propyl dimethyl octadecyl ammonium chloride; trimethoxysilyl quats, trimethyl dodecylbenzyl ammonium chloride; n-dodecyl dimethyl ethylbenzyl ammonium chloride; n-hexadecyl dimethyl benzyl ammonium chloride; n-tetradecyl dimethyl benzyl ammonium chloride; n-tetradecyl dimethyl ethyylbenzyl ammonium chloride; and n-octadecyl dimethyl benzyl ammonium chloride.

In general, the preferred non-toxic nanoemulsions are characterized by the following: they are approximately 200-800 nm in diameter, although both larger and smaller diameter nanoemulsions are contemplated; the charge depends on the ingredients; they are stable for relatively long periods of time (e.g., up to two years), with preservation of their biocidal activity; they are non-irritant and non-toxic compared to their individual components due, at least in part, to their oil contents that markedly reduce the toxicity of the detergents and the solvents; they are effective at concentrations as low as 0.1%; they have antimicrobial activity against most vegetative bacteria (including Gram-positive and Gram-negative organisms), fungi, and enveloped and nonenveloped viruses in 15 minutes (e.g., 99.99% killing); and they have sporicidal activity in 1-4 hours (e.g., 99.99% killing) when produced with germination enhancers.

The present invention is not limited by the type or strain of *Bacillus* used or immunogenic protein derived therefrom. For example, 89 different strains of *B. anthracis* have been identified, ranging from virulent Ames and Vollum strains with biological warfare and bioterrorism applications to benign Sterne strain used for inoculations (See, e.g., Easterday et al., J Clin Microbiol. 2005 43(4):1995-7). The strains differ in presence and activity of various genes, determining their virulence and production of antigens and toxins. Any one of these or yet to be identified or generated strains may be used in an immunogenic composition comprising a NE of the present invention.

In some embodiments, the immunogen may comprise one or more antigens derived from a pathogen (e.g., *B. anthracis*). For example, in some embodiments, the immunogen is a purified, recombinant, synthetic, or otherwise isolated protein (e.g., added to the NE to generate an immunogenic composition). Similarly, the immunogenic protein may be a derivative, variant, analogue or otherwise modified form of a protein from a pathogen. The present invention is not limited by the type of protein (e.g., derived from bacteria of the genus *Bacillus*) used for generation of an immunogenic composition of the present invention. Indeed, a variety of immunogenic proteins may be used including, but not limited to, protective antigen (PA), lethal factor (LF), edema factor (EF), PA degradation products (See, e.g., Farchaus, J., et al., Applied & Environmental Microbiol., 64(3):982-991 (1998)), as well as analogues, derivatives and modified forms thereof.

For example, *Bacillus* proteins of the present invention may be used in their native conformation, or more preferably, may be modified for vaccine use. These modifications may either be required for technical reasons relating to the method of purification, or they may be used to biologically inactivate one or several functional properties of the *Bacillus* proteins (e.g., that would otherwise be toxic). Thus the invention encompasses derivatives of *Bacillus* proteins that may be, for example, mutated proteins (e.g., that has undergone deletion, addition or substitution of one or more amino acids using well known techniques for site directed mutagenesis or any other conventional method).

*Bacillus* proteins (e.g., rPA) of the present invention may be modified by chemical methods during a purification process to render the proteins stable and monomeric. One method to prevent oxidative aggregation of a protein such is the use of chemical modifications of the protein's thiol groups. In a first step the disulphide bridges are reduced by treatment with a reducing agent such as DTT, β-mercaptoethanol, or gluthathione. In a second step the resulting thiols are blocked by reaction with an alkylating agent (e.g., the protein can be carboxyamidated/carbamidomethylated using iodoacetamide).

Each *Bacillus* family member alone, or in combination with another family member, may be used to generate a composition comprising a NE and an immunogen (e.g., used to generate an immune response) of the present invention. A composition comprising a NE and immunogen may comprise one or more strains of *B. anthracis*. Additionally, a composition comprising a NE and immunogen may comprise one or more strains of *B. anthracis*, and, in addition, one or more strains of a non-*B. anthracis* immunogen (e.g., a virus such as West Nile virus, Avian Influenza virus, Ebola virus, HSV, HPV, HCV, HIV, etc. or an immunogenic epitope thereof (e.g., gp120)).

The present invention is not limited by the particular formulation of a composition comprising a NE and immunogen of the present invention. Indeed, a composition comprising a NE and immunogen of the present invention may comprise one or more different agents in addition to the NE and immunogen. These agents or cofactors include, but are not limited to, adjuvants, surfactants, additives, buffers, solubilizers, chelators, oils, salts, therapeutic agents, drugs, bioactive agents, antibacterials, and antimicrobial agents (e.g., antibiotics, antivirals, etc.). In some embodiments, a composition comprising a NE and immunogen of the present invention comprises an agent and/or co-factor that enhance the ability of the immunogen to induce an immune response (e.g., an adjuvant). In some preferred embodiments, the presence of one or more co-factors or agents reduces the amount of immunogen required for induction of an immune response (e.g., a protective immune response (e.g., protective immunization)). In some embodiments, the presence of one or more co-factors or agents can be used to skew the immune response towards a cellular (e.g., T cell mediated) or humoral (e.g., antibody mediated) immune response. The present invention is not limited by the type of co-factor or agent used in a therapeutic agent of the present invention.

Adjuvants are described in general in Vaccine Design—the Subunit and Adjuvant Approach, edited by Powell and Newman, Plenum Press, New York, 1995. The present invention is not limited by the type of adjuvant utilized (e.g., for use in a composition (e.g., pharmaceutical composition) comprising a NE and immunogen). For example, in some embodiments, suitable adjuvants include an aluminium salt such as aluminium hydroxide gel (alum) or aluminium phosphate. In some embodiments, an adjuvant may be a salt of calcium, iron or zinc, or may be an insoluble suspension of acylated tyrosine, or acylated sugars, cationically or anionically derivatised polysaccharides, or polyphosphazenes.

In some embodiments, it is preferred that a composition comprising a NE and immunogen of the present invention comprises one or more adjuvants that induce a Th1-type response. However, in other embodiments, it will be preferred that a composition comprising a NE and immunogen of the present invention comprises one or more adjuvants that induce a Th2-type response.

In general, an immune response is generated to an antigen through the interaction of the antigen with the cells of the immune system. Immune responses may be broadly categorized into two categories: humoral and cell mediated immune responses (e.g., traditionally characterized by antibody and cellular effector mechanisms of protection, respectively). These categories of response have been termed Th1-type responses (cell-mediated response), and Th2-type immune responses (humoral response).

Stimulation of an immune response can result from a direct or indirect response of a cell or component of the immune system to an intervention (e.g., exposure to an immunogen). Immune responses can be measured in many ways including activation, proliferation or differentiation of cells of the immune system (e.g., B cells, T cells, dendritic cells, APCs, macrophages, NK cells, NKT cells etc.); up-regulated or down-regulated expression of markers and cytokines; stimulation of IgA, IgM, or IgG titer; splenomegaly (including increased spleen cellularity); hyperplasia and mixed cellular infiltrates in various organs. Other responses, cells, and components of the immune system that can be assessed with respect to immune stimulation are known in the art.

Although an understanding of the mechanism is not necessary to practice the present invention and the present invention is not limited to any particular mechanism of action, in some embodiments, compositions and methods of the present invention induce expression and secretion of cytokines (e.g., by macrophages, dendritic cells and CD4+ T cells). Modulation of expression of a particular cytokine can occur locally or systemically. It is known that cytokine profiles can determine T cell regulatory and effector functions in immune responses. In some embodiments, Th1-type cytokines can be induced, and thus, the immunostimulatory compositions of the present invention can promote a Th1 type antigen-specific immune response including cytotoxic T-cells. However in other embodiments, Th2-type cytokines can be induced thereby promoting a Th2 type antigen-specific immune response.

Cytokines play a role in directing the T cell response. Helper (CD4+) T cells orchestrate the immune response of mammals through production of soluble factors that act on other immune system cells, including B and other T cells. Most mature CD4+T helper cells express one of two cytokine profiles: Th1 or Th2. Th1-type CD4+ T cells secrete IL-2, IL-3, IFN-γ, GM-CSF and high levels of TNF-α. Th2 cells express IL-3, IL-4, IL-5, IL-6, IL-9, IL-10, IL-13, GM-CSF and low levels of TNF-α. Th1 type cytokines promote both cell-mediated immunity, and humoral immunity that is characterized by immunoglobulin class switching to IgG2a in mice and IgG1 in humans. Th1 responses may also be associated with delayed-type hypersensitivity and autoimmune disease. Th2 type cytokines induce primarily humoral immunity and induce class switching to IgG1 and IgE. The antibody isotypes associated with Th1 responses generally have neutralizing and opsonizing capabilities whereas those associated with Th2 responses are associated more with allergic responses.

Several factors have been shown to influence skewing of an immune response towards either a Th1 or Th2 type response. The best characterized regulators are cytokines. IL-12 and IFN-γ are positive Th1 and negative Th2 regulators. IL-12 promotes IFN-γ production, and IFN-γ provides positive feedback for IL-12. IL-4 and IL-10 appear important for the establishment of the Th2 cytokine profile and to down-regulate Th1 cytokine production.

Thus, in some preferred embodiments, the present invention provides a method of stimulating a Th1-type immune response in a subject comprising administering to a subject a composition comprising a NE and an immunogen. However, in other preferred embodiments, the present invention provides a method of stimulating a Th2-type immune response in a subject comprising administering to a subject a composition comprising a NE and an immunogen. In further preferred embodiments, adjuvants can be used (e.g., can be co-administered with a composition of the present invention) to skew an immune response toward either a Th1 or Th2 type immune response. For example, adjuvants that induce Th2 or weak Th1 responses include, but are not limited to, alum, saponins, and SB-As4. Adjuvants that induce Th1 responses include but are not limited to MPL, MDP, ISCOMS, IL-12, IFN-γ, and SB-AS2.

Several other types of Th1-type immunogens can be used (e.g., as an adjuvant) in compositions and methods of the present invention. These include, but are not limited to, the following. In some embodiments, monophosphoryl lipid A (e.g., in particular 3-de-O-acylated monophosphoryl lipid A (3D-MPL)), is used. 3D-MPL is a well known adjuvant manufactured by Ribi Immunochem, Montana. Chemically it is often supplied as a mixture of 3-de-O-acylated monophosphoryl lipid A with either 4, 5, or 6 acylated chains. In some embodiments, diphosphoryl lipid A, and 3-O-deacylated variants thereof are used. Each of these immunogens can be purified and prepared by methods described in GB 2122204B, hereby incorporated by reference in its entirety. Other purified and synthetic lipopolysaccharides have been described (See, e.g., U.S. Pat. No. 6,005,099 and EP 0 729 473; Hilgers et al., 1986, Int. Arch. Allergy. Immunol., 79(4):392-6; Hilgers et al., 1987, Immunology, 60(1):141-6; and EP 0 549 074, each of which is hereby incorporated by reference in its entirety). In some embodiments, 3D-MPL is used in the form of a particulate formulation (e.g., having a small particle size less than 0.2 μm in diameter, described in EP 0 689 454, hereby incorporated by reference in its entirety).

In some embodiments, saponins are used as an immunogen (e.g., Th1-type adjuvant) in a composition of the present invention. Saponins are well known adjuvants (See, e.g., Lacaille-Dubois and Wagner (1996) Phytomedicine vol 2 pp 363-386). Examples of saponins include Quil A (derived from the bark of the South American tree *Quillaja Saponaria Molina*), and fractions thereof (See, e.g., U.S. Pat. No. 5,057,540; Kensil, Crit Rev Ther Drug Carrier Syst, 1996, 12 (1-2):1-55; and EP 0 362 279, each of which is hereby incorporated by reference in its entirety). Also contemplated to be useful in the present invention are the haemolytic saponins QS7, QS17, and QS21 (HPLC purified fractions of Quil A; See, e.g., Kensil et al. (1991). J.

Immunology 146, 431-437, U.S. Pat. No. 5,057,540; WO 96/33739; WO 96/11711 and EP 0 362 279, each of which is hereby incorporated by reference in its entirety). Also contemplated to be useful are combinations of QS21 and polysorbate or cyclodextrin (See, e.g., WO 99/10008, hereby incorporated by reference in its entirety.

In some embodiments, an immunogenic oligonucleotide containing unmethylated CpG dinucleotides ("CpG") is used as an adjuvant in the present invention. CpG is an abbreviation for cytosine-guanosine dinucleotide motifs present in DNA. CpG is known in the art as being an adjuvant when administered by both systemic and mucosal routes (See, e.g., WO 96/02555, EP 468520, Davis et al., J. Immunol, 1998, 160(2):870-876; McCluskie and Davis, J. Immunol., 1998, 161(9):4463-6; and U.S. Pat. App. No. 20050238660, each of which is hereby incorporated by reference in its entirety). For example, in some embodiments, the immunostimulatory sequence is Purine-Purine-C-G-pyrimidine-pyrimidine; wherein the CG motif is not methylated.

Although an understanding of the mechanism is not necessary to practice the present invention and the present invention is not limited to any particular mechanism of action, in some embodiments, the presence of one or more CpG oligonucleotides activate various immune subsets including natural killer cells (which produce IFN-γ) and macrophages. In some embodiments, CpG oligonucleotides are formulated into a composition of the present invention for inducing an immune response. In some embodiments, a free solution of CpG is co-administered together with an antigen (e.g., present within a NE solution (See, e.g., WO 96/02555; hereby incorporated by reference). In some embodiments, a CpG oligonucleotide is covalently conjugated to an antigen (See, e.g., WO 98/16247, hereby incorporated by reference), or formulated with a carrier such as aluminium hydroxide (See, e.g., Brazolot-Millan et al., Proc. Natl. Acad Sci., USA, 1998, 95(26), 15553-8).

In some embodiments, adjuvants such as Complete Freunds Adjuvant and Incomplete Freunds Adjuvant, cytokines (e.g., interleukins (e.g., IL-2, IFN-γ, IL-4, etc.), macrophage colony stimulating factor, tumor necrosis factor, etc.), detoxified mutants of a bacterial ADP-ribosylating toxin such as a cholera toxin (CT), a pertussis toxin (PT), or an E. Coli heat-labile toxin (LT), particularly LT-K63 (where lysine is substituted for the wild-type amino acid at position 63) LT-R72 (where arginine is substituted for the wild-type amino acid at position 72), CT-S109 (where serine is substituted for the wild-type amino acid at position 109), and PT-K9/G129 (where lysine is substituted for the wild-type amino acid at position 9 and glycine substituted at position 129) (See, e.g., WO93/13202 and WO92/19265, each of which is hereby incorporated by reference), and other immunogenic substances (e.g., that enhance the effectiveness of a composition of the present invention) are used with a composition comprising a NE and immunogen of the present invention.

Additional examples of adjuvants that find use in the present invention include poly(di(carboxylatophenoxy) phosphazene (PCPP polymer; Virus Research Institute, USA); derivatives of lipopolysaccharides such as monophosphoryl lipid A (MPL; Ribi ImmunoChem Research, Inc., Hamilton, Mont.), muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland); and *Leishmania* elongation factor (a purified *Leishmania* protein; Corixa Corporation, Seattle, Wash.).

Adjuvants may be added to a composition comprising a NE and an immunogen, or, the adjuvant may be formulated with carriers, for example liposomes, or metallic salts (e.g., aluminium salts (e.g., aluminium hydroxide)) prior to combining with or co-administration with a composition comprising a NE and an immunogen.

In some embodiments, a composition comprising a NE and an immunogen comprises a single adjuvant. In other embodiments, a composition comprising a NE and an immunogen comprises two or more adjuvants (See, e.g., WO 94/00153; WO 95/17210; WO 96/33739; WO 98/56414; WO 99/12565; WO 99/11241; and WO 94/00153, each of which is hereby incorporated by reference in its entirety).

In some embodiments, a composition comprising a NE and an immunogen of the present invention comprises one or more mucoadhesives (See, e.g., U.S. Pat. App. No. 20050281843, hereby incorporated by reference in its entirety). The present invention is not limited by the type of mucoadhesive utilized. Indeed, a variety of mucoadhesives are contemplated to be useful in the present invention including, but not limited to, cross-linked derivatives of poly(acrylic acid) (e.g., carbopol and polycarbophil), polyvinyl alcohol, polyvinyl pyrollidone, polysaccharides (e.g., alginate and chitosan), hydroxypropyl methylcellulose, lectins, fimbrial proteins, and carboxymethylcellulose. Although an understanding of the mechanism is not necessary to practice the present invention and the present invention is not limited to any particular mechanism of action, in some embodiments, use of a mucoadhesive (e.g., in a composition comprising a NE and immunogen) enhances induction of an immune response in a subject (e.g., administered a composition of the present invention) due to an increase in duration and/or amount of exposure to an immunogen that a subject experiences when a mucoadhesive is used compared to the duration and/or amount of exposure to an immunogen in the absence of using the mucoadhesive.

In some embodiments, a composition of the present invention may comprise sterile aqueous preparations. Acceptable vehicles and solvents include, but are not limited to, water, Ringer's solution, phosphate buffered saline and isotonic sodium chloride solution. In addition, sterile, fixed oils are conventionally employed as a solvent or suspending medium. For this purpose any bland fixed mineral or non-mineral oil may be employed including synthetic mono-ordi-glycerides. In addition, fatty acids such as oleic acid find use in the preparation of injectables. Carrier formulations suitable for mucosal, subcutaneous, intramuscular, intraperitoneal, intravenous, or administration via other routes may be found in Remington's Pharmaceutical Sciences, Mack Publishing Company, Easton, Pa.

A composition comprising a NE and an immunogen of the present invention can be used therapeutically (e.g., to enhance an immune response) or as a prophylactic (e.g., for immunization (e.g., to prevent signs or symptoms of disease)). A composition comprising a NE and an immunogen of the present invention can be administered to a subject via a number of different delivery routes and methods.

For example, the compositions of the present invention can be administered to a subject (e.g., mucosally (e.g., nasal mucosa, vaginal mucosa, etc.)) by multiple methods, including, but not limited to: being suspended in a solution and applied to a surface; being suspended in a solution and sprayed onto a surface using a spray applicator; being mixed with a mucoadhesive and applied (e.g., sprayed or wiped) onto a surface (e.g., mucosal surface); being placed on or impregnated onto a nasal and/or vaginal applicator and applied; being applied by a controlled-release mechanism; being applied as a liposome; or being applied on a polymer.

In some preferred embodiments, compositions of the present invention are administered mucosally (e.g., using standard techniques; See, e.g., Remington: The Science and Practice of Pharmacy, Mack Publishing Company, Easton, Pa., 19th edition, 1995 (e.g., for mucosal delivery techniques, including intranasal, pulmonary, vaginal and rectal techniques), as well as European Publication No. 517,565 and Ilium et al., J. Controlled Rel., 1994, 29:133-141 (e.g., for techniques of intranasal administration), each of which is hereby incorporated by reference in its entirety). Alternatively, the compositions of the present invention may be administered dermally or transdermally, using standard techniques (See, e.g., Remington: The Science and Practice of Pharmacy, Mack Publishing Company, Easton, Pa., 19th edition, 1995). The present invention is not limited by the route of administration.

Although an understanding of the mechanism is not necessary to practice the present invention and the present invention is not limited to any particular mechanism of action, in some embodiments, mucosal vaccination is the preferred route of administration as it has been shown that mucosal administration of antigens has a greater efficacy of inducing protective immune responses at mucosal surfaces (e.g., mucosal immunity), the route of entry of many pathogens. In addition, mucosal vaccination, such as intranasal vaccination, may induce mucosal immunity not only in the nasal mucosa, but also in distant mucosal sites such as the genital mucosa (See, e.g., Mestecky, Journal of Clinical Immunology, 7:265-276, 1987). More advantageously, in further preferred embodiments, in addition to inducing mucosal immune responses, mucosal vaccination also induces systemic immunity. In some embodiments, non-parenteral administration (e.g., mucosal administration of vaccines) provides an efficient and convenient way to boost systemic immunity (e.g., induced by parenteral or mucosal vaccination (e.g., in cases where multiple boosts are used to sustain a vigorous systemic immunity)).

In some embodiments, a composition comprising a NE and an immunogen of the present invention may be used to protect or treat a subject susceptible to, or suffering from, disease by means of administering a composition of the present invention via a mucosal route (e.g., an oral/alimentary or nasal route). Alternative mucosal routes include intravaginal and intra-rectal routes. In preferred embodiments of the present invention, a nasal route of administration is used, termed "intranasal administration" or "intranasal vaccination" herein. Methods of intranasal vaccination are well known in the art, including the administration of a droplet or spray form of the vaccine into the nasopharynx of a subject to be immunized. In some embodiments, a nebulized or aerosolized composition comprising a NE and immunogen is provided. Enteric formulations such as gastro resistant capsules for oral administration, suppositories for rectal or vaginal administration also form part of this invention. Compositions of the present invention may also be administered via the oral route. Under these circumstances, a composition comprising a NE and an immunogen may comprise a pharmaceutically acceptable excipient and/or include alkaline buffers, or enteric capsules. Formulations for nasal delivery may include those with dextran or cyclodextran and saponin as an adjuvant.

Compositions of the present invention may also be administered via a vaginal route. In such cases, a composition comprising a NE and an immunogen may comprise pharmaceutically acceptable excipients and/or emulsifiers, polymers (e.g., CARBOPOL), and other known stabilizers of vaginal creams and suppositories. In some embodiments, compositions of the present invention are administered via a rectal route. In such cases, a composition comprising a NE and an immunogen may comprise excipients and/or waxes and polymers known in the art for forming rectal suppositories.

In some embodiments, the same route of administration (e.g., mucosal administration) is chosen for both a priming and boosting vaccination. In some embodiments, multiple routes of administration are utilized (e.g., at the same time, or, alternatively, sequentially) in order to stimulate an immune response (e.g., using a composition comprising a NE and immunogen of the present invention).

For example, in some embodiments, a composition comprising a NE and an immunogen is administered to a mucosal surface of a subject in either a priming or boosting vaccination regime. Alternatively, in some embodiments, a composition comprising a NE and an immunogen is administered systemically in either a priming or boosting vaccination regime. In some embodiments, a composition comprising a NE and an immunogen is administered to a subject in a priming vaccination regimen via mucosal administration and a boosting regimen via systemic administration. In some embodiments, a composition comprising a NE and an immunogen is administered to a subject in a priming vaccination regimen via systemic administration and a boosting regimen via mucosal administration. Examples of systemic routes of administration include, but are not limited to, a parenteral, intramuscular, intradermal, transdermal, subcutaneous, intraperitoneal or intravenous administration. A composition comprising a NE and an immunogen may be used for both prophylactic and therapeutic purposes.

In some embodiments, compositions of the present invention are administered by pulmonary delivery. For example, a composition of the present invention can be delivered to the lungs of a subject (e.g., a human) via inhalation (e.g., thereby traversing across the lung epithelial lining to the blood stream (See, e.g., Adjei, et al. Pharmaceutical Research 1990; 7:565-569; Adjei, et al. Int. J. Pharmaceutics 1990; 63:135-144; Braquet, et al. J. Cardiovascular Pharmacology 1989 143-146; Hubbard, et al. (1989) Annals of Internal Medicine, Vol. III, pp. 206-212; Smith, et al. J. Clin. Invest. 1989; 84:1145-1146; Oswein, et al. "Aerosolization of Proteins", 1990; Proceedings of Symposium on Respiratory Drug Delivery II Keystone, Colo.; Debs, et al. J. Immunol. 1988; 140:3482-3488; and U.S. Pat. No. 5,284,656 to Platz, et al, each of which are hereby incorporated by reference in its entirety). A method and composition for pulmonary delivery of drugs for systemic effect is described in U.S. Pat. No. 5,451,569 to Wong, et al., hereby incorporated by reference; See also U.S. Pat. No. 6,651,655 to Licalsi et al., hereby incorporated by reference in its entirety)).

Further contemplated for use in the practice of this invention are a wide range of mechanical devices designed for pulmonary and/or nasal mucosal delivery of pharmaceutical agents including, but not limited to, nebulizers, metered dose inhalers, and powder inhalers, all of which are familiar to those skilled in the art. Some specific examples of commercially available devices suitable for the practice of this invention are the Ultravent nebulizer (Mallinckrodt Inc., St. Louis, Mo.); the Acorn II nebulizer (Marquest Medical Products, Englewood, Colo.); the Ventolin metered dose inhaler (Glaxo Inc., Research Triangle Park, N.C.); and the Spinhaler powder inhaler (Fisons Corp., Bedford, Mass.). All such devices require the use of formulations suitable for dispensing of the therapeutic agent. Typically, each formulation is specific to the type of device employed and may involve the use of an appropriate propellant material, in addition to the usual diluents, adjuvants, surfactants, carriers and/or other agents useful in therapy. Also, the use of liposomes, microcapsules or microspheres, inclusion complexes, or other types of carriers is contemplated.

Thus, in some embodiments, a composition comprising a NE and an immunogen of the present invention may be used to protect and/or treat a subject susceptible to, or suffering from, a disease by means of administering a compositions comprising a NE and an immunogen by mucosal, intramuscular, intraperitoneal, intradermal, transdermal, pulmonary, intravenous, subcutaneous or other route of administration described herein. Methods of systemic administration of the vaccine preparations may include conventional syringes and needles, or devices designed for ballistic delivery of solid vaccines (See, e.g., WO 99/27961, hereby incorporated by reference), or needleless pressure liquid jet device (See, e.g., U.S. Pat. No. 4,596,556; U.S. Pat. No. 5,993,412, each of which are hereby incorporated by reference), or transdermal patches (See, e.g., WO 97/48440; WO 98/28037, each of which are hereby incorporated by reference). The present invention may also be used to enhance the immunogenicity of antigens applied to the skin (transdermal or transcutaneous delivery, See, e.g., WO 98/20734; WO 98/28037, each of which are hereby incorporated by reference). Thus, in some embodiments, the present invention provides a delivery device for systemic administration, pre-filled with the vaccine composition of the present invention.

The present invention is not limited by the type of subject administered (e.g., in order to stimulate an immune response (e.g., in order to generate protective immunity (e.g., mucosal and/or systemic immunity))) a composition of the present invention. Indeed, a wide variety of subjects are contemplated to be benefited from administration of a composition of the present invention. In preferred embodiments, the subject is a human. In some embodiments, human subjects are of any age (e.g., adults, children, infants, etc.) that have been or are likely to become exposed to a microorganism. In some embodiments, the human subjects are subjects that are more likely to receive a direct exposure to pathogenic microorganisms or that are more likely to display signs and symptoms of disease after exposure to a pathogen (e.g., subjects in the armed forces, government employees, frequent travelers, persons attending or working in a school or daycare, health care workers, an elderly person, an immunocompromised person, and emergency service employees (e.g., police, fire, EMT employees)). In some embodiments, the general public is administered (e.g., vaccinated with) a composition of the present invention (e.g., to prevent the occurrence or spread of disease). For example, in some embodiments, compositions and methods of the present invention are utilized to vaccinate a group of people (e.g., a population of a region, city, state and/or country) for their own health (e.g., to prevent or treat disease) and/or to prevent or reduce the risk of disease spread from animals (e.g., birds, cattle, sheep, pigs, etc.) to humans. In some embodiments, the subjects are non-human mammals (e.g., pigs, cattle, goats, horses, sheep, or other livestock; or mice, rats, rabbits or other animal). In some embodiments, compositions and methods of the present invention are utilized in research settings (e.g., with research animals).

A composition of the present invention may be formulated for administration by any route, such as mucosal, oral, topical, parenteral or other route described herein. The compositions may be in any one or more different forms including, but not limited to, tablets, capsules, powders, granules, lozenges, foams, creams or liquid preparations.

Topical formulations of the present invention may be presented as, for instance, ointments, creams or lotions, foams, and aerosols, and may contain appropriate conventional additives such as preservatives, solvents (e.g., to assist penetration), and emollients in ointments and creams.

Topical formulations may also include agents that enhance penetration of the active ingredients through the skin. Exemplary agents include a binary combination of N-(hydroxyethyl) pyrrolidone and a cell-envelope disordering compound, a sugar ester in combination with a sulfoxide or phosphine oxide, and sucrose monooleate, decyl methyl sulfoxide, and alcohol.

Other exemplary materials that increase skin penetration include surfactants or wetting agents including, but not limited to, polyoxyethylene sorbitan mono-oleoate (Polysorbate 80); sorbitan mono-oleate (Span 80); p-isooctyl polyoxyethylene-phenol polymer (Triton WR-1330); polyoxyethylene sorbitan tri-oleate (Tween 85); dioctyl sodium sulfosuccinate; and sodium sarcosinate (Sarcosyl NL-97); and other pharmaceutically acceptable surfactants.

In certain embodiments of the invention, compositions may further comprise one or more alcohols, zinc-containing compounds, emollients, humectants, thickening and/or gelling agents, neutralizing agents, and surfactants. Water used in the formulations is preferably deionized water having a neutral pH. Additional additives in the topical formulations include, but are not limited to, silicone fluids, dyes, fragrances, pH adjusters, and vitamins.

Topical formulations may also contain compatible conventional carriers, such as cream or ointment bases and ethanol or oleyl alcohol for lotions. Such carriers may be present as from about 1% up to about 98% of the formulation. The ointment base can comprise one or more of petrolatum, mineral oil, ceresin, lanolin alcohol, panthenol, glycerin, bisabolol, cocoa butter and the like.

In some embodiments, pharmaceutical compositions of the present invention may be formulated and used as foams. Pharmaceutical foams include formulations such as, but not limited to, emulsions, microemulsions, creams, jellies and liposomes. While basically similar in nature these formulations vary in the components and the consistency of the final product.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, preferably do not unduly interfere with the biological activities of the components of the compositions of the present invention. The formulations can be sterilized and, if desired, mixed with auxiliary agents (e.g., lubricants, preservatives, stabilizers, wetting agents, emulsifiers, salts for influencing osmotic pressure, buffers, colorings, flavorings and/or aromatic substances and the like) that do not deleteriously interact with the NE and immunogen of the formulation. In some embodiments, immunostimulatory compositions of the present invention are administered in the form of a pharmaceutically acceptable salt. When used the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include, but are not limited to, acetic acid and a salt (1-2% w/v); citric acid and a salt (1-3% w/v); boric acid and a salt (0.5-2.5% w/v); and phosphoric acid and a salt (0.8-2% w/v). Suitable preservatives may include benzalkonium chloride (0.003-0.03% w/v); chlorobutanol (0.3-0.9% w/v); parabens (0.01-0.25% w/v) and thimerosal (0.004-0.02% w/v).

In some embodiments, a composition comprising a NE and an immunogen is co-administered with one or more antibiotics. For example, one or more antibiotics may be administered with, before and/or after administration of a composition comprising a NE and an immunogen. The present invention is not limited by the type of antibiotic co-administered. Indeed, a variety of antibiotics may be co-administered including, but not limited to, β-lactam antibiotics, penicillins (such as natural penicillins, aminopenicillins, penicillinase-resistant penicillins, carboxy penicillins, ureido penicillins), cephalosporins (first generation, second generation, and third generation cephalosporins), and other β-lactams (such as imipenem, monobactams), β-lactamase inhibitors, vancomycin, aminoglycosides and spectinomycin, tetracyclines, chloramphenicol, erythromycin, lincomycin, clindamycin, rifampin, metronidazole, polymyxins, doxycycline, quinolones (e.g., ciprofloxacin), sulfonamides, trimethoprim, and quinolines.

A wide variety of antimicrobial agents are currently available for use in treating bacterial, fungal and viral infections. For a comprehensive treatise on the general classes of such drugs and their mechanisms of action, the skilled artisan is referred to Goodman & Gilman's "The Pharmacological Basis of Therapeutics" Eds. Hardman et al., 9th Edition, Pub. McGraw Hill, chapters 43 through 50, 1996, (herein incorporated by reference in its entirety). Generally, these agents include agents that inhibit cell wall synthesis (e.g., penicillins, cephalosporins, cycloserine, vancomycin, bacitracin); and the imidazole antifungal agents (e.g., miconazole, ketoconazole and clotrimazole); agents that act directly to disrupt the cell membrane of the microorganism (e.g., detergents such as polymyxin and colistimethate and the antifungals nystatin and amphotericin B); agents that affect the ribosomal subunits to inhibit protein synthesis (e.g., chloramphenicol, the tetracyclines, erythromycin and clindamycin); agents that alter protein synthesis and lead to cell death (e.g., aminoglycosides); agents that affect nucleic acid metabolism (e.g., the rifamycins and the quinolones); the antimetabolites (e.g., trimethoprim and sulfonamides); and the nucleic acid analogues such as zidovudine, gangcyclovir, vidarabine, and acyclovir which act to inhibit viral enzymes essential for DNA synthesis. Various combinations of antimicrobials may be employed.

The present invention also includes methods involving co-administration of a composition comprising a NE and an immunogen with one or more additional active and/or immunostimulatory agents (e.g., a composition comprising a NE and a different immunogen, an antibiotic, anti-oxidant, etc.). Indeed, it is a further aspect of this invention to provide methods for enhancing prior art immunostimulatory methods (e.g., immunization methods) and/or pharmaceutical compositions by co-administering a composition of the present invention. In co-administration procedures, the agents may be administered concurrently or sequentially. In one embodiment, the compositions described herein are administered prior to the other active agent(s). The pharmaceutical formulations and modes of administration may be any of those described herein. In addition, the two or more co-administered agents may each be administered using different modes (e.g., routes) or different formulations. The additional agents to be co-administered (e.g., antibiotics, adjuvants, etc.) can be any of the well-known agents in the art, including, but not limited to, those that are currently in clinical use.

In some embodiments, a composition comprising a NE and immunogen is administered to a subject via more than one route. For example, a subject that would benefit from having a protective immune response (e.g., immunity) towards a pathogenic microorganism may benefit from receiving mucosal administration (e.g., nasal administration or other mucosal routes described herein) and, additionally, receiving one or more other routes of administration (e.g., parenteral or pulmonary administration (e.g., via a nebulizer, inhaler, or other methods described herein). In some preferred embodiments, administration via mucosal route is sufficient to induce both mucosal as well as systemic immunity towards an immunogen or organism from which the immunogen is derived. In other embodiments, administration via multiple routes serves to provide both mucosal and systemic immunity. Thus, although an understanding of the mechanism is not necessary to practice the present invention and the present invention is not limited to any particular mechanism of action, in some embodiments, it is contemplated that a subject administered a composition of the present invention via multiple routes of administration (e.g., immunization (e.g., mucosal as well as airway or parenteral administration of a composition comprising a NE and immunogen of the present invention) may have a stronger immune response to an immunogen than a subject administered a composition via just one route.

Other delivery systems can include time-release, delayed release or sustained release delivery systems. Such systems can avoid repeated administrations of the compositions, increasing convenience to the subject and a physician. Many types of release delivery systems are available and known to those of ordinary skill in the art. They include polymer based systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109, hereby incorporated by reference. Delivery systems also include non-polymer systems that are: lipids including sterols such as cholesterol, cholesterol esters and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, each of which is hereby incorporated by reference and (b) diffusional systems in which an active component permeates at a controlled rate from a polymer such as described in U.S. Pat. Nos. 3,854,480, 5,133,974 and 5,407,686, each of which is hereby incorporated by reference. In addition, pump-based hardware delivery systems can be used, some of which are adapted for implantation.

In preferred embodiments, a composition comprising a NE and an immunogen of the present invention comprises a suitable amount of the immunogen to induce an immune response in a subject when administered to the subject. In preferred embodiments, the immune response is sufficient to provide the subject protection (eg., immune protection) against a subsequent exposure to the immunogen or the microorganism (e.g., bacteria or virus) from which the immunogen was derived. The present invention is not limited by the amount of immunogen used. In some preferred embodiments, the amount of immunogen (e.g., virus or bacteria neutralized by the NE, or, recombinant protein) in a composition comprising a NE and immunogen (e.g., for use as an immunization dose) is selected as that amount which induces an immunoprotective response without significant, adverse side effects. The amount will vary depending upon which specific immunogen or combination thereof is/are employed, and can vary from subject to subject, depending on a number of factors including, but not limited to, the species, age and general condition (e.g., health) of the subject, and the mode of administration. Procedures for determining the appropriate amount of immunogen administered to a subject to elicit an immune response (e.g., a protective immune response (e.g., protective immunity)) in a subject are well known to those skilled in the art.

In some embodiments, it is expected that each dose (e.g., of a composition comprising a NE and an immunogen (e.g., administered to a subject to induce an immune response (e.g., a protective immune response (e.g., protective immunity))) comprises 0.05-5000 µg of each immunogen (e.g., recombinant and/or purified protein), in some embodiments, each dose will comprise 1-500 µg, in some embodiments, each dose will comprise 350-750 µm, in some embodiments, each dose will comprise 50-200 µg, in some embodiments, each dose will comprise 25-75 µg of immunogen (e.g., recombinant and/or purified protein). In some embodiments, each dose comprises an amount of the immunogen sufficient to generate an immune response. An effective amount of the immunogen in a dose need not be quantified, as long as the amount of immunogen generates an immune response in a subject when administered to the subject. An optimal amount for a particular administration (e.g., to induce an immune response (e.g., a protective immune response (e.g., protective immunity))) can be ascertained by one of skill in the art using standard studies involving observation of antibody titers and other responses in subjects.

In some embodiments, it is expected that each dose (e.g., of a composition comprising a NE and an immunogen (e.g., administered to a subject to induce and immune response)) is from 0.001 to 15% or more (e.g., 0.001-10%, 0.5-5%, 1-3%, 2%, 6%, 10%, 15% or more) by weight immunogen (e.g., neutralized bacteria or virus, or recombinant and/or purified protein). In some embodiments, an initial or prime administration dose contains more immunogen than a subsequent boost dose In some embodiments, when a NE of the present invention is utilized to inactivate a live microorganism (e.g., a population of bacteria (e.g., of the genus Bacillus (B. anthracis))), it is expected that each dose (e.g., administered to a subject to induce and immune response)) comprises between 10 and $10^{10}$ bacteria per dose; in some embodiments, each dose comprises between $10^5$ and $10^8$ bacteria per dose; in some embodiments, each dose comprises between $10^3$ and $10^5$ bacteria per dose; in some embodiments, each dose comprises between $10^2$ and $10^4$ bacteria per dose; in some embodiments, each dose comprises 10 bacteria per dose; in some embodiments, each dose comprises $10^2$ bacteria per dose; and in some embodiments, each dose comprises $10^4$ bacteria per dose. In some embodiments, each dose comprises more than $10^{10}$ bacteria per dose. In some embodiments, each dose comprises $10^3$ bacteria per dose.

The present invention is not limited by the amount of NE used to inactivate live microorganisms (e.g., bacteria of the genus *Bacillus*). In some embodiments, a 0.1%-5% NE solution is used, in some embodiments, a 5%-20% NE solution is used, in some embodiments, a 20% NE solution is used, and in some embodiments, a NE solution greater than 20% is used order to inactivate a pathogenic microorganism. In preferred embodiments, a 10% NE solution is used.

Similarly, the present invention is not limited by the duration of time a live microorganism is incubated in a NE of the present invention in order to become inactivated. In some embodiments, the microorganism is incubated for 1-3 hours in NE. In some embodiments, the microorganism is incubated for 3-6 hours in NE. In some embodiments, the microorganism is incubated for more than 6 hours in NE. In preferred embodiments, the microorganism is incubated for 3 hours in NE (e.g., a 10% NE solution). In some embodiments, the incubation is carried out at 37° C. In some embodiments, the incubation is carried out at a temperature greater than or less than 37° C. The present invention is also not limited by the amount of microorganism used for inactivation. The amount of microorganism may depend upon a number of factors including, but not limited to, the total amount of immunogenic composition (e.g., NE and immunogen) desired, the concentration of solution desired (e.g., prior to dilution for administration), the microorganism and the NE. In some preferred embodiments, the amount of microorganism used in an inactivation procedure is that amount that produces the desired amount of immunogen (e.g., as described herein) to be administered in a single dose (e.g., diluted from a concentrated stock) to a subject (See, e.g., Example 1).

In some embodiments, a composition comprising a NE and an immunogen of the present invention is formulated in a concentrated dose that can be diluted prior to administration to a subject. For example, dilutions of a concentrated composition may be administered to a subject such that the subject receives any one or more of the specific dosages provided herein. In some embodiments, dilution of a concentrated composition may be made such that a subject is administered (e.g., in a single dose) a composition comprising 0.5-50% of the NE and immunogen present in the concentrated composition. In some preferred embodiments, a subject is administered in a single dose a composition comprising 1% of the NE and immunogen present in the concentrated composition. Concentrated compositions are contemplated to be useful in a setting in which large numbers of subjects may be administered a composition of the present invention (e.g., an immunization clinic, hospital, school, etc.). In some embodiments, a composition comprising a NE and an immunogen of the present invention (e.g., a concentrated composition) is stable at room temperature for more than 1 week, in some embodiments for more than 2 weeks, in some embodiments for more than 3 weeks, in some embodiments for more than 4 weeks, in some embodiments for more than 5 weeks, and in some embodiments for more than 6 weeks.

In some embodiments, following an initial administration of a composition of the present invention (e.g., an initial vaccination), a subject may receive one or more boost administrations (e.g., around 2 weeks, around 3 weeks, around 4 weeks, around 5 weeks, around 6 weeks, around 7 weeks, around 8 weeks, around 10 weeks, around 3 months, around 4 months, around 6 months, around 9 months, around 1 year, around 2 years, around 3 years, around 5 years, around 10 years) subsequent to a first, second, third, fourth, fifth, sixth, seventh, eights, ninth, tenth, and/or more than tenth administration. Although an understanding of the mechanism is not necessary to practice the present invention and the present invention is not limited to any particular mechanism of action, in some embodiments, reintroduction of an immunogen in a boost dose enables vigorous systemic immunity in a subject. The boost can be with the same formulation given for the primary immune response, or can be with a different formulation that contains the immunogen. The dosage regimen will also, at least in part, be determined by the need of the subject and be dependent on the judgment of a practitioner.

Dosage units may be proportionately increased or decreased based on several factors including, but not limited to, the weight, age, and health status of the subject. In addition, dosage units may be increased or decreased for subsequent administrations (e.g., boost administrations).

A composition comprising an immunogen of the present invention finds use where the nature of the infectious and/or disease causing agent (e.g., for which protective immunity is sought to be elicited) is known, as well as where the nature of the infectious and/or disease causing agent is unknown (e.g., in emerging disease (e.g., of pandemic proportion (e.g., influenza or other outbreaks of disease))). For example, the present invention contemplates use of the compositions of the present invention in treatment of or prevention of (e.g., via immunization with an infectious and/or disease causing agent neutralized via a NE of the present invention) infections associated with an emergent infectious and/or disease causing agent yet to be identified (e.g., isolated and/or cultured from a diseased person but without genetic, biochemical or other characterization of the infectious and/or disease causing agent).

It is contemplated that the compositions and methods of the present invention will find use in various settings, including research settings. For example, compositions and methods of the present invention also find use in studies of the immune system (e.g., characterization of adaptive immune responses (e.g., protective immune responses (e.g., mucosal or systemic immunity))). Uses of the compositions and methods provided by the present invention encompass human and non-human subjects and samples from those subjects, and also encompass research applications using these subjects. Compositions and methods of the present invention are also useful in studying and optimizing nanoemulsions, immunogens, and other components and for screening for new components. Thus, it is not intended that the present invention be limited to any particular subject and/or application setting.

The formulations can be tested in vivo in a number of animal models developed for the study of mucosal and other routes of delivery. As is readily apparent, the compositions of the present invention are useful for preventing and/or treating a wide variety of diseases and infections caused by viruses, bacteria, parasites, and fungi, as well as for eliciting an immune response against a variety of antigens. Not only can the compositions be used prophylactically or therapeutically, as described above, the compositions can also be used in order to prepare antibodies, both polyclonal and monoclonal (e.g., for diagnostic purposes), as well as for immunopurification of an antigen of interest. If polyclonal antibodies are desired, a selected mammal, (e.g., mouse, rabbit, goat, horse, etc.) can be immunized with the compositions of the present invention. The animal is usually boosted 2-6 weeks later with one or more—administrations of the antigen. Polyclonal antisera can then be obtained from the immunized animal and used according to known procedures (See, e.g., Jurgens et al., J. Chrom. 1985, 348:363-370).

In some embodiments, the present invention provides a kit comprising a composition comprising a NE and an immunogen. In some embodiments, the kit further provides a device for administering the composition. The present invention is not limited by the type of device included in the kit. In some embodiments, the device is configured for nasal application of the composition of the present invention (e.g., a nasal applicator (e.g., a syringe) or nasal inhaler or nasal mister). In some embodiments, a kit comprises a composition comprising a NE and an immunogen in a concentrated form (e.g., that can be diluted prior to administration to a subject).

In some embodiments, all kit components are present within a single container (e.g., vial or tube). In some embodiments, each kit component is located in a single container (e.g., vial or tube). In some embodiments, one or more kit component are located in a single container (e.g., vial or tube) with other components of the same kit being located in a separate container (e.g., vial or tube). In some embodiments, a kit comprises a buffer. In some embodiments, the kit further comprises instructions for use.

EXPERIMENTAL

The following examples are provided in order to demonstrate and further illustrate certain preferred embodiments and aspects of the present invention and are not to be construed as limiting the scope thereof.

Example 1

Materials and Methods

Animals. Pathogen-free, female Balb/c, CBA/J mice (5-6 weeks old) and Hartley guinea pigs (females, 250 g) were purchased from Charles River Laboratories (Wilmington, Mass.). The mice and guinea pigs were housed in accordance with the American Association for Accreditation of Laboratory Animal Care standards. All procedures involving animals were performed according to the University Committee on Use and Care of Animals (UCUCA) at the University of Michigan, the Institutional Animal Care and Use Committee (IACUC) at the University of Texas Medical Branch at Galveston, Tex., and standard operating procedures at Battelle Memorial Institute, Columbus, Ohio.

Reagents. Recombinant *B. anthracis* protective antigen (rPA) and lethal factor (rLF) were obtained from List Biological Laboratories, Inc. (Campbell, Calif.) and BEI Resource Repository (ATCC) as lyophilized preparations of purified proteins. After reconstitution in sterile MILLI-Q water (5 mg/ml), the aliquots were stored at −80° C. A 20-mer oligonucleotide (ODN) 5'-TCC ATG ACG TTC CGT ACG TT-3' (SEQ ID NO.:1) (See, e.g., Moldoveanu et al., 1999. AIDS Research and Human Retroviruses 15:1469-1476), containing non-methylated CpG repeats, was synthesized by INTEGRATED DNA TECHNOLOGIES (IDT, Coralville, Iowa). The *E. coli* monophosphoryl lipid A (MPL A, #L-6638), PHA-P, BSA, DTT, and other chemicals used in buffers were purchased from SIGMA-ALDRICH Corporation (St. Louis, Mo.). The phosphate buffered saline (PBS), cell culture media, and fetal bovine serum (FBS) were purchased from GIBCO (Grand Island, N.Y.) and HYCLONE (Logan, Utah), respectively. The bovine serum albumin (BSA), alkaline phosphatase (AP)-conjugated antibodies, goat anti-mouse IgG (#A-3562), and goat anti-mouse IgA (α chain specific, #A-4937) were purchased from SIGMA, and goat anti-mouse IgE HPR-conjugate was bought from BETHYL (#A90-115P, Montgomery, Tex.). The Cell Proliferation Kit (XTT) was purchased from ROCHE DIAGNOSTICS (New Jersey, N.Y.).

rPA/Adjuvant Formulations. Nanoemulsion (formulation $W_{20}5EC$) was obtained from NANOBIO Corporation, Ann Arbor, Mich. This nanoemulsion is manufactured by the emulsification of cetyl pyridium chloride (CPC, 1%), Tween 20 (5%), and ethanol (8%) in water with hot-pressed soybean oil (64%), using a high-speed emulsifier (e.g., prepared by a two-step procedure according to U.S. Pat. No. 6,015,832 issued to NANOBIO Corporation (Ann Arbor, Mich.), herein incorporated by reference in its entirety). Other than the CPC, $W_{20}5EC$ is formulated with surfactants and food substances considered 'Generally Recognized as Safe' (GRAS) by the FDA. $W_{20}5EC$ can be manufactured under Good Manufacturing Practices (GMP) and is stable for at least 18 months at 40° C. without any special storage conditions. Nanoemulsion diameter was determined by dynamic light scattering (DLS) using the NICOMP 380 ZLS (PSS NICOMP Particle Sizing Systems, Santa Barbara, Calif.). The mean droplet size was consistently below 400 nM.

rPA/nanoemulsion formulations were prepared 30 to 60 minutes prior to immunization by mixing rPA protein solution with NE, using saline as diluent. Mice immunization studies were performed using a 20 μg dose of rPA mixed with nanoemulsion concentrations of 0.1% 0.5%, 1% and 2%. For immunization with immunostimulants, 20 μg rPA was mixed with either 5 μg of MPL A or 10 μg CpG oligonucleotides in saline. The rPA aluminum hydroxide formulation (Alu, # A-8222, SIGMA) was prepared following an adsorption procedure as described (See Little et al., 2004 Vaccine 22:2843-2852). Guinea pig immunization studies were performed with 10 μg, 50 μg and 100 μg doses of rPA mixed with 1% NE and saline as diluent. The immunization volume was 10 μl/nare for mice and 50 μl/nare for guinea pigs.

PAGE Analysis of the Recombinant PA. 0.5 μg of rPA protein in saline or mixed with 1% NE was analyzed on 10% NU PAGE NOVEX Bis-Tris gel (INVITROGEN, # NP0301BOX) using a X CELL SURELOCK Mini-Cell platform for electrophoresis. Silver staining was performed according to the INVITROGEN SILVERXPRESS (# LC6100) method. The size of rPA protein was determined with a molecular weight marker MARK12 (INVITROGEN, # LC5677).

In vitro Uptake of Antigen. Fluorescently labeled rPA protein was prepared using the FLUOROTAG FITC Conjugation Kit (#FITC1, SIGMA) according to manufacturer's protocol. Murine dendritic cells (Jaws II) were incubated for 30 min at 37° C. with PA-FITC conjugate in PBS or with PA-FITC mixed in nanoemulsion. The 0.001% NE concentration was chosen to ensure full viability of cells growing as a monolayer culture. After incubation, cells were washed 3 times with PBS and fixed with 1.25% formalin in PBS. Cellular uptake was then analyzed by fluorescent microscopy. The microphotographs were taken with an OLYMPUS IX70 microscope with an IXFLA inverted reflected fluorescence observation attachment. The images were processed using the SPOT basic and SPOT advanced programs.

Immunization Procedures. For each experiment, groups of mice were immunized intranasally (i.n.) with either one or two administrations of experimental vaccine 3 weeks apart. Animals were monitored for adverse reactions, and antibody responses were measured at 3 to 4 week intervals over a period of up to 12 weeks. The immunizations were conducted by first anesthetizing the mice with Isoflurane, then holding them in an inverted position. rPA/NE mixes were applied to the nares with a pipette tip (10 μl per nare) and the animals were then allowed to inhale the material. Hartley guinea pigs were vaccinated intranasally (i.n.) with one or two administrations of vaccine (50 μl per nare) 4 weeks apart and antibody responses were measured at 3 to 4 week intervals over a period of up to 22 weeks.

Blood Collection, Bronchial Alveolar Lavage (BAL) and Splenocytes. Blood samples were obtained from the saphenous vein at various time points during the course of the trials. The terminal sample was obtained by cardiac puncture from euthanized, premorbid mice. Serum was obtained from blood by centrifugation at 1500×g for 5 minutes after allowing it to coagulate for 30 to 60 minutes at room temperature. Serum samples were stored at −20° C. until analyzed.

BAL fluid was obtained from mice euthanized by Isoflurane inhalation. After the trachea was dissected, a 22GA catheter (ANGIOCATH, B-D) attached to a syringe was inserted into the trachea. The lungs were infused twice with 0.5 ml of PBS containing 10 μM DTT and 0.5 mg/ml aprotinin (protease inhibitors) and approximately 1 ml of aspirate was recovered. BAL samples were stored at −20° C. for further study.

Murine splenocytes were mechanically isolated to obtain single-cell suspension in PBS. Red blood cells (RBC) were removed by lysis with ACK buffer (150 mM $NH_4Cl$, 10 mM $KHCO_3$, 0.1 mM $Na_2EDTA$), and the remaining cells were washed twice in PBS. For the antigen specific proliferation or cytokine expression assays, splenocytes ($2\text{-}4\times10^6$/ml) were resuspended in RPMI 1640 medium supplemented with 2% FBS, 200 nM L-glutamine, and penicillin/streptomycin (100 U/ml and 100 μg/ml).

Determination of Anti-PA IgG and IgA. Mouse anti-PA-specific IgG and IgA levels were determined by ELISA. Microtiter plates (NUNC) were coated with 5 μg/ml (100 μl) of rPA in a coating buffer (50 mM sodium carbonate, 50 mM sodium bicarbonate, pH 9.6) and incubated overnight at 4° C. After the protein solution was removed, plates were blocked for 30 minutes with PBS containing 1% dry milk. The blocking solution was aspirated and plates were used immediately or stored sealed at 4° C. until needed. Serum and BAL samples were serially diluted in 0.1% BSA in PBS, and 100 μl/well aliquots were incubated in rPA-coated plates for 1 hour at 37° C. Plates were washed three times with PBS-0.05% Tween 20, followed by 1 hour incubation with either anti-mouse IgG or anti-mouse IgA alkaline phosphatase (AP)-conjugated antibodies (ROCKLAND), then washed three times and incubated with AP substrate SIGMAFAST (SIGMA). The colorimetric reaction was stopped with 1 N NaOH according to the manufacturer's protocol, and readouts were performed using a SPECTRAMAX 340 ELISA reader (MOLECULAR DEVICES, Sunnyvale, Calif.) at 405 nm and the reference wavelength of 690 nm. The endpoint titers were recorded and, in case of BAL fluid, the final antibody concentrations were calculated (See Rhie et al., 2003 PNAS 100:10925-10930) from the standard curves obtained for each assay plate, using goat $F(ab')_2$ anti-mouse IgG as a capturing agent and known concentrations of mouse IgG and IgA immunoglobulins, and detected with anti-IgG or anti-IgA-AP conjugates. Guinea pig anti-PA IgG was determined by the same method, except that rabbit anti-guinea pig IgG alkaline phosphatase (AP)-conjugate was used for detection (ROCKLAND). Antibody concentrations are presented as the mean+/−sem (standard error of the mean) of endpoint titers.

Dot-blot Detection of IgE. Saline rPA solution (2 μl, 5 μg/ml) was adsorbed onto NYTRAN membrane (0.2 μm pore, Schleicher and Schuell, Keene, N.H.) and air-dried 30 minutes at room temperature. The membrane was blocked with PBS with 1% dry milk for 30 minutes, then washed 3 times with PBS and air-dried. For IgE detection, pooled sera from all groups of animals were diluted 1:10, 1:20, 1:40 and 1:80 in PBS with 0.1% BSA. The duplicate samples (2 μl) of each dilution were placed over the antigen spots and incubated at RT for 30 minutes. Following 3 washes in PBS, the dot-blot was incubated with a 1:1000 dilution of anti-mouse IgE horseradish peroxidase (HRP)-conjugated antibody. After 5 washes with PBS, the dot-blot was incubated with HPR substrate until dots were visible.

Lethal Toxin (LeTx) Cytotoxicity and Neutralizing Antibodies Assay. Neutralizing antibody assay was performed using serial dilutions of the sera incubated for 1 hour with the LeTx (0.1 μg/ml rPA and 0.1 μg/ml rLF in PBS). The antibody-toxin mixtures were then added to RAW264.7 (20,000-30,000 cells/well) and incubated for 4-6 hours at 37° C. Cell viability was assessed with XTT assay. The serum titers resulting in 50% protection against LeTx cytotoxicity (neutralizing concentration $NC_{50}$) were calculated from the cell viability curves and presented as the mean value of the individual sera.

Live Spore Challenge. Challenge experiments were performed at the BSL4 and BSL3 facilities at Battelle Memorial Institute (Columbus, Ohio) and at the University of Texas Medical Branch (Galveston, Tex.), respectively. The intradermal (i.d.) challenges were performed according to Battelle Study Number: 556-G607602. Briefly, *B. anthracis* (Ames strain) spores were enumerated and diluted for an i.d. spore challenge. A concentrated stock solution of Ames Battelle Lot B22 was diluted in sterile water to an anticipated concentration of $5\times10^3$ colony-forming units per ml (cfu/ml). On Study Day 0, guinea pigs were i.d. challenged with a target dose of ~500 spores (0.1 ml). Post-challenge enumeration of spores revealed the actual number to be 1380, which responds to i.d. 1000 $LD_{50}$. The guinea pigs were observed twice daily for 14 days following the challenge for signs of clinical disease or death. Deaths were recorded to the nearest observation period. All animals surviving the challenge were anesthetized for terminal blood collection and then euthanized on day 14 post-challenge. Intranasal (i.n.) challenges were performed according to the JWP-004-0012 Nasal Challenge SOP protocol. Briefly, *B. anthracis* (Ames strain) spores were enumerated and diluted in PBS without calcium in magnesium for an i.n. spore challenge. Anesthetized guinea pigs were challenged by intranasal administration of either $1.2\times10^6$ or $1.2\times10^7$ spores, which corresponds, respectively, to an intranasal $10\times LD_{50}$ and $100\times LD_{50}$ dose. Post-challenge observation of guinea pigs was performed as described above for intradermal challenge.

Proliferation Assay. The proliferation of mouse splenocytes was measured by an assay of the 5-bromo-2-deoxyuridine (BrdU) incorporation, using CELL PROLIFERATION ELISA, (ROCHE Molecular Biochemicals, Mannheim, Germany). The cells were incubated in the presence of rPA (5 μg/ml) or PHA-P mitogen (2 μg/ml) for 48 hours and then pulsed with BrdU for 24 hours. Cell proliferation was measured according to the manufacturer's instructions using a SPECTRA MAX 340 ELISA Reader at 370 nm and a reference wavelength of 492 nm.

Analysis of in vitro Cytokine Expression. Freshly isolated mouse splenocytes were seeded at $2\times10^6$ cells/0.5 ml (RPMI 1640, 2% FBS) and incubated with rPA (5 μg/ml) or PHA-P mitogen (2 μg/ml) for 72 hours. Cell culture supernatants were harvested and analyzed for the presence of cytokines. The IL-2, IL-4, IFN-γ and TNF-α cytokine assays were performed using QUANTIKINE ELISA kits (R&D SYSTEMS, Inc., Minneapolis, Minn.), according to the manufacturer's instructions.

Statistical Analysis. Data from individual experiments were expressed as mean+standard error of the mean. Statistical significance was determined by ANOVA analysis of variance using the Student t and Fisher exact tests. All tests were at 95% confidence (two-tailed). A p value<0.05 was considered to be statistically significant.

Example 2

Physical Properties of Mixed rPA/NE Vaccine

Mixing rPA with nanoemulsion (NE) did not appear to alter the antigen's protein structure, as it remained a single discrete band on a non-denaturing PAGE, corresponding to intact, full-length protein with a molecular weight of 83 kD (See FIG. 1A). NE appeared to improve the stability of the rPA, which prevented the progressive degradation due to de-amidation that is observed of the antigens incubated in a buffer solution (See, e.g., Gupta et al., 2003. FEBS Letters 554:505-510; Zomber et al., 2005 Journal of Biological Chemistry 280:39897-39906). The addition of the rPA protein did not alter either the size (359+/−109 nm), appearance, or stability of the nanoemulsion as shown in photomicrographs of NE alone and mixed with antigen (See FIG. 1B).

Example 3

Figure 2:
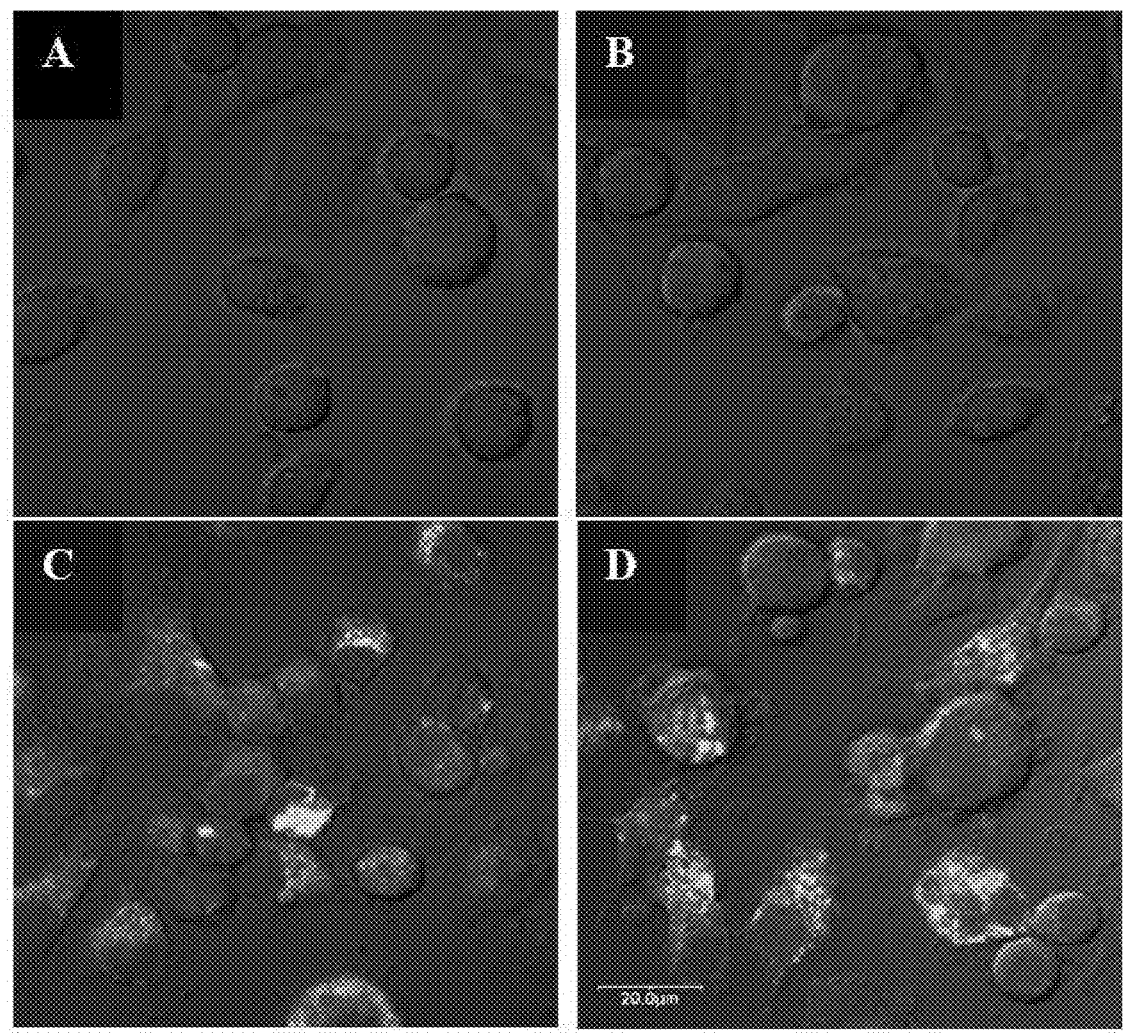
FIG. 2 shows effect of nanoemulsion on the cellular uptake of rPA protein. Jaws II dendritic cells were incubated with either (A) medium, (B) 0.1 µg/ml of PA-FITC alone, (C) 0.1 µg/ml of PA-FITC mixed with 0.001% NE or (D) 1 µg/ml of PA-FITC mixed with 0.001% NE. Green fluorescence indicates that the rPA was effectively internalized only when administered with nanoemulsion.

Nanoemulsion Increases the Uptake of rPA by Dendritic Cells without Inducing an Inflammatory Response Histopathology of nasal mucosa of mice intranasally immunized with either NE alone or mixed with rPA showed no evidence of an inflammatory response at 24 hour intervals up to 4 days post administration. In contrast, in vitro studies documented that mixing rPA with NE significantly increased the uptake of protein in Jaws II dendritic cells (See FIG. 2). Accordingly, in some embodiments, the present invention provides that NE adjuvant activity in vivo involves an increase in the antigen uptake by antigen presenting cells to nasal mucosa (e.g., without the indications of inflammation).

Example 4 rPA/NE Immunization Induces Serum Anti-PA Antibodies

The effect of the nanoemulsion adjuvant on antibody response was measured in CBA/J and Balb/c mice. CBA/J mice were immunized intranasally with 20 μg rPA mixed with either 0.1%, 0.5%, 1%, or 2% concentrations of NE. A rapid induction of anti-PA antibodies in serum was obtained in all vaccinated animals with some dependence on the concentration of the nanoemulsion. All CBA/J mice developed high titers of serum anti-PA IgG (endpoint titers ranging $10^4$ to $10^5$) at 5 weeks after only two administrations of the vaccine (at day 1 and at 3 weeks). Further assays at 8-12 weeks indicated that while there were lower titers in animals immunized with the 0.1% and 0.5% NE, there was no statistical difference between titers in animals immunized with either 1% or 2% rPA/NE. In contrast, no seropositive mice were found in animals intranasally immunized with rPA in saline (See FIG. 3A).

The pattern of the IgG subtype antibodies indicated a prevalence of IgG2a and IgG2b over IgG1. Accordingly, in some embodiments, administration rPA mixed with NE to a subject induces Th1 polarization of the immune response (See FIG. 3A, insert). To further characterize the immune response generated by intranasal nanoemulsion, Balb/c mice were immunized with 20 μs rPA mixed with 1% NE (rPA/NE) and compared to immunization with 20 μg rPA mixed with either MPL A (rPA/MPL A), unmethylated CpG ODN (rPA/CpG) or aluminum hydroxide (rPA/Alu) (See, e.g., Peterson et al., 2006. Infection and Immunity 74:1016-1024; Pittman et al., 2001. Vaccine 20:972-978; Pittman et al., 2002. Vaccine 20:2107-2115; Reuveny et al., 2001. Infect Immun 69:2888-2893). After two administrations of each formulation all mice immunized with rPA/NE were seropositive, with anti-PA IgG endpoint titers of at least $10^5$. This was compared to titers ranging from $10^2$-$10^3$ in the rPA/MPL A, rPA/CpG and rPA/Alu immunization groups (See FIG. 3B). No anti-PA antibodies were detected in animals nasally immunized with rPA in saline.

Serum was also analyzed for the presence of anti-PA IgE antibodies and revealed IgE anti-PA (detectable in at least 1:80 dilution in dot blots) in mice intramuscularly immunized with rPA/Alu, but not in any other group (See FIG. 3B, insert). This is consistent with reports of alum adjuvant-based vaccines inducing a Th2 response (See, e.g., Johansson et al., 2004. Vaccine 22:2873-2880; Lindblad, 2004. Vaccine 22:3658-3668).

Example 5

Intranasal rPA/NE Vaccination Produces Mucosal Immunity

Figure 4:
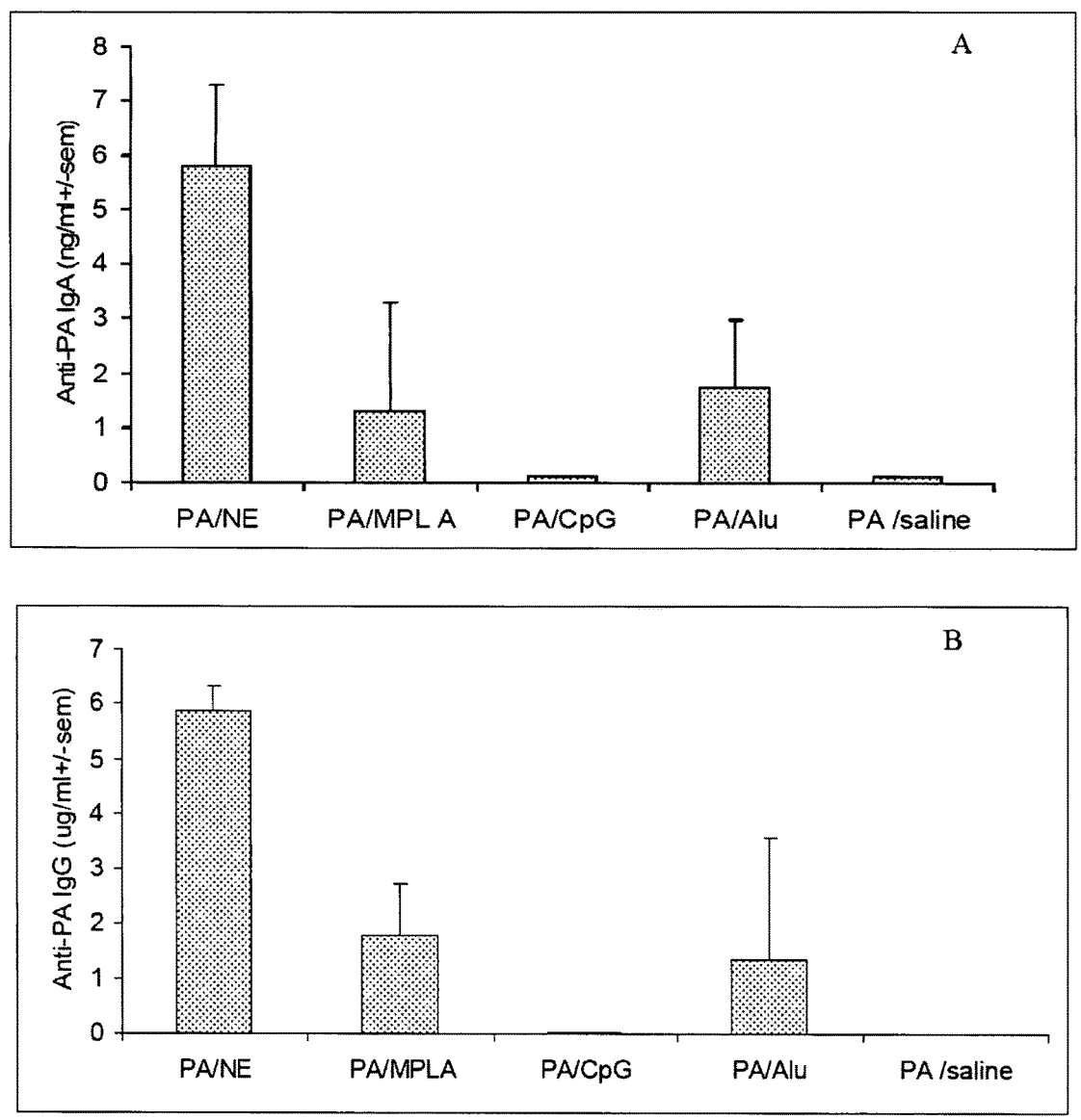
FIG. 4 shows anti-PA IgA and IgG antibodies in bronchial lavage. The anti-PA IgA (A) and anti-PA IgG (B) determined by ELISA of bronchial alveolar lavage (BAL) from Balb/c mice vaccinated with various formulations of vaccine. Anti-PA IgA and anti-PA IgG antibodies are expressed as the mean+/−sem of antibody concentrations.

It was determined whether nasal immunization could induce mucosal immunity (e.g., that protects against respiratory infection (See, e.g., Davis, 2001 Advanced Drug Delivery Reviews 51:21-42; Zuercher, 2003. Viral Immunology 16:279-289). Significant levels of anti-PA-specific secretory IgA antibodies were observed in bronchial lavage (BAL) samples from Balb/c mice vaccinated with rPA/NE (See FIG. 4A). A similar pattern, with higher antibody concentrations, was detected for anti-PA IgG in BAL (See FIG. 4B). The animals with titers of secretory IgA in BAL also had detectable levels of serum anti-PA IgA. Thus, the present invention provides that significant mucosal immune responses are induced via nasal administration of a vaccine comprising rPA in NE, but not with intramuscular immunization. No inflammatory response was observed in histopathological examination of animals' nasal mucosa after administration of NE with or without antigen, indicating that the nanoemulsion is not pro-inflammatory.

Example 6 rPA/NE Vaccines Produce Neutralizing Antibodies Against Anthrax Toxin in Mice

Figure 5:
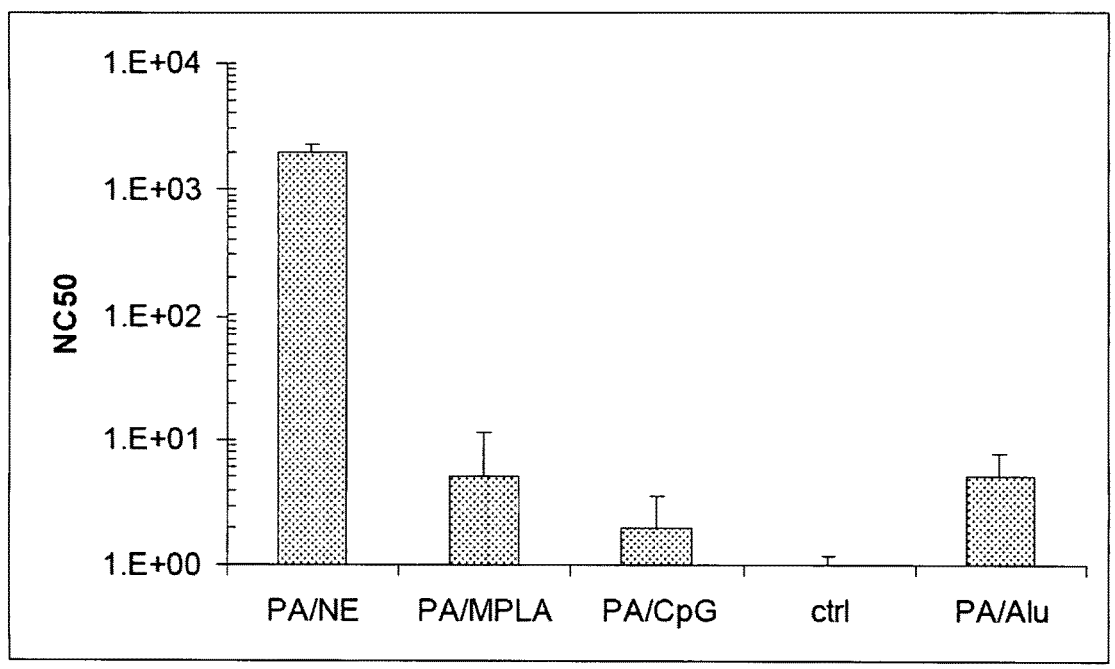
FIG. 5 shows lethal toxin (LeTx) neutralization in vitro. RAW264.7 cells were treated with the anthrax LeTx that had been preincubated with a serial dilution of immune, pooled Balb/c sera. Bars represent the antibody dilution in which cells retain 50% viability ($NC_{50}$).

In order to evaluate whether mucosal nanoemulsion-based vaccine could produce toxin neutralizing antibodies, sera from immunized mice were tested for the ability to neutralize anthrax lethal toxin (LeTx). Sera from mice immunized with rPA/NE were effective in neutralizing LeTx and prevented RAW264.7 cell death with an $NC_{50}$>$10^3$. In contrast, sera from mice immunized with either rPA/MPL A, rPA/CpG or rPA/Alu had $NC_{50}$<10. Naive control sera or sera from mice immunized with rPA in saline did not inhibit LeTx cytotoxicity at any concentration (See FIG. 5).

Example 7 rPA/NE Immunization Yields Th1 Cellular Responses

Figure 6:
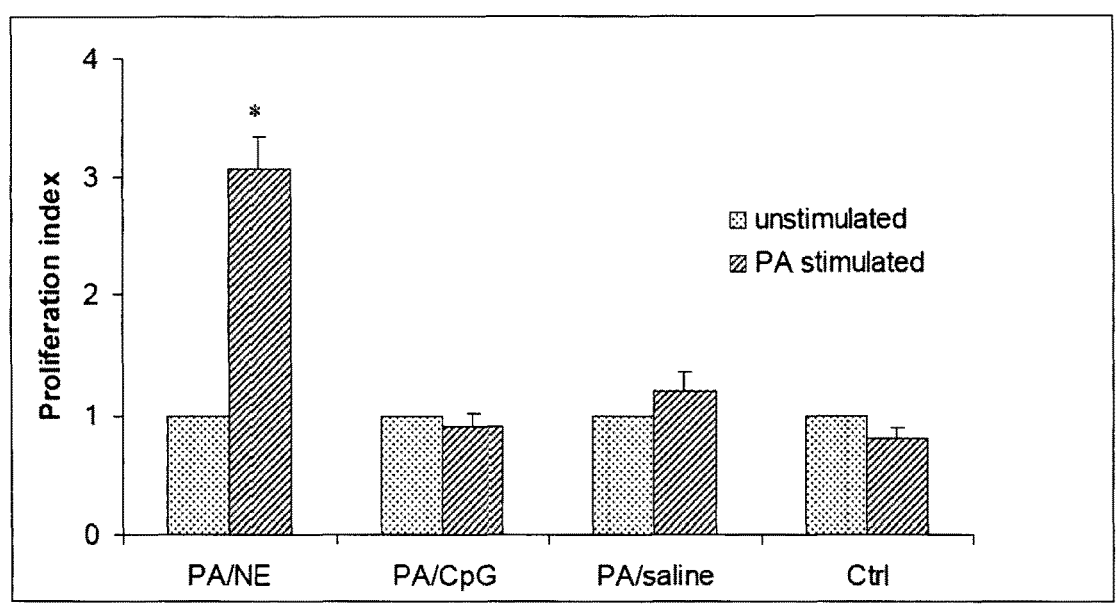
FIG. 6 shows PA-specific induction of splenocyte proliferation in vitro. Splenocytes isolated from immunized mice were stimulated with rPA (5 µg/ml) for 72 hours. Proliferation indexes were calculated as a ratio of the activity in rPA-stimulated cells to the activity in resting splenocytes. (*) Indicates statistical difference between groups (p<0.05).

PA antigen-specific cellular responses were measured in a proliferation assay (See FIG. 5) and through the analysis of cytokine secretion from splenocytes stimulated in vitro with rPA (See Table 1 below). As shown in FIG. 6, rPA stimulated proliferation in splenocytes obtained from mice immunized with rPA/NE. No antigen-specific proliferation was detected in splenocytes from animals immunized with either rPA alone or rPA with CpG ODNs.

PA-activated spleen cells showed extensive production of INF-$\gamma$, TNF-$\alpha$, and IL-2, but failed to produce IL-4 when compared to control (non-stimulated) cells. Thus, in some embodiments, the present invention provides that immunization (e.g., nasal administration) with rPA/NE yields specific Th1-type polarized cellular responses (See Table 1, below). In contrast, splenocyte cultures incubated with PHA induced significant proliferation and the secretion of both Th1 and Th2 cytokines.

TABLE 1

| | PA/NE | | Ctrl | |
| --- | --- | --- | --- | --- |
| | −PA | +PA | −PA | +PA |
| IFN-$\gamma$ | 26.37 ± 8.10 | 93.30 ± 24.40* | 13.23 ± 2.33 | 15.40 ± 3.70 |
| TNF-$\alpha$ | 4.74 ± 2.62 | 22.62 ± 12.85* | 3.51 ± 2.34 | 2.50 ± 2.50 |
| IL-2 | 27.10 ± 2.62 | 59.00 ± 16.9* | 33.00 ± 17.30 | 35.00 ± 16.90 |
| IL-4 | 17.44 ± 2.17 | 21.76 ± 9.76 | 19.00 ± 2.73 | 18.17 ± 2.69 |

Example 8 rPA/NE Vaccines Protect Guinea Pigs Against Intradermal Live Spore Challenge

Figure 7A:
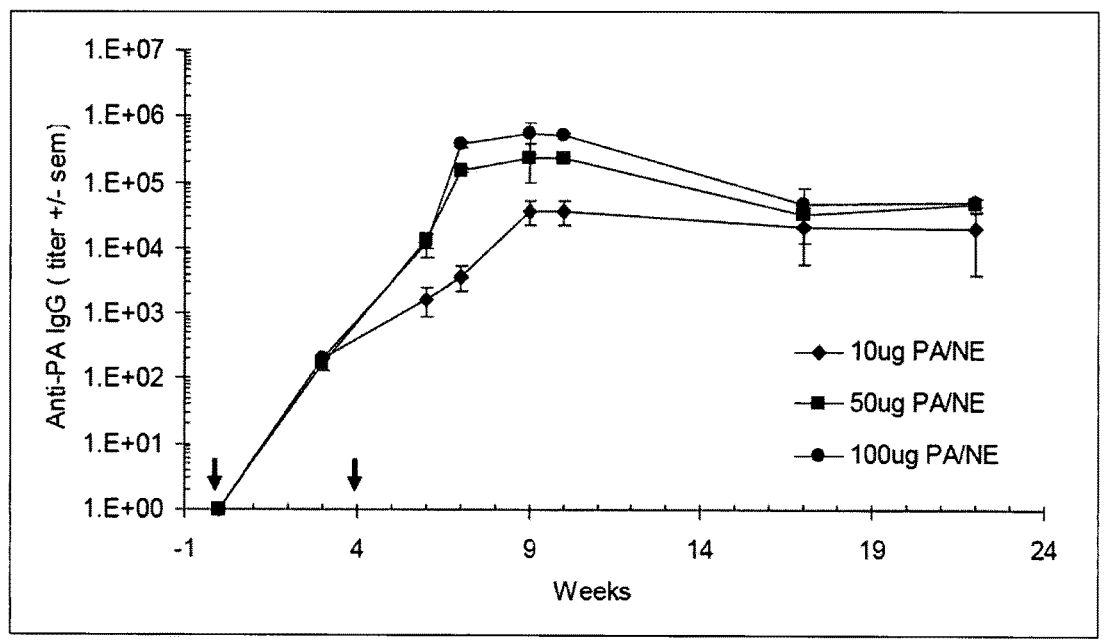
FIG. 7 shows immune response and survival of guinea pigs intranasally immunized with rPA/NE vaccine. Hartley guinea pigs were vaccinated with 2 doses of vaccine (day 1 and at 4 weeks as documented by arrows). (A) Anti-PA IgG in guinea pig serum. Antibody titers were determined at 3- to 4-week intervals with serum anti-PA IgG measured by ELISA (mean endpoint titers+/−sem). (B) Intradermal challenge. At 6 months, guinea pigs were i.d injected with $1000 \times LD_{50}$ of Ames spores and mortality was monitored for 14 days. For vaccinated and control animals (B, insert) LeTx neutralization was performed at 22 weeks before the challenge. The antibody titer in which RAW264 cells retained 50% viability ($NC_{50}$) is determined from the cell viability obtained in at least two assays each performed in triplicate. (*) Indicates statistically significant difference as compared to unvaccinated animals ($p<0.001$).
Figure 7B:
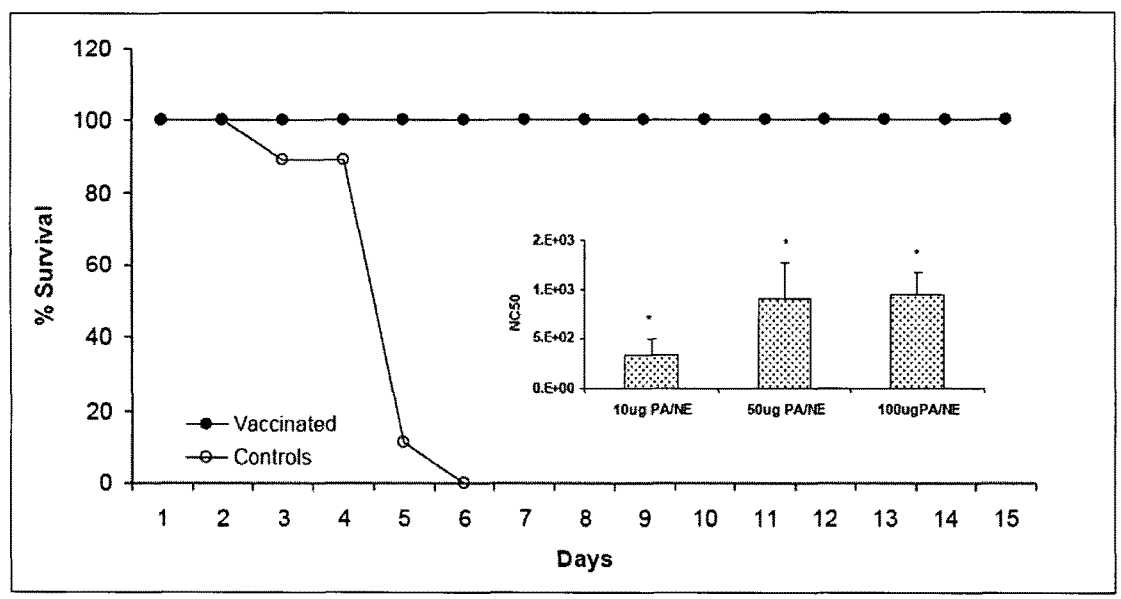

Three groups of guinea pigs were vaccinated intranasally with 10, 50, and 100 μg doses of rPA mixed with 1% NE. IgG responses were observed after a single vaccination and continued to increase after a second administration (at 4 weeks), producing endpoint antibody titers>1×$10^5$. The animals were subsequently followed for 6 months to evaluate the duration of immunity. Nasal immunization in these animals produced durable immune responses with high antibody titers (>$10^4$) for at least 6 months (See FIG. 7A). At 6 months, the animals were challenged intradermally (i.d.) with 1000×$LD_{50}$ Ames strain spores. Survival data indicate that mucosal vaccination of guinea pigs with any of the three concentrations of rPA in NE produced 100% protection against the i.d. challenge, while none of the control animals survived (See FIG. 7B). A LeTx neutralization assay before the challenge documented mean serum $NC_{50}$ titers of 3×$10^2$ in the 10 μg rPA/NE group and $NC_{50}$~1×$10^3$ in both the 50 m and the 100 μg rPA/NE immunized groups (See FIG. 7B insert).

Example 9 rPA/NE Vaccines Protect Against Intranasal Spore Challenge

Figure 8A:
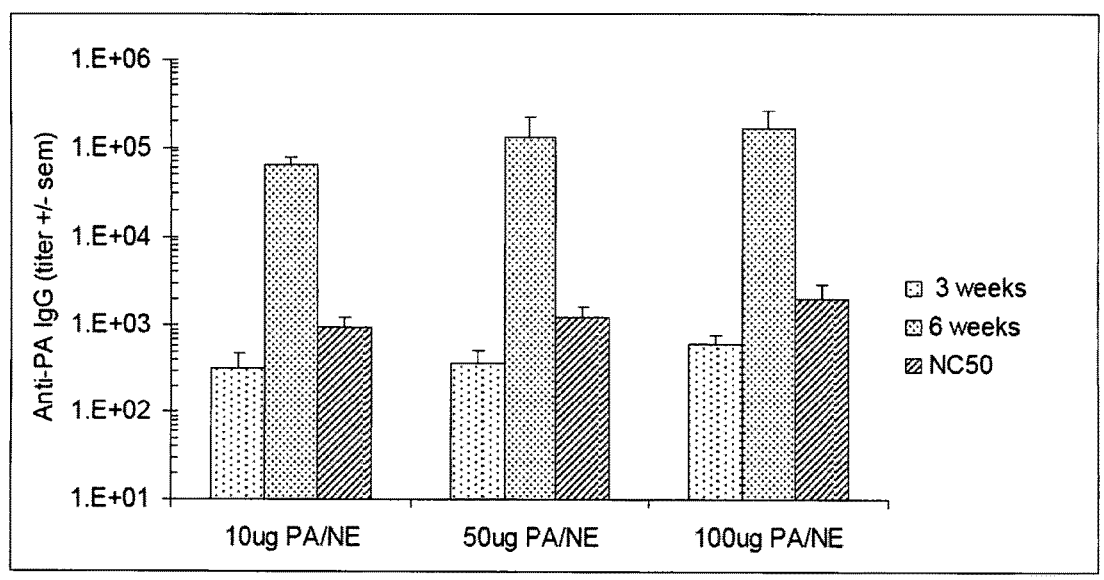
FIG. 8 shows immune response and intranasal challenge of guinea pigs intranasally vaccinated with rPA/NE vaccine. Hartley guinea pigs vaccinated on day 1 and at 4 weeks. (A) Anti-PA IgG and LeTx neutralizing antibody titers in serum. Antibody titers were determined at 3 and 6 weeks and are presented as the mean+/−sem of individual serum anti-PA IgG endpoint titers. The LeTx neutralization assay cell was performed before the challenge, with values representing mean titers in which RAW264 cells retained 50% viability ($NC_{50}$). (B and C) Survival Curves after Intranasal Challenge. At 7 weeks guinea pigs were infected with i.n. instillation of 10 $LD_{50}$ (B) and $100 \times LD_{50}$ (C) of Ames spores, and animals were monitored up to 16 days. (*) Indicates $p<0.05$ between all vaccinated groups as compared to unvaccinated animals.
Figure 8B:
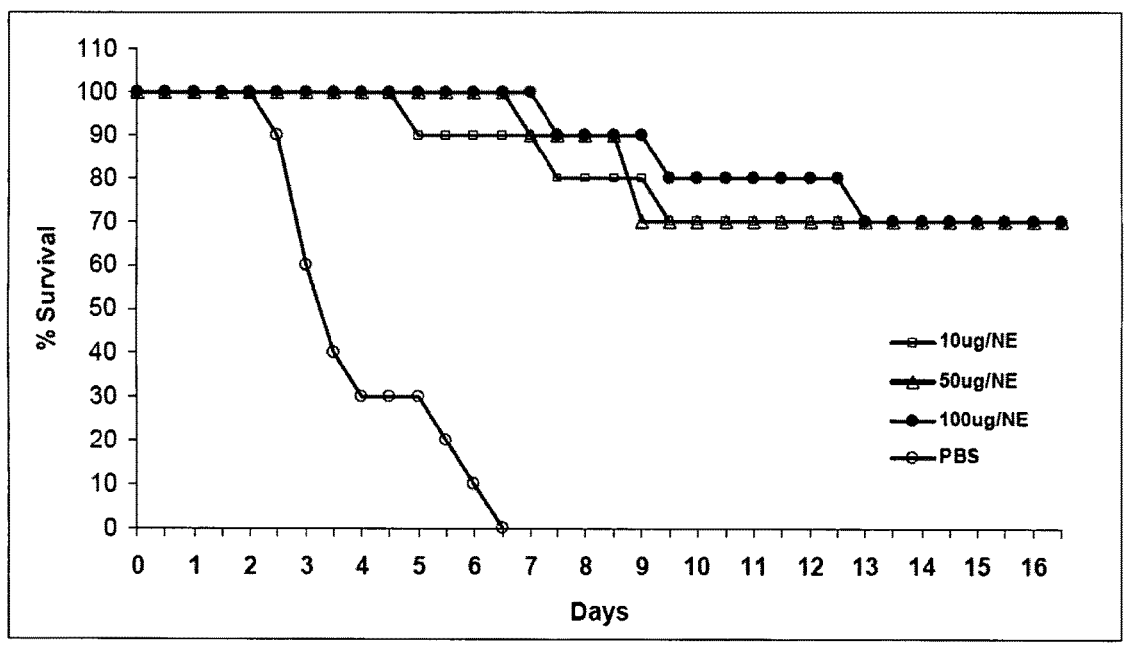
Figure 8C:
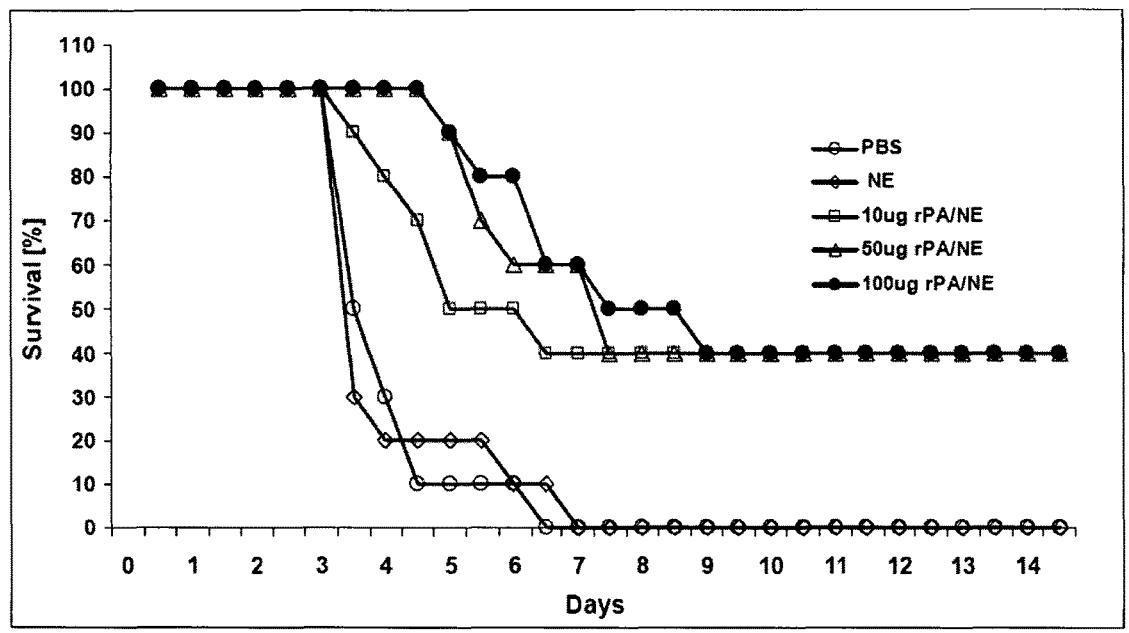

The protective effect of intranasal immunization was also tested in an inhalation challenge trial. Three groups of guinea pigs were immunized with formulations containing 10, 50, and 100 μg rPA mixed with 1% NE. Immunization produced 100% seroconversion and significant anti-PA IgG responses in immunized animals. A boost at 4 weeks resulted in the rapid increase of anti-PA IgG in the serum, producing endpoint antibody titers>$1\times10^5$ in all groups. A LeTx neutralization assay before the challenge indicated a mean $NC_{50}$ titers of $1$-$2\times10^3$ in all vaccinated groups (See FIG. 8A). At 7 weeks the animals were challenged intranasally with either $10\times LD_{50}$ ($1.2\times10^6$ spores) or $100\times LD_{50}$ ($1.2\times10^7$ spores) of B. anthracis Ames strain spores. While none of the control guinea pigs survived, intranasal immunization with each formulation of rPA/NE produced protective immunity. rPA/NE immunizations yielded survival rates of 70% after the $10\times LD_{50}$ challenge and 40% after the $100\times LD_{50}$ challenge (See FIGS. 8B and 8C, respectively). Results of the $10\times LD_{50}$ challenge provide that mucosal rPA/NE vaccine produced protective immunity comparable to i.m. vaccination using rPA with alum (See, e.g., Patton et al., 2006. ASM Bodefense Meeting:Abstract 232). Although there was no difference in the overall survival of the guinea pigs vaccinated with rPA/NE in a range of rPA concentrations, there was a significant, dose-dependent extension of the mean time until death (TTD) in the immunized animals (See Table 2, below).

TABLE 2

| Vaccination | Challenge $10\times LD_{50}$ | | Challenge $100\times LD_{50}$ | |
| --- | --- | --- | --- | --- |
| | Mortality | TTD | Mortality | TTD |
| PBS Ctrl | 10/10 | 3.8 ± 1.4 | 10/10 | 3.1 ± 1.1 |
| NE Ctrl | nd | nd | 10/10 | 3.5 ± 1.1 |
| 10 μg/NE | 3/10 | 7.0 ± 1.4* | 6/10 | 4.3 ± 1.2 |
| 50 μg/NE | 3/10 | 8.3 ± 1.2* | 6/10 | 8.3 ± 1.2* |
| 100 μg/NE | 3/10 | 9.7 ± 3.1* | 6/10 | 6.0 ± 1.4* |

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

We claim:

1. A method of inducing an immune response to Bacillus anthracis (B. anthracis) in a subject comprising intranasally administering an immunogenic composition comprising:
   A) a nanoemulsion, wherein the nanoemulsion comprises:
      1. oil;
      2. water;
      3. ethanol;
      4. a polysorbate surfactant selected from the group consisting of polyoxyethylene sorbitan monooleate and polyoxyethylene sorbitan monolaurate; and
      5. cetylpyridinium chloride (CPC); and
   B) recombinant protective antigen (rPA) of B. anthracis to the subject, wherein the administering generates a B. anthracis-specific immune response comprising generation of a serum anthrax lethal toxin (LeTx)-specific neutralizing antibody titer that is at least 10 fold greater than the serum LeTx-specific neutralizing antibody titer generated in a control subject administered an equal amount of rPA suspended in saline.

2. The method of claim 1, wherein said administering comprises contacting the nasal mucosal surface of said subject with said composition.

3. The method of claim 1, wherein the B. anthracis-specific immune response comprises a systemic IgG response to said rPA of B. anthracis and a mucosal IgA response to said rPA of B. anthracis.

4. The method of claim 1, wherein said immunogenic composition comprises between 1 and 500 μg of said rPA.

5. The method of claim 1, wherein said immunogenic composition comprises 5%-20% nanoemulsion solution.

6. The method of claim 1, wherein said B. anthracis-specific immune response permits said subject to survive a lethal B. anthracis challenge.

7. The method of claim 1, wherein said B. anthracis-specific immune response prevents said subject from displaying signs or symptoms of B. anthracis infection upon subsequent exposure of said subject to live B. anthracis.

8. The method of claim 1, wherein said B. anthracis-specific immune response comprises a rPA-specific Th1 type cell mediated immune response comprising at least a 3 fold increased expression of IFN-γ in said subject compared to a control subject not administered said immunogenic composition.

9. The method of claim 1, wherein said LeTx-specific neutralizing antibody is at least 100 fold greater than the LeTx-specific neutralizing antibody titer generated in a control subject administered an equal amount of rPA suspended in saline.

10. The method of claim 1, said LeTx-specific neutralizing antibody titer is at least 500 fold greater than the LeTx-specific neutralizing antibody titer generated in a control subject administered an equal amount of rPA suspended in saline.

11. The method of claim 1, said LeTx-specific neutralizing antibody titer is at least 1000 fold greater than the LeTx-specific neutralizing antibody titer generated in a control subject administered an equal amount of rPA suspended in saline.

12. The method of claim 1, wherein said immunogenic composition comprises 20-100 µg of said rPA.

13. The method of claim 1, wherein said immunogenic composition comprises a 10% nanoemulsion solution.

14. A method of inducing an immune response to *Bacillus anthracis* (*B. anthracis*) in a subject comprising intranasally administering an immunogenic composition comprising:
   A) a nanoemulsion, wherein the nanoemulsion comprises:
      1. oil;
      2. water;
      3. ethanol;
      4. a polysorbate surfactant selected from the group consisting of polyoxyethylene sorbitan monooleate and polyoxyethylene sorbitan monolaurate; and
      5. cetylpyridinium chloride (CPC); and
   B) recombinant protective antigen (rPA) of *B. anthracis* to the subject, wherein the administering generates a *B. anthracis*-specific immune response comprising generation of a serum anthrax lethal toxin (LeTx)-specific neutralizing antibody titer that permits said subject to survive a lethal *B. anthracis* challenge.

* * * * *

SEQUENCE LISTING

```
<160> NUMBER OF SEQ ID NOS: 1

<210> SEQ ID NO 1
<211> LENGTH: 20
<212> TYPE: DNA
<213> ORGANISM: Artificial
<220> FEATURE:
<223> OTHER INFORMATION: Synthetic

<400> SEQUENCE: 1
tccatgacgt tccgtacgtt                                                  20
```